(12) United States Patent
Lesko et al.

(10) Patent No.: US 11,786,289 B2
(45) Date of Patent: Oct. 17, 2023

(54) END EFFECTOR FOR INSTRUMENT WITH ULTRASONIC BLADE AND BIPOLAR CLAMP ARM

(71) Applicant: Cilag GmbH International, Zug (CH)

(72) Inventors: Jason R. Lesko, Cincinnati, OH (US); Catherine A. Corbett, Cincinnati, OH (US); William B. Weisenburgh, II, Maineville, OH (US); Barry C. Worrell, Centerville, OH (US); Mark A. Davison, Maineville, OH (US); Chad P. Boudreaux, Cincinnati, OH (US); Nathan Cummings, Worcester, MA (US); Ellen Burkart, Cincinnati, OH (US); William D. Dannaher, Cincinnati, OH (US); Christina M. Hough, Cincinnati, OH (US); Craig N. Faller, Batavia, OH (US); Adam N. Brown, Lebanon, OH (US); Jeffrey D. Messerly, Cincinnati, OH (US); Kai Chen, Millburn, NJ (US); William E. Clem, Bozeman, MT (US)

(73) Assignee: Cilag GmbH International, Zug (CH)

( * ) Notice: Subject to any disclaimer, the term of this patent is extended or adjusted under 35 U.S.C. 154(b) by 451 days.

(21) Appl. No.: 16/835,623

(22) Filed: Mar. 31, 2020

(65) Prior Publication Data
US 2020/0315686 A1    Oct. 8, 2020

Related U.S. Application Data

(63) Continuation of application No. 15/355,875, filed on Nov. 18, 2016, now Pat. No. 10,660,692.
(Continued)

(51) Int. Cl.
*A61B 18/12* (2006.01)
*A61B 18/14* (2006.01)
(Continued)

(52) U.S. Cl.
CPC .. *A61B 18/1206* (2013.01); *A61B 17/320092* (2013.01); *A61B 18/1445* (2013.01);
(Continued)

(58) Field of Classification Search
CPC ................ A61B 17/320092; A61B 2018/1445
See application file for complete search history.

(56) References Cited

U.S. PATENT DOCUMENTS

| 3,938,527 A | 2/1976 | Rioux et al. |
| 5,322,055 A | 6/1994 | Davison et al. |

(Continued)

FOREIGN PATENT DOCUMENTS

| CN | 101040799 A | 9/2007 |
| CN | 101141922 A | 3/2008 |

(Continued)

OTHER PUBLICATIONS

Chinese Office Action and Search Report dated Jun. 16, 2020 for Application No. 20680072340.2, 17 pages.
(Continued)

*Primary Examiner* — Daniel W Fowler
(74) *Attorney, Agent, or Firm* — Frost Brown Todd LLP

(57) ABSTRACT

An apparatus includes a body, a shaft assembly, and an end effector. The end effector includes an ultrasonic blade and a clamp arm assembly. The ultrasonic blade is in acoustic communication with an acoustic waveguide of the shaft assembly. The clamp arm assembly is pivotable toward and away from the ultrasonic blade. The clamp arm assembly
(Continued)

includes a first electrode and a second electrode. The first and second electrodes are operable to cooperate to apply bipolar RF energy to tissue.

20 Claims, 30 Drawing Sheets

Related U.S. Application Data

(60) Provisional application No. 62/365,543, filed on Jul. 22, 2016, provisional application No. 62/324,428, filed on Apr. 19, 2016, provisional application No. 62/265,611, filed on Dec. 10, 2015.

(51) Int. Cl.
*A61B 17/32* (2006.01)
*A61B 18/00* (2006.01)

(52) U.S. Cl.
CPC ............ *A61B 2017/320094* (2017.08); *A61B 2017/320095* (2017.08); *A61B 2018/0063* (2013.01); *A61B 2018/00077* (2013.01); *A61B 2018/00083* (2013.01); *A61B 2018/00202* (2013.01); *A61B 2018/00404* (2013.01); *A61B 2018/00595* (2013.01); *A61B 2018/00607* (2013.01); *A61B 2018/00619* (2013.01); *A61B 2018/00791* (2013.01); *A61B 2018/00922* (2013.01); *A61B 2018/00994* (2013.01); *A61B 2018/126* (2013.01); *A61B 2018/142* (2013.01); *A61B 2018/1455* (2013.01)

(56) References Cited

U.S. PATENT DOCUMENTS

| | | | |
|---|---|---|---|
| 5,324,299 A | 6/1994 | Davison et al. | |
| 5,873,873 A | 2/1999 | Smith et al. | |
| 5,980,510 A | 11/1999 | Tsonton et al. | |
| 6,283,981 B1 | 9/2001 | Beaupre | |
| 6,309,400 B2 | 10/2001 | Beaupre | |
| 6,325,811 B1 | 12/2001 | Messerly | |
| 6,423,082 B1 | 7/2002 | Houser et al. | |
| 6,500,176 B1 | 12/2002 | Truckai et al. | |
| 6,773,444 B2 | 8/2004 | Messerly | |
| 6,783,524 B2 | 8/2004 | Anderson et al. | |
| 7,112,201 B2 | 9/2006 | Truckai et al. | |
| 7,125,409 B2 | 10/2006 | Truckai et al. | |
| 7,169,146 B2 | 1/2007 | Truckai et al. | |
| 7,186,253 B2 | 3/2007 | Truckai et al. | |
| 7,189,233 B2 | 3/2007 | Truckai et al. | |
| 7,220,951 B2 | 5/2007 | Truckai et al. | |
| 7,309,849 B2 | 12/2007 | Truckai et al. | |
| 7,311,709 B2 | 12/2007 | Truckai et al. | |
| 7,354,440 B2 | 4/2008 | Truckai et al. | |
| 7,381,209 B2 | 6/2008 | Truckai et al. | |
| 7,544,200 B2 | 6/2009 | Houser | |
| 7,645,278 B2 | 1/2010 | Ichihashi et al. | |
| 7,749,222 B2 | 7/2010 | Lu et al. | |
| 7,819,866 B2 | 10/2010 | Bednarek | |
| 8,057,498 B2 | 11/2011 | Robertson | |
| 8,461,744 B2 | 6/2013 | Wiener et al. | |
| 8,591,536 B2 | 11/2013 | Robertson | |
| 8,623,027 B2 | 1/2014 | Price et al. | |
| 8,663,220 B2 | 3/2014 | Wiener et al. | |
| 8,911,460 B2 | 12/2014 | Neurohr et al. | |
| 8,986,302 B2 | 3/2015 | Aldridge et al. | |
| 9,017,326 B2 | 4/2015 | DiNardo et al. | |
| 9,023,071 B2 | 5/2015 | Miller et al. | |
| 9,095,367 B2 | 8/2015 | Olson et al. | |
| 9,237,900 B2 | 1/2016 | Boudreaux et al. | |
| 9,381,058 B2 | 7/2016 | Houser et al. | |
| 9,393,037 B2 | 7/2016 | Olson et al. | |
| 9,724,120 B2 | 8/2017 | Faller et al. | |
| 9,782,214 B2 | 10/2017 | Houser et al. | |
| 10,028,765 B2 | 7/2018 | Hibner et al. | |
| 10,660,692 B2 | 5/2020 | Lesko et al. | |
| 2003/0171747 A1 | 9/2003 | Kanehira et al. | |
| 2004/0087943 A1 | 5/2004 | Dycus et al. | |
| 2004/0143256 A1 | 7/2004 | Bednarek | |
| 2005/0004570 A1 | 1/2005 | Chapman et al. | |
| 2005/0033278 A1 | 2/2005 | McClurken et al. | |
| 2005/0113827 A1 | 5/2005 | Dumbauld et al. | |
| 2005/0288665 A1* | 12/2005 | Woloszko | A61B 18/1482 604/35 |
| 2006/0058781 A1* | 3/2006 | Long | A61B 18/1477 606/41 |
| 2006/0079874 A1 | 4/2006 | Faller et al. | |
| 2007/0027448 A1* | 2/2007 | Paul | A61B 18/1492 606/41 |
| 2007/0078458 A1 | 4/2007 | Dumbauld et al. | |
| 2007/0156139 A1* | 7/2007 | Schechter | A61B 18/14 606/51 |
| 2007/0191713 A1 | 8/2007 | Eichmann et al. | |
| 2007/0198005 A1* | 8/2007 | Ichihashi | A61B 17/320092 606/27 |
| 2007/0270798 A1 | 11/2007 | Lu et al. | |
| 2007/0282333 A1 | 12/2007 | Fortson et al. | |
| 2008/0132887 A1 | 6/2008 | Masuda et al. | |
| 2008/0195090 A1* | 8/2008 | Takashino | A61B 18/22 606/41 |
| 2008/0200940 A1 | 8/2008 | Eichmann et al. | |
| 2008/0294222 A1 | 11/2008 | Schechter | |
| 2010/0292691 A1 | 11/2010 | Brogna | |
| 2011/0015660 A1 | 1/2011 | Wiener et al. | |
| 2012/0116265 A1 | 5/2012 | Houser et al. | |
| 2012/0116391 A1 | 5/2012 | Houser et al. | |
| 2013/0046303 A1 | 2/2013 | Evans et al. | |
| 2013/0150848 A1 | 6/2013 | Yasunaga | |
| 2014/0135804 A1 | 5/2014 | Weisenburgh, II et al. | |
| 2014/0276785 A1* | 9/2014 | Batchelor | A61B 18/1442 606/41 |
| 2015/0080924 A1 | 3/2015 | Stulen et al. | |
| 2015/0141981 A1 | 5/2015 | Price et al. | |
| 2017/0164972 A1 | 6/2017 | Johnson et al. | |
| 2017/0164997 A1 | 6/2017 | Johnson et al. | |

FOREIGN PATENT DOCUMENTS

| | | |
|---|---|---|
| CN | 102497827 A | 6/2012 |
| CN | 103717160 A | 4/2014 |
| WO | WO 2008/118709 A1 | 10/2008 |
| WO | WO 2013/115036 A1 | 1/2013 |
| WO | WO 2017/100423 A2 | 6/2017 |
| WO | WO 2017/100427 A2 | 6/2017 |

OTHER PUBLICATIONS

International Search Report and Written Opinion dated Sep. 25, 2017 for International Application No. PCT/US2016/065570, 15 pages.
International Search Report and Written Opinion dated Sep. 25, 2017 for International Application No. PCT/US2016/065575, 13 pages.
International Search Report and Written Opinion dated Feb. 2, 2018 for International Application No. PCT/US2017/057871, 11 pages.
Japanese Notification of Reasons for Refusal dated Nov. 17, 2020 for Application No. 2018-530107, 4 pages.
U.S. Appl. No. 61/410,603, filed Nov. 5, 2010.
U.S. Appl. No. 62/265,611, filed Dec. 10, 2015.
U.S. Appl. No. 62/324,428, filed Apr. 19, 2016.
U.S. Appl. No. 62/365,543, filed Jul. 22, 2016.
Brazil Office Action dated Jul. 13, 2020, for Application No. BR112018011660-2, 4 pages.
Chinese Office Action dated Feb. 2, 2021, for Application No. 201680072340.2, 11 pages.
Indian Office Action dated Aug. 31, 2021, for Application No. 201817019939, 5 pages.

(56) References Cited

OTHER PUBLICATIONS

Mexican Office Action dated Aug. 7, 2020, for Application No. MX/a/2018/007072, 4 pages.

* cited by examiner

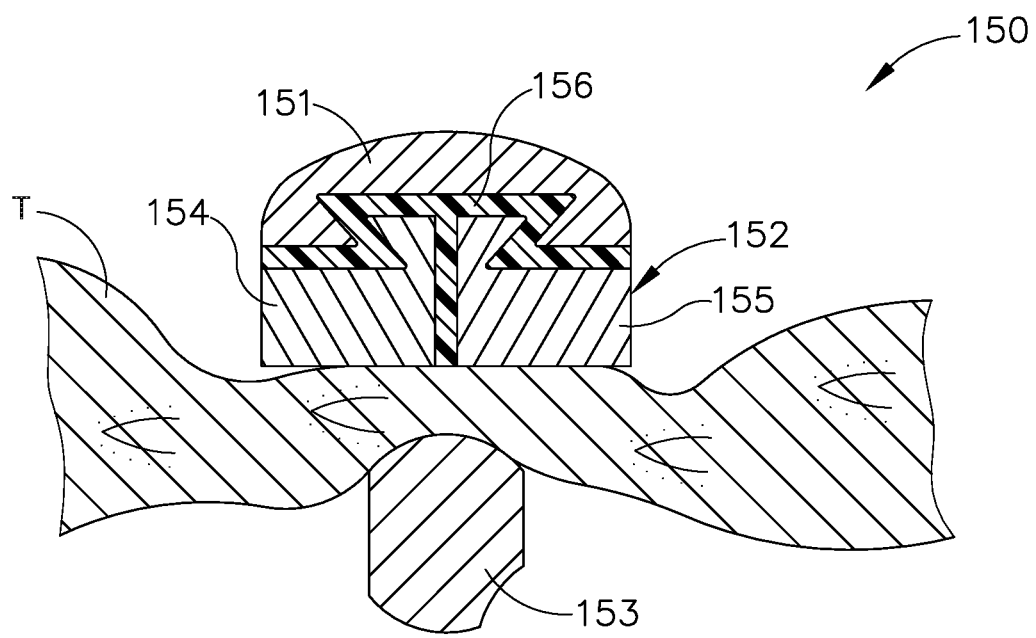
Fig.42
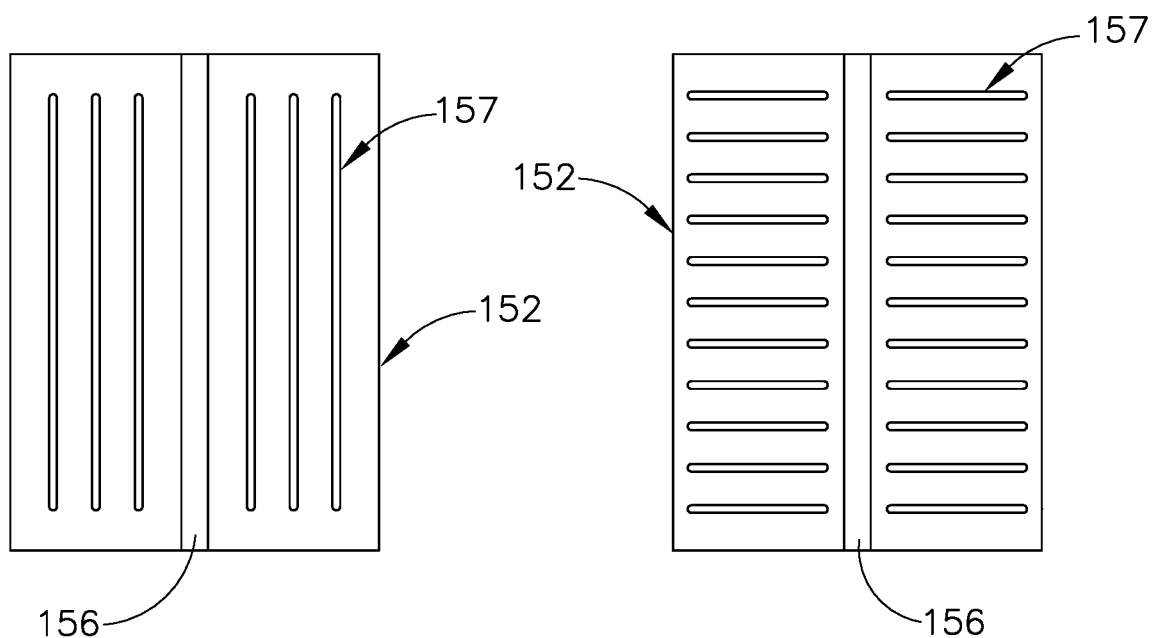
Fig.43
Fig.44

END EFFECTOR FOR INSTRUMENT WITH ULTRASONIC BLADE AND BIPOLAR CLAMP ARM

PRIORITY

This application is a continuation of U.S. patent application Ser. No. 15/355,875, entitled "End Effector for Instrument with Ultrasonic Blade and Bipolar Clamp Arm," filed Nov. 18, 2016, issued as U.S. Pat. No. 10,660,692 on May 26, 2020.

U.S. patent application Ser. No. 15/355,875 claims priority to U.S. Provisional Pat. App. No. 62/265,611, entitled "End Effector for Instrument with Ultrasonic and Electrosurgical Features," filed Dec. 10, 2015, the disclosure of which is incorporated by reference herein.

U.S. patent application Ser. No. 15/355,875 also claims priority to U.S. Provisional Pat. App. No. 62/324,428, entitled "End Effector for Instrument with Ultrasonic and Electrosurgical Features," filed Apr. 19, 2016, the disclosure of which is incorporated by reference herein.

U.S. patent application Ser. No. 15/355,875 also claims priority to U.S. Provisional Pat. App. No. 62/365,543, entitled "End Effector for Instrument with Ultrasonic and Electrosurgical Features," filed Jul. 22, 2016, the disclosure of which is incorporated by reference herein.

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure. The power level used to drive the blade element may be varied (e.g., in real time) based on sensed parameters such as tissue impedance, tissue temperature, tissue thickness, and/or other factors. Some instruments have a clamp arm and clamp pad for grasping tissue with the blade element.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Tissue pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2008/0234710, entitled "Ultrasonic Surgical Instruments," published Sep. 25, 2008, issued as U.S. Pat. No. 8,911,460 on Dec. 16, 2014, the disclosure of which is incorporated by reference herein; and U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pub. No. 2014/0005701, published Jan. 2, 2014, issued as U.S. Pat. No. 9,393,037 on Jul. 19, 2016, entitled "Surgical Instruments with Articulating Shafts," the disclosure of which is incorporated by reference herein; and U.S. Pub. No. 2014/0114334, published Apr. 24, 2014, issued as U.S. Pat.

No. 9,095,367 on Aug. 4, 2015, entitled "Flexible Harmonic Waveguides/Blades for Surgical Instruments," the disclosure of which is incorporated by reference herein.

Some instruments are operable to seal tissue by applying radiofrequency (RF) electrosurgical energy to the tissue. An example of a surgical instrument that is operable to seal tissue by applying RF energy to the tissue is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Some instruments are capable of applying both ultrasonic energy and RF electrosurgical energy to tissue. Examples of such instruments are described in U.S. Pub. No. 2015/0141981, entitled "Ultrasonic Surgical Instrument with Electrosurgical Feature," published May 21, 2015, issued as U.S. Pat. No. 9,949,785 on Apr. 24, 2018, the disclosure of which is incorporated by reference herein; and U.S. Pat. No. 8,663,220, entitled "Ultrasonic Electrosurgical Instruments," issued Mar. 4, 2014, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 42 depicts a cross-section view of another exemplary end effector that may be incorporated into the instrument of FIG. 1;

FIG. 43 depicts a bottom view of an exemplary clamp pad of the end effector of FIG. 42;

FIG. 44 depicts a bottom view of another exemplary clamp pad of the end effector of FIG. 42;

Figure 1:
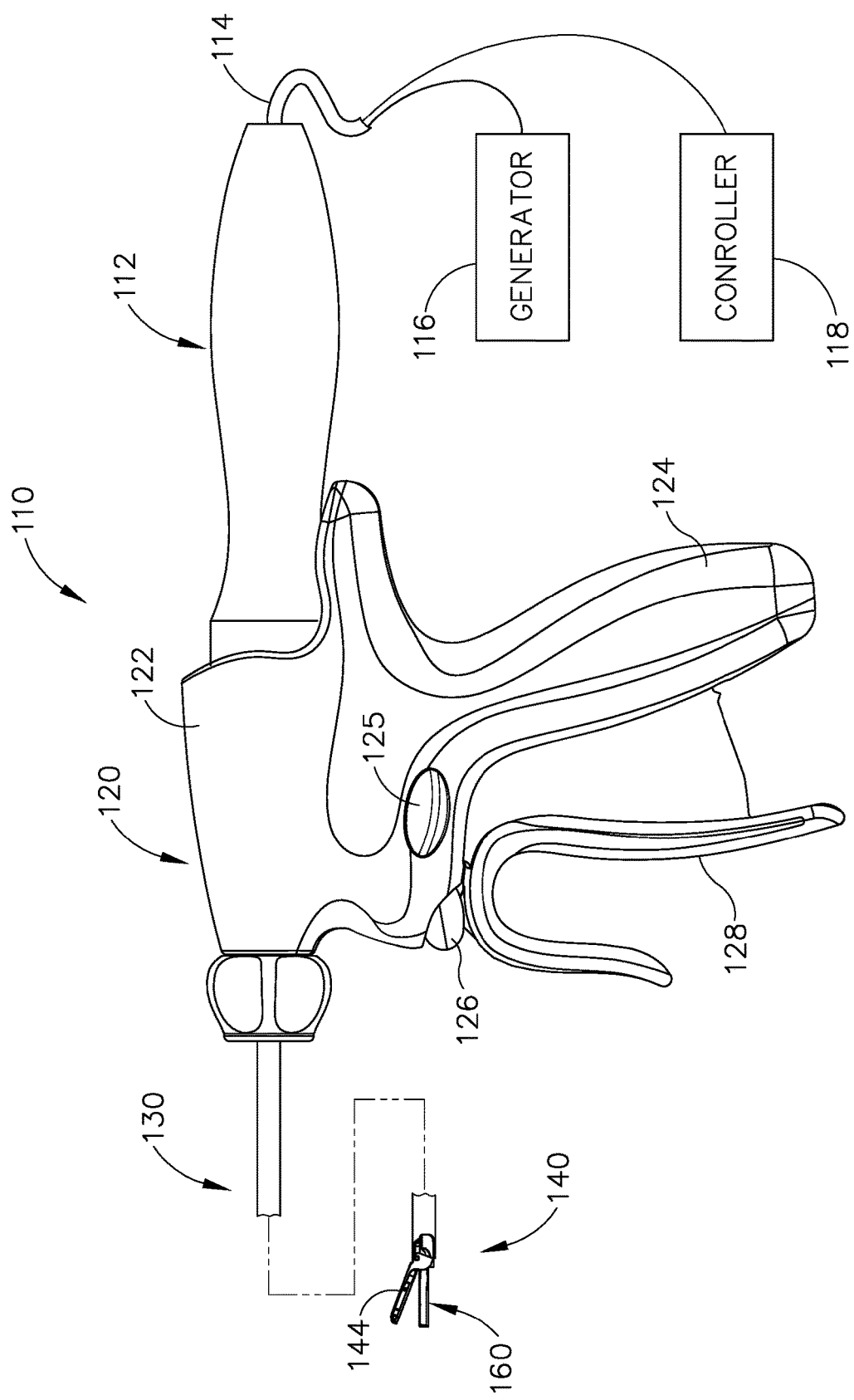
FIG. 1 depicts a side elevational view of an exemplary surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. EXEMPLARY ULTRASONIC SURGICAL INSTRUMENT WITH INTEGRATED RF ENERGY

FIG. 1 illustrates an exemplary ultrasonic surgical instrument (110). At least part of instrument (110) may be constructed and operable in accordance with at least some of the teachings of U.S. Pat. Nos. 5,322,055; 5,873,873; 5,980, 510; 6,325,811; 6,773,444; 6,783,524; 8,461,744; 8,623, 027; U.S. Pub. No. 2006/0079874, now abandoned; U.S. Pub. No. 2007/0191713, now abandoned; U.S. Pub. No. 2007/0282333 now abandoned; U.S. Pub. No. 2008/ 0200940, now abandoned; U.S. Pub. No. 2010/0069940, issued as U.S. Pat. No. 9,023,071 on May 5, 2015; U.S. Pub. No. 2012/0112687, issued as U.S. Pat. No. 9,381,058 on Jul. 5, 2016; U.S. Pub. No. 2012/0116265, now abandoned; U.S. Pub. No. 2014/0005701, issued as U.S. Pat. No. 9,393,037 on Jul. 19, 2016; U.S. Pub. No. 2014/0114334, issued as U.S. Pat. No. 9,095,367 on Aug. 4, 2015; U.S. Pat. App. No. 61/410,603; and/or U.S. patent application Ser. No. 14/028, 717, issued as U.S. Pat. No. 10,172,636 on Jan. 8, 2019. The disclosures of each of the foregoing patents, publications, and applications are incorporated by reference herein. As described therein and as will be described in greater detail below, instrument (110) is operable to cut tissue and seal or weld tissue (e.g., a blood vessel, etc.) substantially simultaneously. It should also be understood that instrument (110) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (110) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (110), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Instrument (110) of the present example comprises a handle assembly (120), a shaft assembly (130), and an end effector (140). Handle assembly (120) comprises a body (122) including a pistol grip (124) and a pair of buttons (125, 126), Handle assembly (120) also includes a trigger (128) that is pivotable toward and away from pistol grip (124). It should be understood, however, that various other suitable configurations may be used, including but not limited to a scissor grip configuration. End effector (140) includes an ultrasonic blade (160) and a pivoting clamp arm (144). Clamp arm (144) is coupled with trigger (128) such that clamp arm (144) is pivotable toward ultrasonic blade (160) in response to pivoting of trigger (128) toward pistol grip (124); and such that clamp arm (144) is pivotable away from ultrasonic blade (160) in response to pivoting of trigger (128) away from pistol grip (124). Various suitable ways in which clamp arm (144) may be coupled with trigger (128) will be apparent to those of ordinary skill in the art in view of the teachings herein. In some versions, one or more resilient members are used to bias clamp arm (144) and/or trigger (128) to the open position shown in FIG. 1.

An ultrasonic transducer assembly (112) extends proximally from body (122) of handle assembly (120) in the present example. In some other versions, transducer assembly (112) is fully integrated within body (122). Transducer assembly (112) receives electrical power from generator (116) and converts that power into ultrasonic vibrations through piezoelectric principles. Generator (116) cooperates with a controller (118) to provide a power profile to transducer assembly (112) that is particularly suited for the generation of ultrasonic vibrations through transducer assembly (112). While controller (118) is represented by a box that is separate from generator (116) in FIG. 1, it should be understood that controller (118) and generator (116) may be integrated together in a single unit. By way of example only, generator (116) may comprise a GEN04, GEN11, or GEN 300 sold by Ethicon Endo-Surgery, Inc. of Cincinnati, Ohio. In addition or in the alternative, generator (116) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. It should also be understood that at least some of the functionality of generator (116) may be integrated into handle assembly (120), and that handle assembly (120) may even include a battery or other on-board power source such that cable (114) is omitted. Still other suitable forms that generator (116) may take, as well as various features and operabilities that generator (116) may provide, will be apparent to those of ordinary skill in the art in view of the teachings herein.

End effector (140) of the present example comprises clamp arm (144) and ultrasonic blade (160). Clamp arm (144) includes a clamp pad that is secured to the underside of clamp arm (144), facing blade (160). By way of example only, the clamp pad may be formed of a polytetrafluoroethylene (PTFE) material and/or any other suitable material(s). By way of further example only, the clamp pad may be further constructed and operable in accordance with at least some of the teachings of U.S. Pat. No. 7,544,200, entitled "Combination Tissue Pad for Use with an Ultrasonic Surgical Instrument," issued Jun. 9, 2009, the disclosure of which is incorporated by reference herein.

Clamp arm (144) is operable to selectively pivot toward and away from blade (160) to selectively clamp tissue between clamp arm (144) and blade (160) in response to pivoting of trigger (128) toward pistol grip (124). Blade (160) of the present example is operable to vibrate at ultrasonic frequencies in order to effectively cut through and seal tissue, particularly when the tissue is being clamped between clamp arm (144) and blade (160). Blade (160) is positioned at the distal end of an acoustic drivetrain that includes an acoustic waveguide (not shown) and transducer assembly (112) to vibrate blade (160). By way of example only, the acoustic waveguide and blade (160) may comprise components sold under product codes SNGHK and SNGCB by Ethicon Endo-Surgery, Inc. of Cincinnati, Ohio. By way of further example only, the acoustic waveguide and blade (160) may be constructed and operable in accordance with the teachings of U.S. Pat. No. 6,423,082, entitled "Ultrasonic Surgical Blade with Improved. Cutting and Coagulation Features," issued Jul. 23, 2002, the disclosure of which is incorporated by reference herein. As another merely illustrative example, the acoustic waveguide and blade (160) may be constructed and operable in accordance with the teachings of U.S. Pat. No. 5,324,299, entitled "Ultrasonic Scalpel Blade and Methods of Application," issued Jun. 28, 1994, the disclosure of which is incorporated by reference herein. Other suitable properties and configurations that may be used for the acoustic waveguide and blade (160) will be apparent to those of ordinary skill in the art in view of the teachings herein.

In the present example, the distal end of blade (160) is located at a position corresponding to an anti-node associated with resonant ultrasonic vibrations communicated through a flexible acoustic waveguide, in order to tune the acoustic assembly to a preferred resonant frequency $f_o$ when the acoustic assembly is not loaded by tissue. When transducer assembly (112) is energized, the distal end of blade (160) is configured to move longitudinally in the range of, for example, approximately 10 to 500 microns peak-to-peak, and in some instances in the range of about 20 to about 200 microns at a predetermined vibratory frequency $f_o$ of, for example, 50 kHz or 55.5 kHz. When transducer assembly (112) of the present example is activated, these mechanical oscillations are transmitted through waveguides to reach blade (160), thereby providing oscillation of blade (160) at the resonant ultrasonic frequency. Thus, when tissue is secured between blade (160) and clamp arm (144), the ultrasonic oscillation of blade (160) may simultaneously sever the tissue and denature the proteins in adjacent tissue cells, thereby providing a coagulative effect with relatively little thermal spread. In some versions, an electrical current may also be provided through blade (160) and clamp arm (144) to also cauterize the tissue. For instance, blade (160) and clamp arm (144) may be configured to apply radiofrequency (RF) electrosurgical energy to tissue in addition to being configured to apply ultrasonic energy to tissue.

End effector (140) of the present example is further operable to apply radiofrequency (RF) electrosurgical energy to tissue that is captured between clamp arm (144) and blade (160). By way of example only, end effector (140) may include a single electrode that cooperates with a conventional ground pad that is secured to the patient, such that end effector (140) applies monopolar RF electrosurgical energy to the tissue. As another merely illustrative example, clamp arm (144) may include two electrodes that are operable to apply bipolar RF electrosurgical energy to the tissue. As yet another merely illustrative example, clamp arm (144) may include a single electrode and ultrasonic blade (160) may serve as a return path, such that ultrasonic blade (160) cooperates with the electrode of clamp arm (144) to apply bipolar RF electrosurgical energy to the tissue. In addition to or as an alternative to the foregoing, end effector (140) may be constructed and operable in accordance with at least some of the teachings of U.S. Pat. No. 8,663,220, entitled "Ultrasonic Electrosurgical Instruments," issued Mar. 4, 2014, the disclosure of which is incorporated by reference herein. Other suitable arrangements will be apparent to those of ordinary skill in the art in view of the teachings herein.

Instrument (110) may provide the operator with various ways in which to selectively apply only ultrasonic energy to tissue via end effector (140), only RF electrosurgical energy to tissue via end effector (140), or some combination of ultrasonic energy and RF electrosurgical energy to tissue via end effector (140). In versions where end effector (140) is operable to apply a combination of ultrasonic energy and RF electrosurgical energy to tissue, end effector (140) may be configured to apply ultrasonic energy and RF electrosurgical energy to tissue simultaneously. In addition or in the alternative, in versions where end effector (140) is operable to apply a combination of ultrasonic energy and RF electrosurgical energy to tissue, end effector (140) may be configured to apply ultrasonic energy and RF electrosurgical energy to tissue in a sequence. Such a sequence may be predetermined; or may be based on sensed tissue conditions (e.g., tissue temperature, density, thickness, etc.). Various suitable control algorithms that may be used are disclosed in U.S. Pub. No. 2015/0141981, entitled "Ultrasonic Surgical Instrument with Electrosurgical Feature," published May 21, 2015, issued as U.S. Pat. No. 9,949,785 on Apr. 24, 2018, the disclosure of which is incorporated by reference herein. It should also be understood that the control of ultrasonic energy and RF electrosurgical energy may be provided in accordance with at least some of the teachings of U.S. Pat. No. 8,663,220, entitled "Ultrasonic Electrosurgical Instruments," issued Mar. 4, 2014, the disclosure of which is incorporated by reference herein.

Buttons (125, 126) may provide the operator with varied control of the energy that is applied to tissue through end effector (140). For instance, in some versions, button (125) may be activated to apply RF electrosurgical energy to tissue; while button (126) may be activated to apply ultrasonic energy to tissue. As another merely illustrative example, button (125) may be activated to apply ultrasonic energy to tissue at a low power level (e.g., without also applying RF electrosurgical energy to tissue, applying RF electrosurgical energy to tissue simultaneously, or applying RF electrosurgical energy to tissue in a sequence with the ultrasonic energy); while button (126) may be activated to apply ultrasonic energy to tissue at a high power level (e.g., without also applying RF electrosurgical energy to tissue, applying RF electrosurgical energy to tissue simultaneously, or applying RF electrosurgical energy to tissue in a sequence with the ultrasonic energy). In addition or in the alternative, buttons (125, 126) may provide functionality in accordance with at least some of the teachings of U.S. Pub. No. 2015/0141981, entitled "Ultrasonic Surgical Instrument with Electrosurgical Feature," published May 21, 2015, issued as U.S. Pat. No. 9,949,785 on Apr. 24, 2018, the disclosure of which is incorporated by reference herein. Other suitable ways in which buttons (125, 126) may provide operation of instrument (110) will be apparent to those of ordinary skill in the art in view of the teachings herein.

II. EXEMPLARY END EFFECTOR CONFIGURATIONS

As noted above, end effector (140) may include various kinds of electrode configurations to apply RF electrosurgical energy to tissue. It should also be understood that ultrasonic blade (160) may have various structural configurations. These various structural configurations of ultrasonic blade (160) may provide different kinds of effects on tissue. In particular, the particular structural configuration of ultrasonic blade (160) may influence the way in which ultrasonic blade (160) applies ultrasonic energy to tissue. For instance, some ultrasonic blade (160) configurations may provide better ultrasonic cutting of tissue while other ultrasonic blade (160) configurations may provide better ultrasonic sealing of tissue. The relationships between the structural configurations of the electrode(s) and ultrasonic blade (160) may also influence the way in which end effector (140) applies RF electrosurgical energy to tissue. The following discussion provides various examples of different end effector configurations. It should be understood that any of the various end effectors described below may be readily incorporated into instrument (110), in place of end effector (140).

It should also be understood that all of the end effectors described below may include features that are configured to ensure that a minimum gap is defined between the variation of clamp arm (144) and the variation of blade (160), even when the variation of end effector (140) is in a fully closed configuration. Such a minimum gap will prevent the variation of clamp arm (144) from contacting the variation of blade (160), which will prevent formation of a short circuit between an electrode of the variation of clamp arm (144) and the variation of blade (160). This may be particularly important when the variation of end effector is being used to provide bipolar RF electrosurgical energy to tissue, with the electrode of the variation of clamp arm (144) providing one pole for the RF electrosurgical energy and the variation of blade (160) providing the other pole for the RF electrosurgical energy. A minimum gap may also selected to prevent arcing of such energy, where the arcing might otherwise occur when a gap is sized below the predetermined minimum amount. By way of example only, a minimum gap may be provided in accordance with at least some of the teachings of U.S. patent application Ser. No. 14/928,375, entitled "Ultrasonic Surgical Instrument Clamp Arm with Proximal Nodal Pad," filed Oct. 30, 2015, issued as U.S. Pat. No. 10,028,765 on Jul. 24, 2018, the disclosure of which is incorporated by reference herein. Other suitable ways in which a minimum gap may be provided will be apparent to those of ordinary skill in the art in view of the teachings herein. Other suitable ways in which a minimum gap may be provided will be apparent to those of ordinary skill in the art in view of the teachings herein.

A. End Effector with Dual Electrode Insert within Clamp Pad

Figure 2:
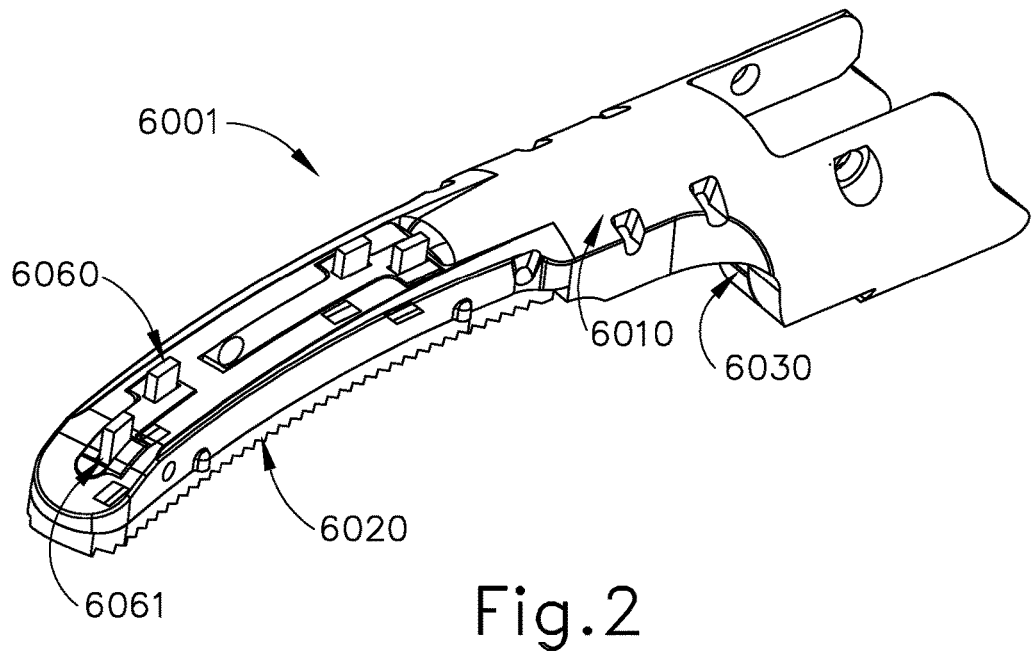
FIG. 2 depicts a perspective view of another exemplary clamp arm assembly of an end effector that may be incorporated into the instrument of FIG. 1.

FIGS. 2-7 show portions of other exemplary end effectors that may be readily incorporated into instrument (110) in place of end effector (140). More specifically, FIG. 2 shows a clamp arm assembly (6001) of end effector (6000) shown in FIG. 3. In the present example, a blade of end effector (6000) is the same as blade (240) as described above, while other blade configurations may be used in other examples. End effector (6000) further comprises a clamp arm (6010), a clamp pad (6020), a clamp pad retainer member (6030), a first electrode (6060), and a second electrode (6061).

Clamp arm (6010) is configured with multiple bores (6011) that align with corresponding bores (6021) of clamp pad (6020) and corresponding bores (6031) of retainer member (6030). Clamp arm (6010) comprises an opening (6012) that is shaped to receive clamp pad (6020), which is formed with corresponding features that are shaped to fit within opening (6012). Similarly, retainer member (6030) is formed with features that are shaped to engage with corresponding features of clamp arm (6010). For example, retainer member (6030) includes a rail (6032) similar to rail (226) described above, with rail (6032) engaging a recess within clamp arm (6010) that is shaped to receive rail (6032). With clamp pad (6020) and retainer member (6030) positioned within clamp arm (6010), multiple pins may be used to secure clamp pad (6020) and retainer member (6030) to clamp arm (6010) by inserting the pins through the aligning bores (6011, 6021, 6031). By way of example only, this method of assembly could be achieved by overmolding clamp pad (6020) and retainer member (6030) to clamp arm (6010) while capturing electrodes (6060, 6061).

First electrode (6060) comprises a pair of contacts or terminals (6062), while second electrode (6061) also comprises a pair of contacts or terminals (6063). In some other versions, the pair of contacts may be modified or replaced such that each electrode (6060, 6061) comprises only a single contact or terminal. First and second electrodes (6060, 6061) also comprise respective body portions (6064, 6065). The pairs of terminals (6062, 6063) extend from their respective body portions (6064, 6065) in a manner such that pairs of terminals (6062, 6063) are generally orthogonal with respect to their respective body portions (6064, 6065).

Figure 3:
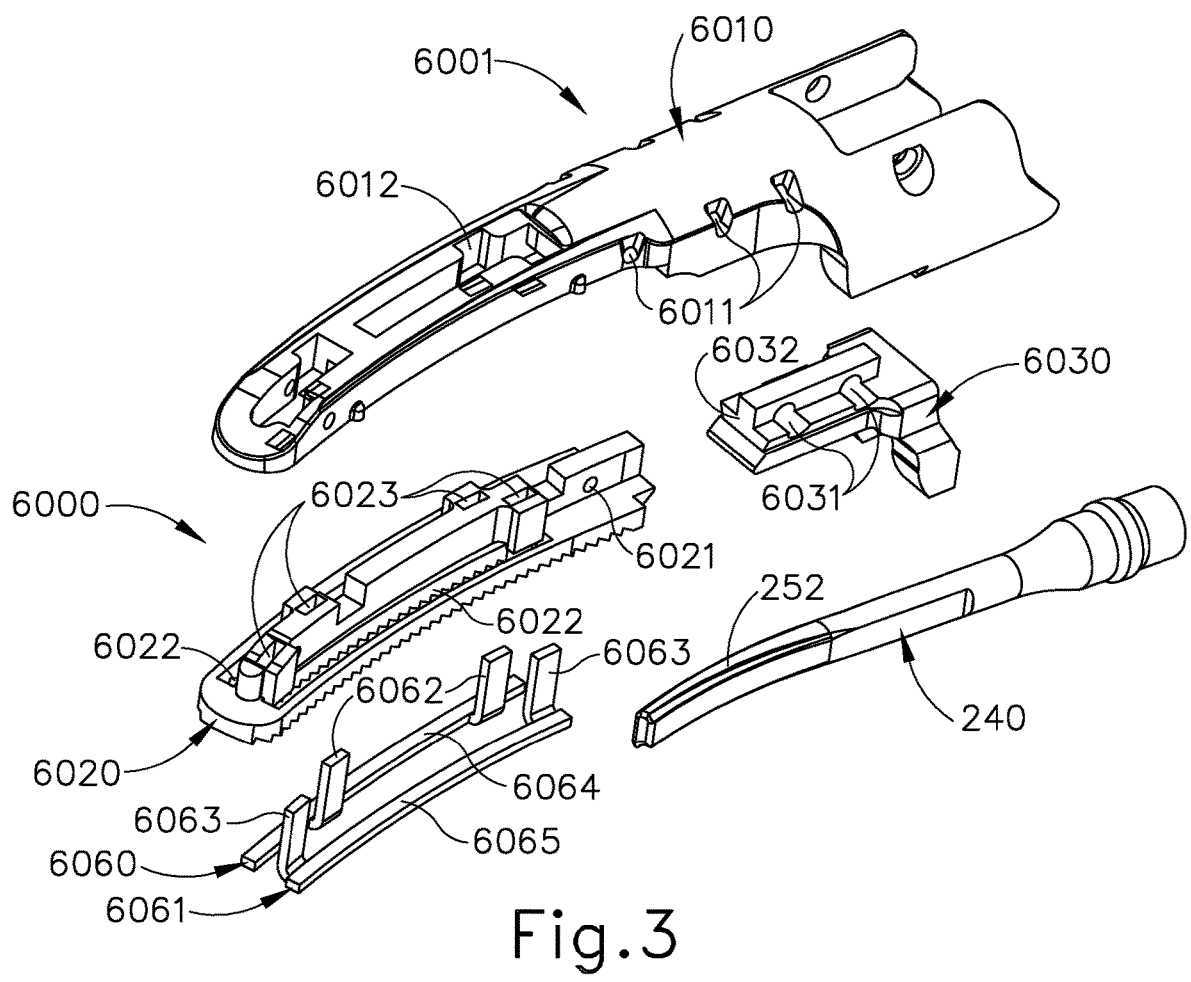
FIG. 3 depicts an exploded view of the clamp arm assembly of FIG. 2 and an ultrasonic blade that forms an end effector with the clamp arm assembly of FIG. 2.
Figure 4:
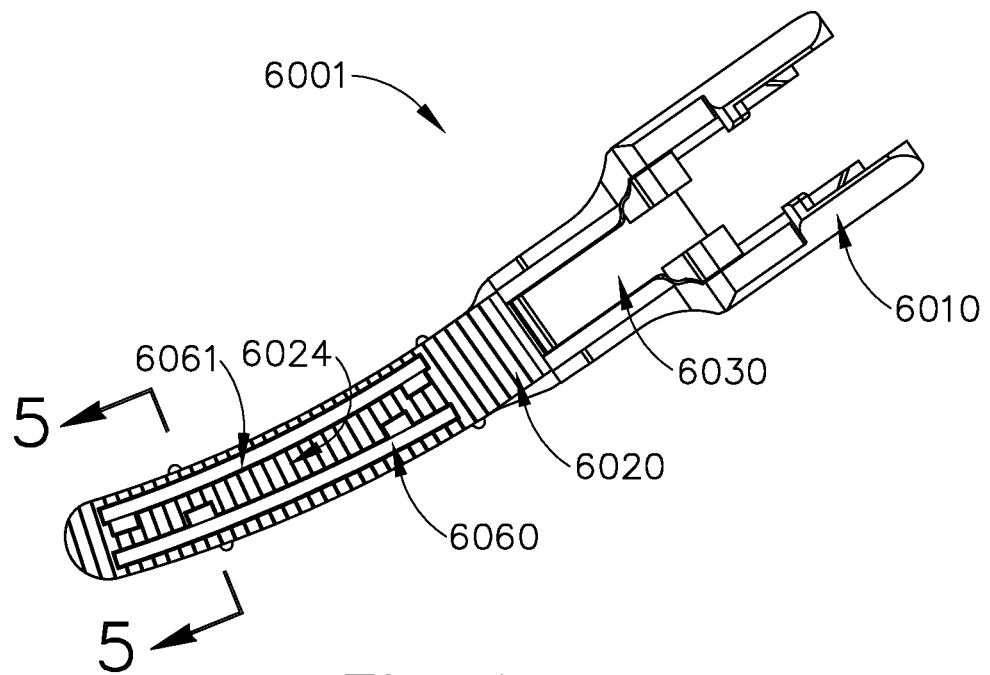
FIG. 4 depicts a bottom view of the clamp arm assembly of FIG. 2.

Referring now also to FIGS. 3 and 4, in the connection with clamp arm assembly (6001), first electrode (6060) is received within clamp pad (6020), with pair of terminals (6062) extending through clamp pad (6020) such that pair of terminals (6062) are exposed and accessible from a top outer region of clamp arm (6010) as seen in FIG. 2, Second electrode (6061) connects with clamp arm assembly (6001) in the same manner as first electrode (6060). To accommodate first and second electrodes (6060, 6061), clamp pad (6020) comprises a pair of longitudinal slots (6022) for receiving body portions (6064, 6065) of electrodes (6060, 6061). Clamp pad (6020) also comprises bores (6023) that allow pairs of terminals (6062, 6063) of electrodes (6060, 6061) to pass through clamp pad (6020) for access from the top outer region of clamp arm (6010). In some other versions, these exposed terminals (6062, 6063) bend 90° and terminate into the proximal end of clamp pad (6020); and connect to an insulated wire.

Figure 5:
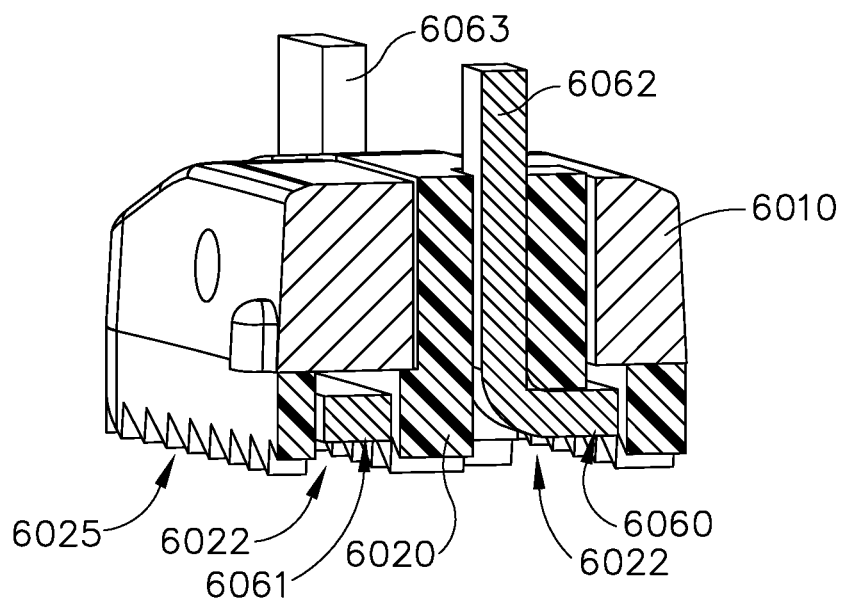
FIG. 5 depicts a perspective cross-sectional view of the clamp arm assembly of FIG. 4 taken along line 5-5 of FIG. 4.

Referring to FIGS. 4 and 5, clamp pad (6020) comprises teeth (6025) as described above. As also described above, end effector (6000) is configured for tissue engagement between blade (240) and the toothed surface of clamp pad (6020). Clamp pad (6020) remains proud relative to the surfaces of electrodes (6060, 6061), such that the surfaces of electrodes (6060, 6061) are recessed relative to the tissue engaging toothed surface of clamp pad (6020). In those regions with longitudinal slots (6022), when tissue is held between clamp pad (6020) and blade (240), tissue can at least partially fill slots (6022) contacting electrodes (6060, 6061). In this manner, a conductive pathway is established through the tissue between electrodes (6060, 6061) and blade (240). Blade (240) is aligned with a centerline region (6024) of clamp pad (6020) that extends between first and second electrodes (6060, 6061). With tissue compressed between clamp pad (6020) and blade (240), ultrasonic energy can be imparted to waveguide (242) and thereby ultrasonically sever the tissue along the continuous centerline region (6024) of clamp pad (6020). On each side of the cut line, ultrasonic sealing occurs as described above. In addition, end effector (6000) is further operable to provide RF electrosurgical sealing of tissue along the conductive pathways described above, which would include tissue that is laterally outward from the cut line formed between upper surface (252) of blade (240) and centerline region (6024) of clamp pad (6020). With the continuously exposed electrodes (6060, 6061) along a majority of the length of clamp pad (6020), RF electrosurgical sealing may be obtained along each side of the length of the tissue cut line.

Figure 6:
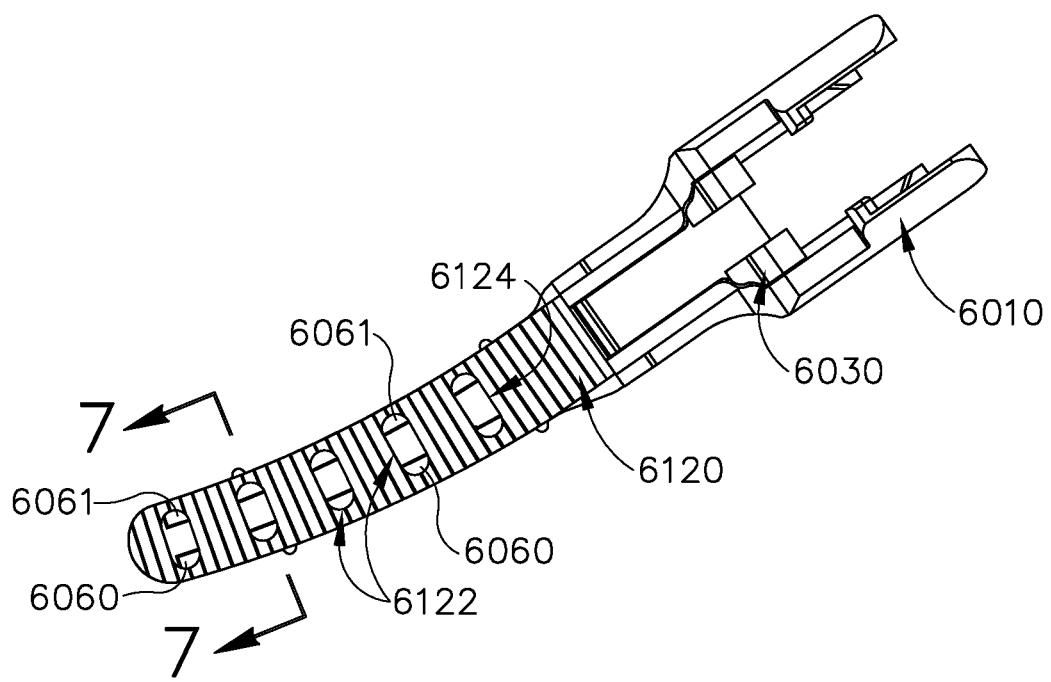
FIG. 6 depicts a bottom view of another exemplary clamp arras assembly of an end effector that may be incorporated into the instrument of FIG. 1.
Figure 7:
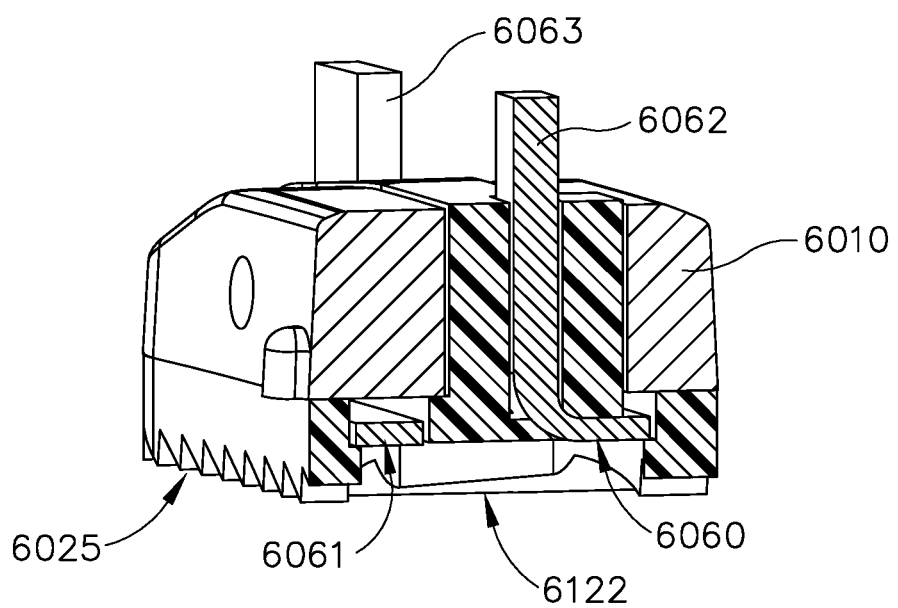
FIG. 7 depicts a perspective cross-sectional view of the clamp arm assembly of FIG. 6 taken along line 7-7 of FIG. 6.

Referring to FIGS. 6 and 7, in other versions, RF electrosurgical sealing is not required to be continuous along each side of the cut line, and instead may occur at multiple points along each side of the cut line in a discontinuous fashion. As shown in FIG. 6, clamp pad (6120) may replace clamp pad (6020). Clamp pad (6120) comprises transverse oval shaped openings (6122) as opposed to longitudinal slots (6022) of clamp pad (6020). Openings (6122) extend across centerline region (6124) of clamp pad (6120) such that centerline region (6124) of clamp pad (6120) is not continuous pad material along the length of centerline region (6124) as opposed to the configuration with clamp pad (6020) having continuous centerline region (6024).

In the example shown in FIGS. 6 and 7, ultrasonic energy may be provided to sever the tissue along a cut line that coincides with the aligned upper surface (252) of blade (240) and centerline region (6124) of clamp pad (6120). In the present configuration clamp pad (6120) contacts gripped tissue intermittently or in a discontinuous fashion because openings (6122) interrupt centerline region (6124). However, the spacing of openings (6122) and the ultrasonic energy applied are configured such that a continuous cut of the tissue is made over the length of clamp pad (6120) even without continuous contact between clamp pad (6120) and the tissue along centerline region (6124).

Openings (6122) in clamp pad (6120) provide access to or expose electrodes (6060, 6061). With this configuration, when the tissue is compressed between blade (240) and clamp pad (6120), the tissue can at least partially fill openings (6122) to contact electrodes (6060, 6061) at locations along the length of clamp pad (6120). In this manner, a conductive pathway is established through the tissue between electrodes (6060, 6061) and blade (240). With the tissue compressed between clamp pad (6120) and blade (240), ultrasonic energy can be imparted to waveguide (242) and thereby ultrasonically sever the tissue along the length of clamp pad (6120) as discussed above. On each side of the cut line, ultrasonic sealing occurs as described above. In addition, the end effector with clamp pad (6120) is further operable to provide RF electrosurgical sealing of tissue along the conductive pathways described above, which would include tissue that is laterally outward from the cut line formed between upper surface (252) of blade (240) and centerline region (6124) of clamp pad (6120). In some versions using openings (6122) the RF electrosurgical sealing occurs at those locations on each side of the cut line corresponding to the locations of respective openings (6122). In some versions, the spacing of openings (6122) is such that the RF electrosurgical sealing occurs not only at the openings (6122), but between openings (6122) as well. In this manner, RF electrosurgical sealing may be obtained along the length of clamp pad (6120) and thus along each side of the length of the tissue cut line. In view of the teachings herein, other configurations for openings (6122) to provide RF electrosurgical sealing will be apparent to those of ordinary skill in the art.

In the examples discussed above with respect to FIGS. 2-7, pairs of terminals (6062, 6063) connect to an electrical source such that each electrode (6060, 6061) has the same polarity, with blade (240) having the opposite polarity such that the conductive pathways exist between each of electrodes (6060, 6061) and blade (240). In other versions, blade (240) is electrically neutral and electrode (6060) has an opposite polarity to electrode (6061). In such examples with two oppositely polarized electrodes (6060, 6061) and a neutral blade (240), pairs of terminals (6062, 6063) connect to electrical sources such that one of electrodes (6060, 6061) has positive polarity and the other has negative polarity. With this configuration, the conductive pathways are established through the tissue between electrodes (6060, 6061). With these conductive pathways, the RF electrosurgical sealing occurs laterally across the tissue cut line. In versions using clamp pad (6020), the RF electrosurgical sealing may be continuous along the length of clamp pad (6020) and the tissue cut line. In versions using clamp pad (6120), the RF electrosurgical sealing may be discontinuous along the length of clamp pad (6120) and the tissue cut line. In view of the teachings herein, other ways to configure electrodes (6060, 6061) and clamp pads (6020, 6120) to achieve a desired conductive pathway for RF electrosurgical sealing will be apparent to those of ordinary skill in the art.

B. End Effector with Dual Electrode Molded within Clamp Pad

Figure 8A:
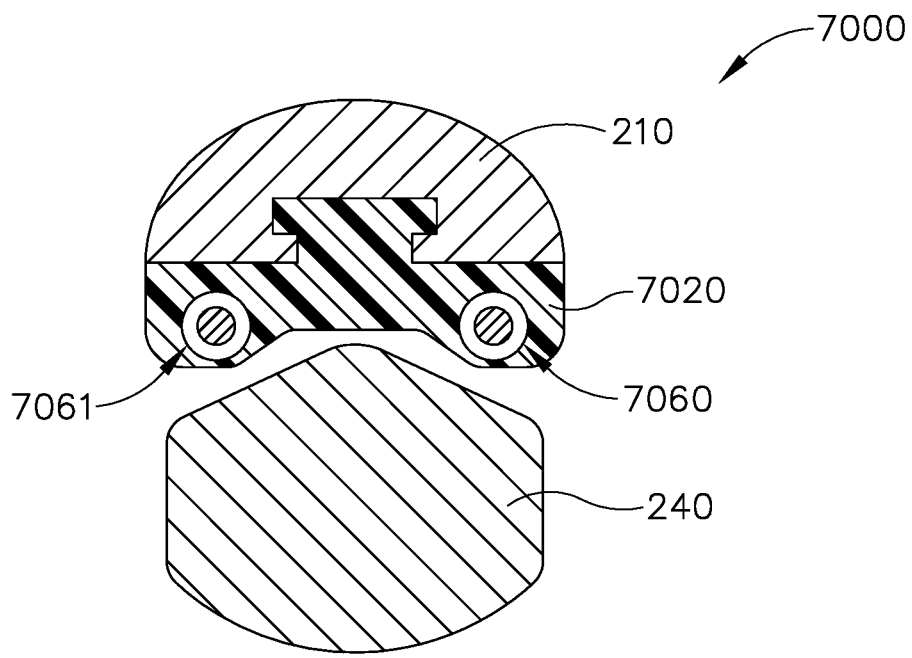
FIG. 8A depicts a cross-sectional view of another exemplary end effector that may be incorporated into the instrument of FIG. 1, with the cross-sectional view taken prior to machining.
Figure 8B:
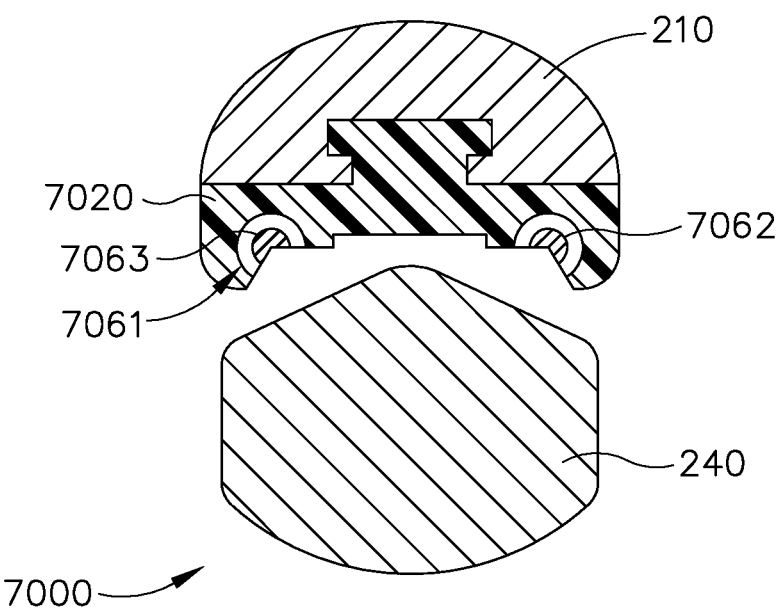
FIG. 8B depicts a cross-sectional view of the end effector of FIG. 8A taken after machining.

FIGS. 8A-9B show exemplary end effectors (7000, 7100) that may be readily incorporated into instrument (110) in place of end effector (140). FIGS. 8A and 8B show end effector (7000), which comprises clamp arm (210), a clamp pad (7020), blade (240), and first and second wires (7060, 7061). FIG. 8A shows a first state of manufacture for end effector (7000), prior to machining clamp pad (7020). FIG. 8B shows a second state of manufacture for end effector (7000), after machining clamp pad (7020) to expose electrodes (7062, 7063) within wires (7060, 7061), which have an insulating material surrounding electrodes (7062, 7063). In the present example, clamp pad (7020) is formed in a molding process such that clamp pad (7020) is formed with clamp arm (210) and molded over wires (7060, 7061). In other examples, clamp pad (7020) may be formed separate from clamp arm (210) and/or wires (7060, 7061) and then later combined with clamp arm (210) and/or wires (7060, 7061). After combining wires (7060, 7061), clamp pad (7020), and clamp arm (210), clamp pad (7020) is machined such that portions of clamp pad (7020) are cut away along with insulator portions of wires (7060, 7061) to expose electrodes (7062, 7063). In some instances, it is not necessary to combine clamp pad (7020) and wires (7060, 7061) with clamp arm prior to machining assembled clamp pad (7020) and wires (7060, 7061).

In the present example, each of wires (7060, 7061) have the same polarity with blade (240) having the opposite polarity. With identically polarized wires (7060, 7061) positioned opposite to oppositely polarized blade (240), this can be considered an opposing or offset electrode configuration. In some versions, wires (7060, 7061) each serve as a positive pole while blade (240) serves as a negative pole. In this configuration the conductive pathway is created through tissue between wires (7060, 7061) and blade (240). It should also be understood that, in some other versions, wires (7060, 7061) may have opposing polarity while blade (240) is electrically neutral.

Furthermore, as will be apparent to those of ordinary skill in the art in view of the teachings herein, the configuration of the machined cutouts, and the resulting openings created in clamp pad (7020) to expose electrodes (7062, 7063) will impact the configuration of the conductive pathways and the resulting RF electrosurgical sealing. By way of example only, and not limitation, clamp pad (7020) and wires (7060, 7061) may be machined such that there are continuous openings along clamp pad (7020) exposing electrodes (7062, 7063) in a continuous fashion along the length of clamp pad (7020). In other versions, clamp pad (7020) and wires (7060, 7061) may be machined such that there are intermittent openings along clamp pad (7020) exposing electrodes (7062, 7063) intermittently along the length of clamp pad (7020). In either approach, clamp pad (7020) and blade (240) are configured such that after machining clamp pad (7020), a sufficient gap is maintained between electrodes (7062, 7063) and blade (240) to prevent short circuiting as discussed above. In use, ultrasonic cutting, ultrasonic sealing, and RF electrosurgical sealing occur in the same or similar manner as described above and will be apparent to those of ordinary skill in the art in view of the teachings herein.

Figure 9A:
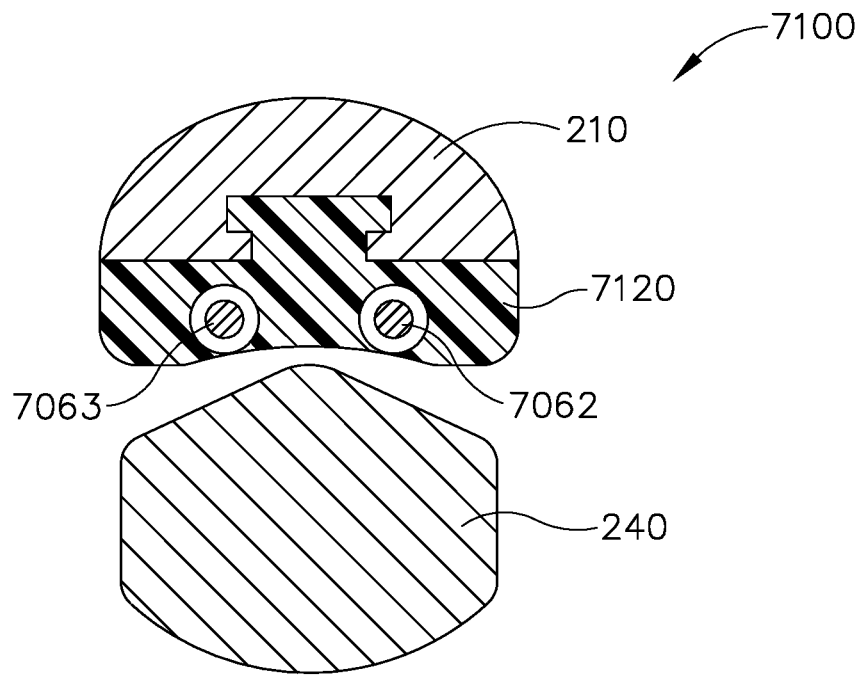
FIG. 9A depicts a cross-sectional view of another exemplary end effector that may be incorporated into the instrument of FIG. 1, with the cross-sectional view taken prior to machining.
Figure 9B:
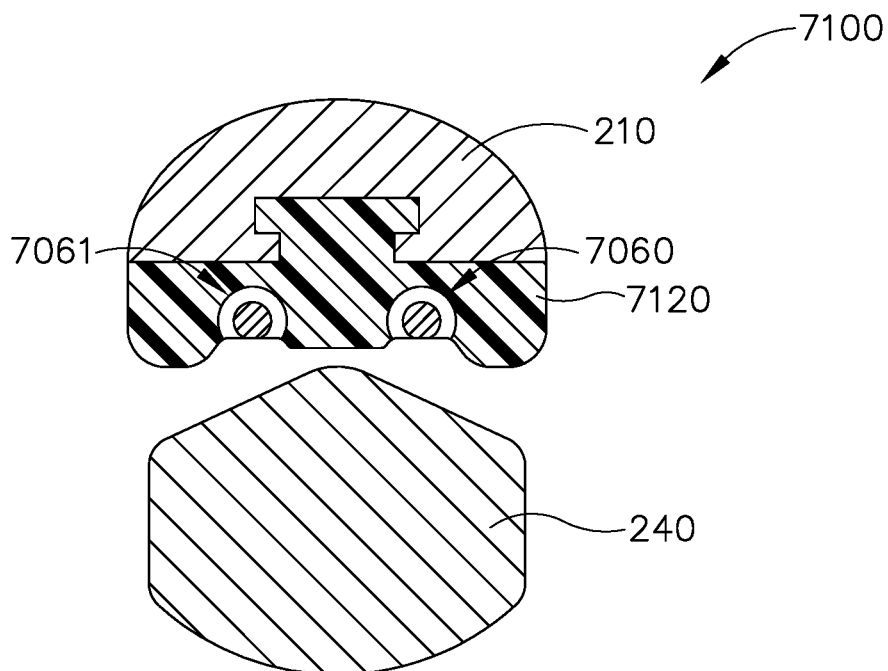
FIG. 9B depicts a cross-sectional view of the end effector of FIG. 8A taken after machining.
Figure 10:
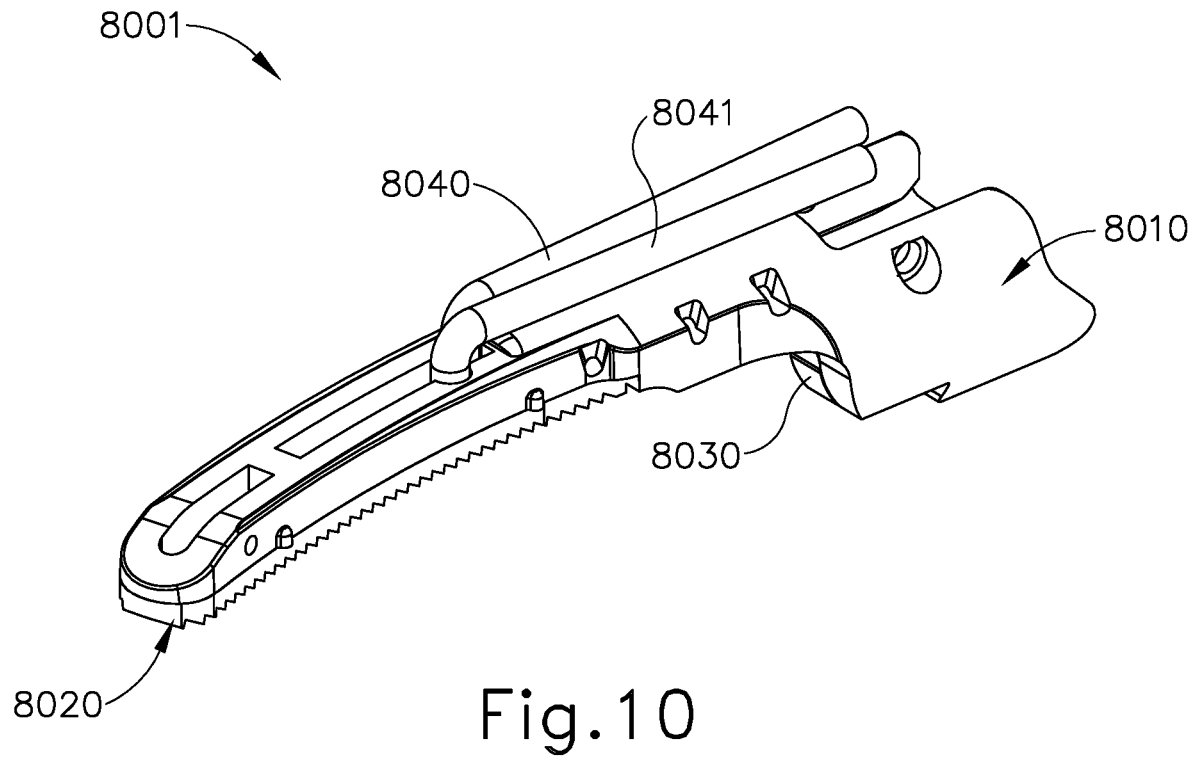
FIG. 10 depicts a perspective view of another exemplary clamp arm assembly of an end effector that may be incorporated into the instrument of FIG. 1.

FIGS. 9A and 9B show end effector (7100), which comprises clamp arm (210), a clamp pad (7120), blade (240), and first and second wires (7060, 7061). FIG. 9A shows a first state of manufacture for end effector (7100), prior to machining clamp pad (7120). FIG. 9B shows a second state of manufacture for end effector (7100), after machining clamp pad (7120) to expose electrodes (7062, 7063) within wires (7060, 7061), which have an insulating material surrounding electrodes (7062, 7063). In the present example, clamp pad (7120) is formed in a molding process such that clamp pad (7120) is formed with clamp arm (210) and molded over wires (7060, 7061). In other examples, clamp pad (7120) may be formed separate from clamp arm (210) and/or wires (7060, 7061) and then later combined with clamp arm (210) and/or wires (7060, 7061). After combining wires (7060, 7061), clamp pad (7120), and clamp arm (210), clamp pad (7120) is machined such that portions of clamp pad (7120) are cut away along with insulator portions of wires (7060, 7061) to expose electrodes (7062, 7063). In some instances, it is not necessary to combine clamp pad (7120) and wires (7060, 7061) with clamp arm (210) prior to machining assembled clamp pad (7120) and wires (7060, 7061).

In the present example, each wire (7060, 7061) has an opposite polarity with blade (240) being neutral. With oppositely polarized wires (7060, 7061) positioned offset from one another within clamp pad (7120), this can be considered an offset electrode configuration. In a configuration where wire (7060) serves as a positive pole and wire (7061) serves as a negative pole, the conductive pathway is created from electrode (7062) of wire (7060), through the gripped tissue, and to electrode (7063) of wire (7061). To facilitate this conductive pathway, wires (7060, 7061) are positioned closer together compared to the arrangement shown in FIGS. 8A and 8B. In view of the teachings herein, other positions for wires (7060, 7061) relative to clamp pad (7120) to achieve a desired conductive pathway through tissue will be apparent to those of ordinary skill in the art. It should also be understood that end effector (7100) may be modified such that electrodes (7062, 7063) both provide one pole (e.g., a positive pole) while blade (240) provides an opposite pole (e.g., a negative pole).

Furthermore, as will be apparent to those of ordinary skill in the art in view of the teachings herein, the configuration of the machined cutouts, and the resulting openings created in clamp pad (7120) to expose electrodes (7062, 7063) will impact the configuration of the conductive pathways and the resulting RF electrosurgical sealing. By way of example only, and not limitation, clamp pad (7120) and wires (7060, 7061) may be machined such that there are continuous openings along clamp pad (7120) exposing electrodes (7062, 7063) in a continuous fashion along the length of clamp pad (7120). In other versions, clamp pad (7120) and wires (7060, 7061) may be machined such that there are intermittent openings along clamp pad (7120) exposing electrodes (7062, 7063) intermittently along the length of clamp pad (7120). In either approach, although blade (240) is neutral, clamp pad (7120) and blade (240) may be configured such that after machining clamp pad (7120), a sufficient gap is maintained between electrodes (7062, 7063) and blade (240) to prevent short circuiting as discussed above. In use, ultrasonic cutting, ultrasonic sealing, and RF electrosurgical sealing occur in the same or similar manner as described above and will be apparent to those of ordinary skill in the art in view of the teachings herein. Furthermore, in some versions end effector (7100) may be configured such that electrodes (7062, 7063) have the same polarity and are used with blade (240) having an opposite polarity, similar to the description above with respect to end effector (7000).

C. End Effector with Dual Nested Electrode within Clamp Pad

FIGS. 10-15B show clamp assemblies (8001, 8101, 8201) of three other exemplary end effectors that may be readily incorporated into instrument (110) in place of end effector (140). Each end effector of these examples comprises the same clamp arm (8010), clamp pad retainer member (8030), wires (8040, 8041), insulators (8050, 8051), electrodes (8060, 8061), and blade (240). However, each end effector of these examples comprises a different configuration for clamp pads (8020, 8120, 8220) as will be described in greater detail below.

Referring to FIGS. 10 and 12-13B, the end effector of this example comprises a clamp arm assembly (8001). Clamp arm assembly (8001) is operable to pivot toward and away from blade (240) in the manner described above. Clamp arm assembly (8001) comprises clamp arm (8010), clamp pad (8020), clamp pad retainer member (8030), wires (8040, 8041), insulators (8050, 8051), and electrodes (8060, 8061). Clamp pad retainer member (8030) operates similar to clamp pad retainer member (230) discussed above. Clamp pad (8020) comprises openings (8021) that provide access to electrodes (8060, 8061). In the present example, openings (8021) are configured as rectangular shapes, where openings (8021) extend laterally across clamp pad (8020). This configuration provides for a centerline region (8027) of clamp pad (8020) with electrodes (8060, 8061) partially accessible or exposed. In the present example, blade (240) aligns along centerline region (8027) such that when tissue is compressed between blade (240) and clamp pad (8020), ultrasonic energy may be provided to sever the tissue along a cut line that coincides with the aligned upper surface (252) of blade (240) and centerline region (8027) of clamp pad (8020). In the present configuration clamp pad (8020) provides intermittent contact with the tissue along centerline region (8027) when the end effector is in a closed configuration gripping the tissue because openings (8021) interrupt centerline region (8027).

Figure 12:
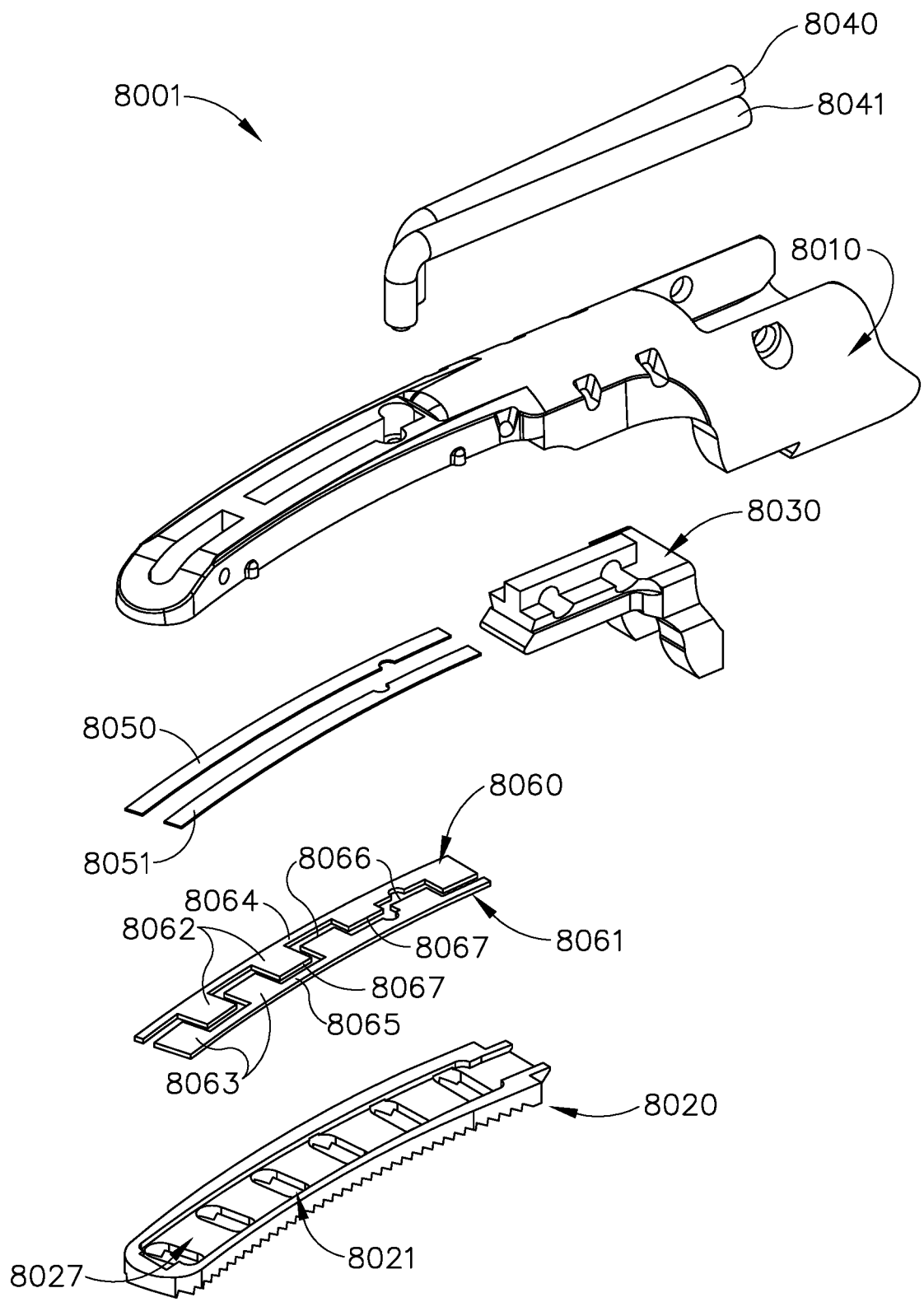
FIG. 12 depicts an exploded view of the clamp arm assembly of FIG. 10.
Figure 13A:
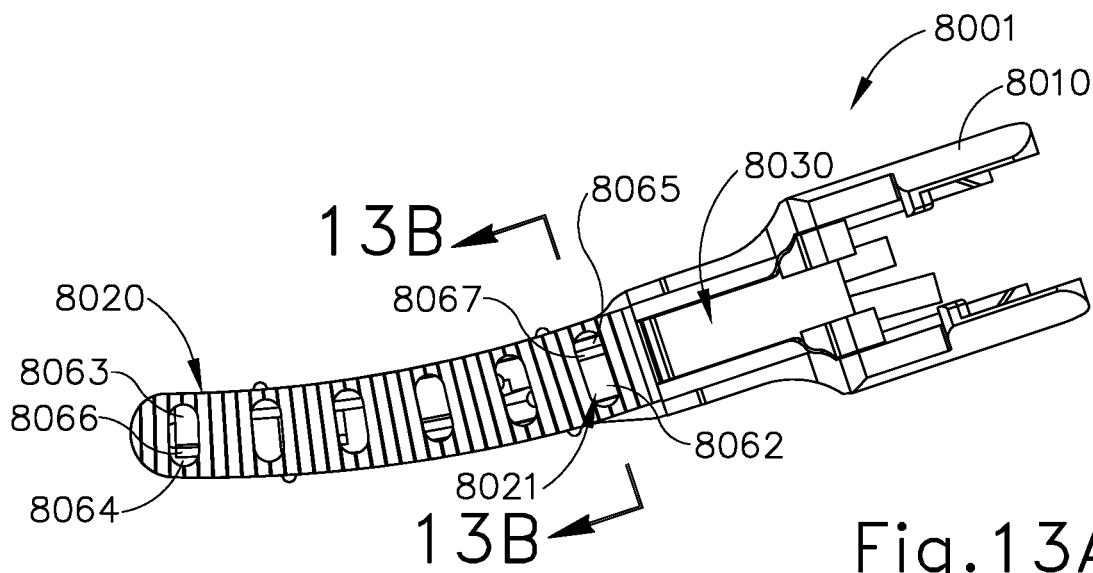
FIG. 13A depicts a bottom view of the clamp arm assembly of FIG. 10.

Openings (8021) in clamp pad (8020) provide access to or expose electrodes (8060, 8061). Electrodes (8060, 8061) each comprise projections (8062, 8063) that extend from respective body portions (8064, 8065) of electrodes (8060, 8061). Furthermore, electrodes (8060, 8061) each comprise spaces (8066, 8067) between respective projections (8062, 8063) of electrodes (8060, 8061). Projections (8062) and spaces (8066) are offset along the length of electrode (8060) relative to projections (8063) and spaces (8067) of electrode (8061). With this offset configuration, electrodes (8060, 8061) have a nested, interdigitated arrangement as best seen in FIG. 12, where projections (8062) are positionable within spaces (8067), and projections (8063) are positionable within spaces (8066). As seen in FIG. 12, although nested, electrodes (8060, 8061) maintain a space or gap from one another such that they are not in contact. Electrodes (8060,

8061) are connectable with wires (8040, 8041) such that electrodes (8060, 8061) can serve as positive and negative poles. While wires (8040, 8041) are shown as being exposed above clamp arm (8010) in FIGS. 10-12, 13B, 14B, and 15B, it should be understood that this is an exaggerated representation of wires (8040, 8041). In practical contexts, wires (8040, 8041) may in fact be disposed in clamp pad (8020) and retainer member (8030) such that wires (8040, 8041) are not exposed above clamp arm (8010).

Insulators (8050, 8051) are positioned between clamp arm (8010) and electrodes (8060, 8061) such that clamp arm (8010) remains electrically neutral. In the present example, blade (240) can be coated such that blade (240) remains electrically neutral also. The coating used with blade (240) can also provide non-stick features that help prevent tissue from sticking to blade (240).

With this configuration, when the tissue is compressed between blade (240) and clamp pad (8020), the tissue can at least partially fill openings (8021) to contact electrodes (8060, 8061) at locations along the length of clamp pad (8020). Moreover, at least some of the tissue that fills openings (8021) can at least partially fill spaces (8066, 8067) between electrodes (8060, 8061). In this manner, a conductive pathway is established through the tissue between electrodes (8060, 8061). With the tissue compressed between clamp pad (8020) and blade (240), ultrasonic energy can be imparted to waveguide (242) and thereby ultrasonically sever the tissue along the length of clamp pad (8020) as discussed above. On each side of the cut line, ultrasonic sealing occurs as described above. In addition, the end effector is further operable to provide RF electrosurgical sealing of the tissue along the conductive pathways described above, which would include RF electrosurgical sealing through tissue from one side of the cut line to tissue on the other side of the cut line since the cut line is generally centered along the nested area of electrodes (8060, 8061). In some versions, the spacing of openings (8021) is such that the RF electrosurgical sealing occurs not only at the openings (8021), but between openings (8021) as well. In this manner, RF electrosurgical sealing may be obtained along the entire length of clamp pad (8020) and thus the entire length of the tissue cut line. In other versions, RF electrosurgical sealing is not required to be continuous along the cut line, and instead may occur at multiple points along the cut line in a discontinuous fashion as described above.

In some other versions using an end effector as configured as shown in FIGS. 10 and 12-13B, the end effector may be modified such that each electrode (8060, 8061) has the same polarity and with the blade (240) having the opposite polarity from the electrodes (8060, 8061). In this configuration, and where the electrodes (8060, 8061) serve as positive poles and blade (240) serves as the negative pole, the conductive path will extend from each of the electrodes (8060, 8061), through the tissue, and to the blade (240). As will be understood by those of ordinary skill in the art in view of the teachings herein, the RF electrosurgical sealing will then occur as described above with respect to those versions using a polarized blade.

Figure 11:
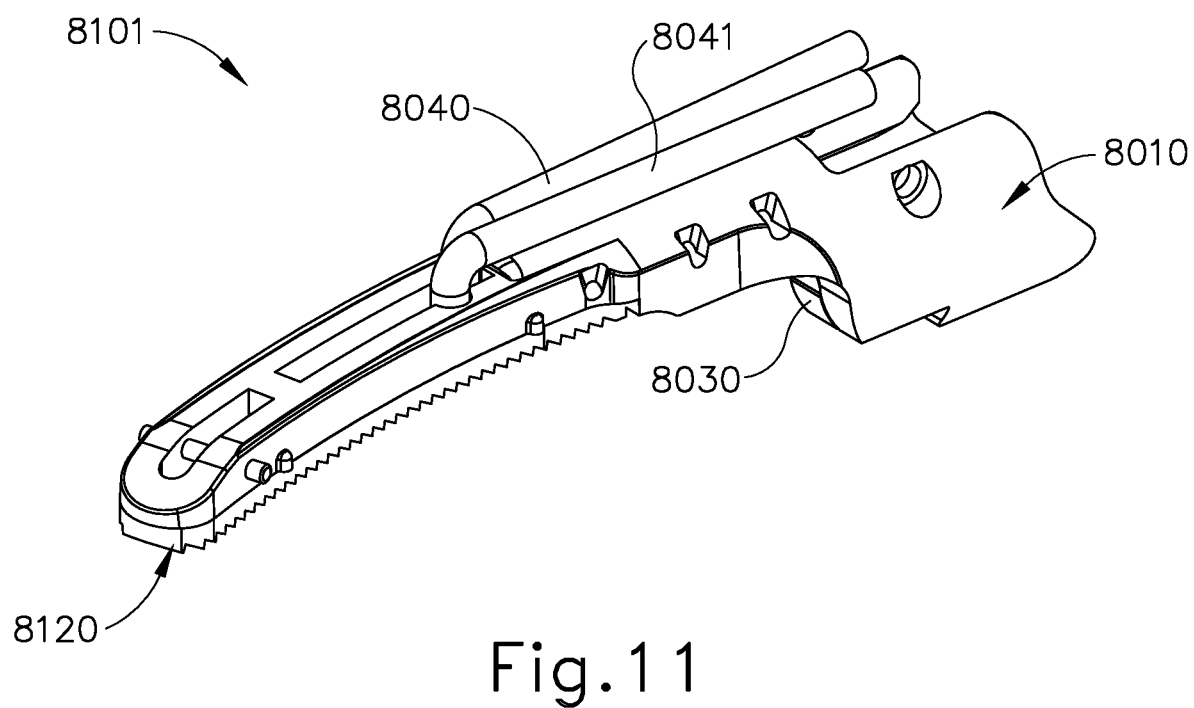
FIG. 11 depicts a perspective view of another exemplary clamp arm assembly of an end effector that may be incorporated into the instrument of FIG. 1.
Figure 14A:
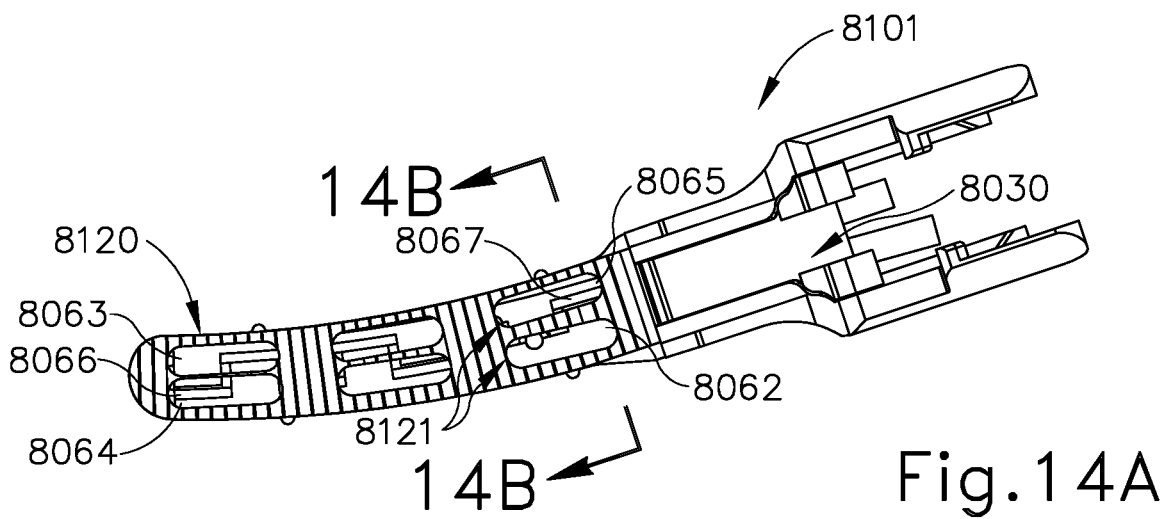
FIG. 14A depicts a bottom view of another exemplary clamp arm assembly of an end effector that may be incorporated into the instrument of FIG. 1.
Figure 14B:
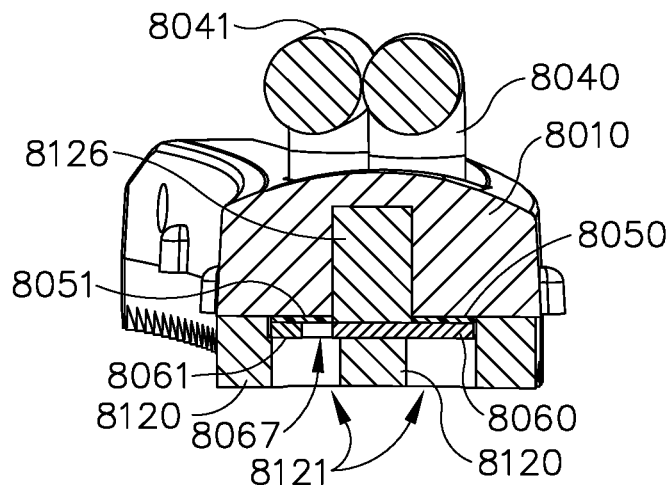
FIG. 14B depicts a perspective cross-sectional view of the clamp arm assembly of FIG. 14A, taken along line 14B-14B of FIG. 14A.

FIGS. 11, 14A, and 14B show a similar end effector that uses clamp arm assembly (8101), which incorporates clamp pad (8120). As mentioned above, clamp arm assembly (8101) includes many of the same components and operates similarly to clamp arm assembly (8001) described above. One difference is with clamp arm assembly (8101), clamp pad (8120) is formed with a rail (8126) for engaging with clamp arm (8010). Rail (8126) is structurally and operably similar to rail (226) described above. Another difference with clamp arm assembly (8101) is that clamp pad (8120) comprises openings (8121) that are shaped as pairs of longitudinally elongated circles that repeat along the length of clamp pad (8120), With this alternate opening configuration for clamp pad (8120), the pattern of the RF electrosurgical sealing may differ from that described above with respect to clamp pad (8020) and openings (8021). As described above, this end effector using clamp arm assembly (8101) may be configured such that an electrically neutral blade (240) is used with oppositely polarized electrodes (8060, 8061); or in other versions each electrode (8060, 8061) may have the same polarity, with blade (240) being oppositely polarized. The gap between openings (8121) may vary to ensure there is material to engage blade (240) for the ultrasonic functionality. For instance, distal openings (8121) may be smaller out at the tapered end of clamp arm (8010). Alternatively, blade (240) may be reconfigured to contact outside of the centerline to allow a cut along the entire length of clamp arm (8010).

Figure 15A:
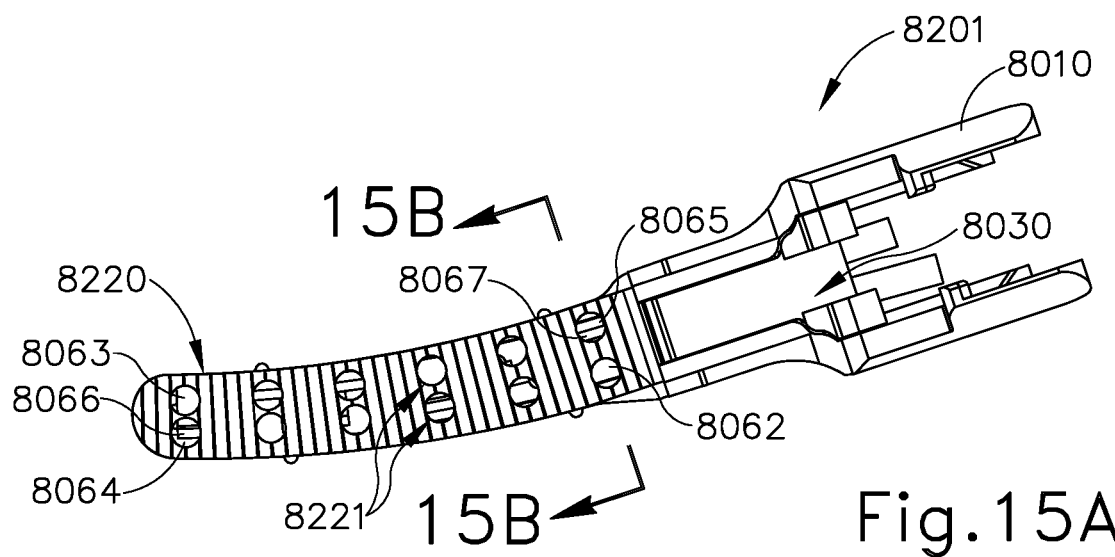
FIG. 15A depicts a bottom view of another exemplary clamp arm assembly of an end effector that may be incorporated into the instrument of FIG. 1.
Figure 13B:
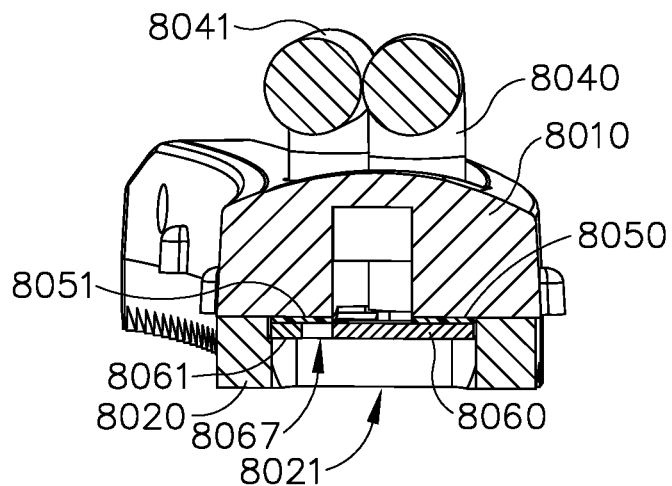
FIG. 13B depicts a perspective cross-sectional view of the clamp arm assembly of FIG. 13A, taken along line 13B-13B of FIG. 13A.
Figure 15B:
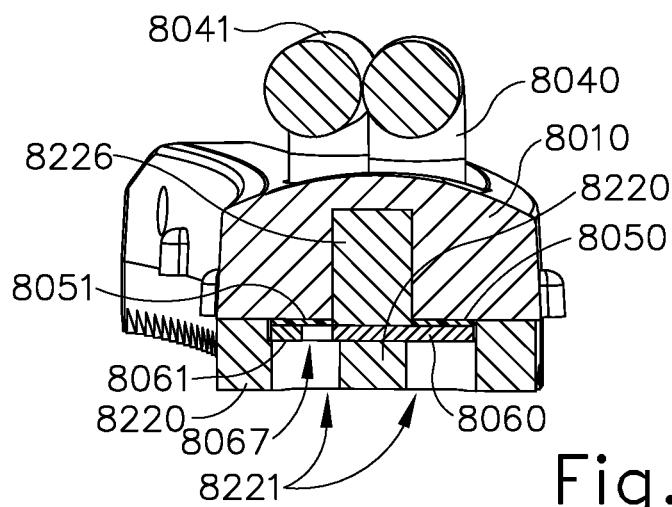
FIG. 15B depicts a perspective cross-sectional view of the clamp arm assembly of FIG. 15A, taken along line 15B-15B of FIG. 15A.
Figure 16:
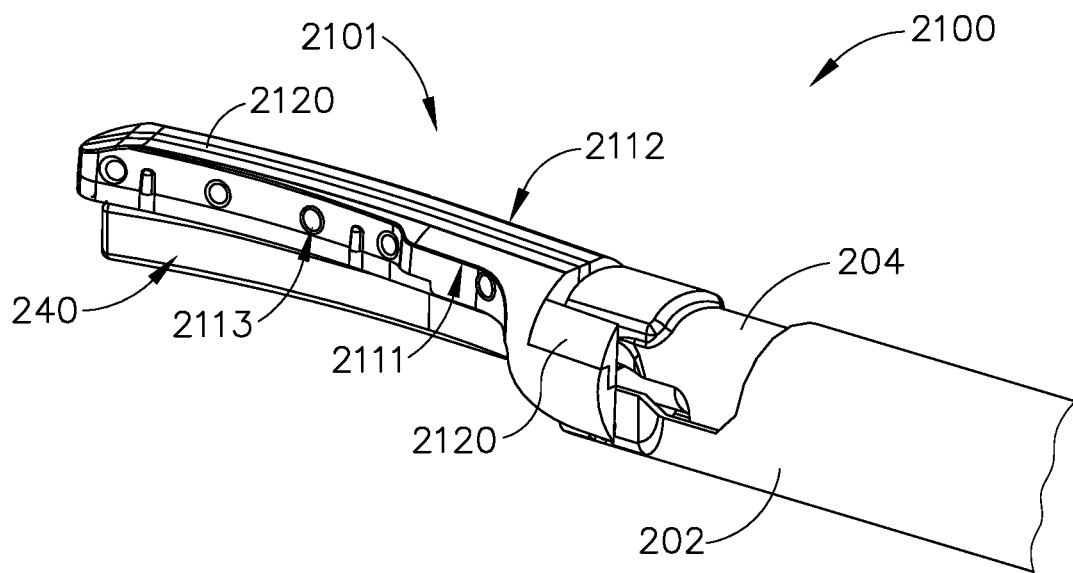
FIG. 16 depicts a perspective view of another exemplary end effector that may be incorporated into the instrument of FIG. 1, with the end effector in a closed configuration.
Figure 17:
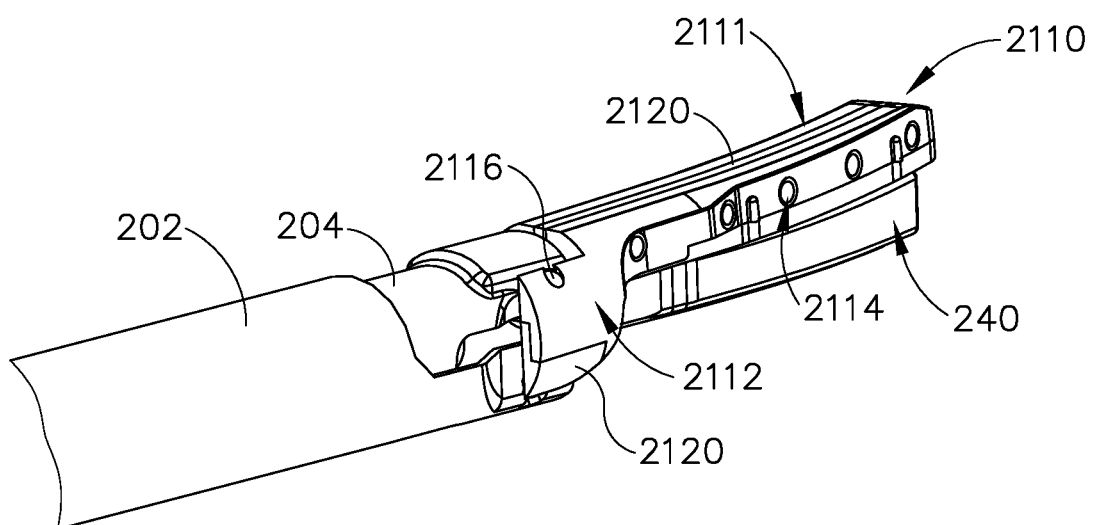
FIG. 17 depicts another perspective view of the end effector of FIG. 16.
Figure 18:
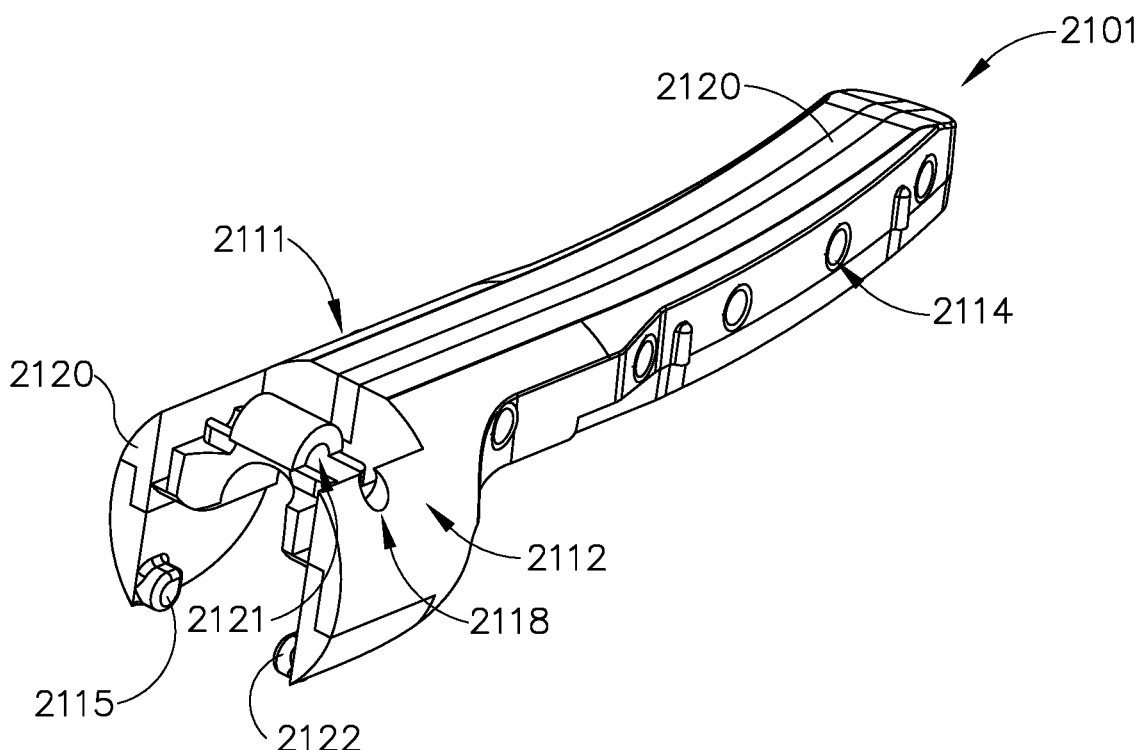
FIG. 18 depicts a perspective view of the clamp arm assembly of FIG. 16.

FIGS. 15A and 15B show a similar end effector that uses clamp arm assembly (8201), which incorporates clamp pad (8220). As mentioned above, clamp arm assembly (8201) includes many of the same components and operates similarly to clamp arm assembly (8001) described above. One difference with clamp arm assembly (8201) is that clamp pad (8220) is formed with a rail (8226) for engaging with clamp arm (8010). Rail (8226) is structurally and operably similar to rail (226) described above. Another difference with clamp arm assembly (8201) is that clamp pad (8220) comprises openings (8221) that are shaped as pairs of circles that repeat along the length of clamp pad (8220). With this alternate opening configuration for clamp pad (8220), the pattern of the RF electrosurgical sealing may differ from that described above with respect to clamp pad (8020) and openings (8021). As described above, this end effector using clamp arm assembly (8201) may be configured such that an electrically neutral blade (240) is used with oppositely polarized electrodes (8060, 8061); or in other versions each electrode (8060, 8061) may have the same polarity with blade (240) being oppositely polarized.

While the above version illustrate electrodes (8060, 8061) as flat conductors, such as stamped metal, etc., in some other versions electrodes (8060, 8061) can be wire structures. For example, a pair of wires may be configured in a close nested arrangement, similar to the nested arrangement shown for electrodes (8060, 8061) in FIG. 12. The wires may then have opposite polarity and be used with a neutral blade (240) or the wires may have the same polarity and be used with an oppositely polarized blade (240) as described above. In view of the teachings herein, other nested structures and arrangements for electrodes (8060, 8061) will be apparent to those of ordinary skill in the art.

D. End Effector with Split Clamp Arm Electrodes

FIGS. 16-20B show another exemplary end effector (2100) that may be readily incorporated into instrument (110) in place of end effector (140). End effector (2100) comprises a clamp arm (2110), blade (240), and a pad (2120). Clamp arm (2110) has a split configuration where clamp arm (2110) comprises a first body (2111) and a second body (2112). As will be discussed further below, first body (2111) and second body (2112) each have opposite polarity and serve as electrodes for RF electrosurgical sealing.

Figure 19:
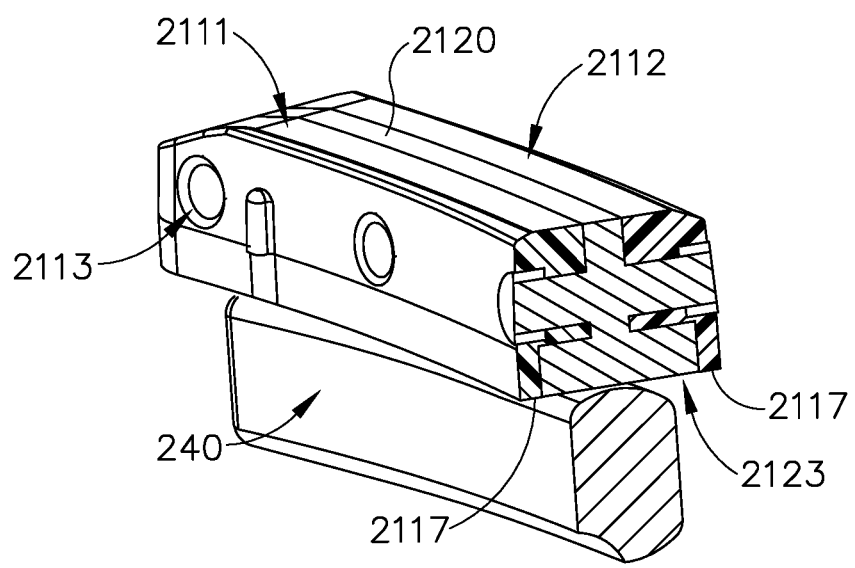
FIG. 19 depicts a perspective cross-sectional view of the end effector of FIG. 16.
Figure 20A:
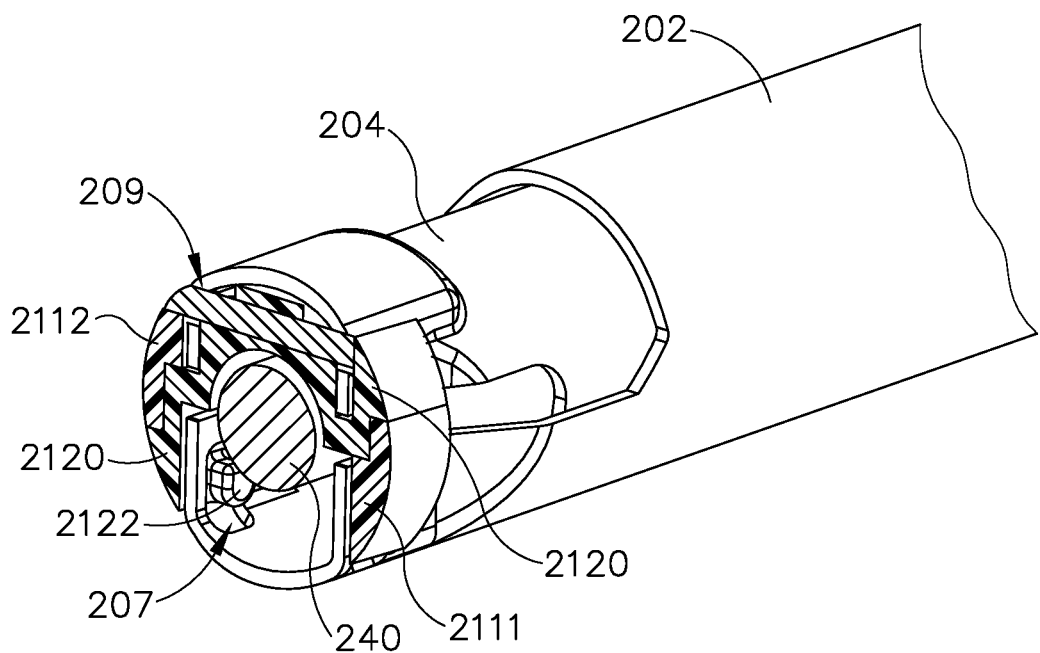
FIG. 20A depicts another perspective cross-sectional view of the end effector of FIG. 16.
Figure 20B:
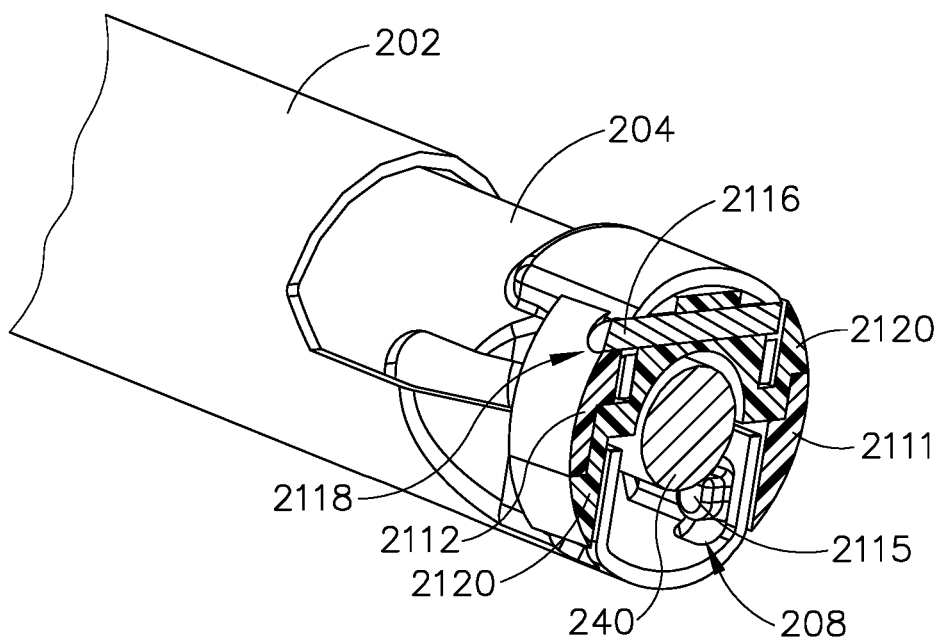
FIG. 20B depicts another perspective cross-sectional view of the end effector of FIG. 16.

Positioned between first body (2111) and second body (2112) of clamp arm (2110) is an electrically insulating clamp pad (2120). In the present example, clamp pad (2120) is molded and formed between first and second bodies (2111, 2112). First body (2111) comprises bores (2113) that are configured to receive portions of molded clamp pad (2120) to secure clamp pad (2120) with first body (2111). Similarly, second body (2112) comprises bores (2114) that are also configured to receive portions of molded clamp pad (2120) to secure clamp pad (2120) with first body (2111). As shown in FIG. 19, molded clamp pad (2120) extends within bores (2113, 2114), connecting first body (2111) and second body (2112) together. Collectively, first body (2111), second body (2112), and clamp pad (2120) make up clamp arm assembly (2101). While the present example shows bores (2113) and bores (2114) generally aligned across from each other, such alignment is not required in all versions. In assembling clamp arm (2110), clamp pad (2120) is formed between first body (2111) and second body (2112) such that first body (2111) and second body (2112) do not directly contact one another. In this manner, with first body (2111) oppositely polarized from second body (2112), short circuits can be avoided. In view of the teachings herein, other ways to configure clamp arm (2110) and clamp pad (2120) to achieve a multi part clamp arm that provides both positive and negative polarity will be apparent to those of ordinary skill in the art.

In the present example, clamp arm assembly (2101) connects with inner tube (204) and outer tube (202). Clamp arm assembly (2101) is operable to open and close to grip tissue in the same manner to that described above with respect to end effector (200). In the present example, first body (2111) makes connects with outer tube (202) by way of a post (2115) engaging an opening (208) in outer tube (202). Post (2115) is directly formed as part of first body (2111) such that post (2115) provides a path for electrical communication between outer tube (202) and first body (2111). Second body (2112) connects with inner tube (204) by way of a pin (2116) engaging an opening (209) in inner tube (204). Pin (2116) extends through an opening (2118) in second body (2112), which aligns with opening (209) in inner tube (204). Pin (2116) is comprised of a conductive material such that pin (2116) provides a path for electrical communication between inner tube (204) and second body (2112).

To provide electrical isolation between outer tube (202) and inner tube (204), first body (2111) does not directly connect with inner tube (204). Instead, pin (2116) extends through a molded bore (2121) in clamp pad (2120), which is securely attached with first body (2111) as described above. Similarly, second body (2112) does not directly connect with outer tube (202), but instead clamp pad (2120) is formed with a post (2122) that engages an opening (207) in outer tube (202). With this configuration, clamp arm assembly (2101) has a pivoting connection with inner tube (204) as well as a pivoting connection with outer tube (202) such that clamp arm assembly (2101) is operable to open and close in response to translating movement of outer and/or inner tubes (202, 204) as described above. Moreover, clamp arm assembly (2101) is operable to open and close while maintaining two sides of clamp arm (2110) having opposite polarity. In view of the teachings herein, other ways to connect clamp arm assembly (2101) with inner and outer tubes (204, 202) for open/close operability, while maintaining the polarity configuration descried above, will be apparent to those of ordinary skill in the art.

Referring to FIG. 19, with its split configuration, clamp arm (2110) includes a split U-shaped electrode surface (2117) formed by first and second bodies (2111, 2112). Clamp pad (2120) includes a plurality of teeth (2123) that assist in gripping tissue that is clamped between clamp arm (2110) and blade (240). Electrode surface (2117) extends around clamp arm (2110), surrounding the outer perimeter of clamp pad (2120) except where clamp pad (2120) separates first body (2111) from second body (2112) at the distal-most end of clamp arm (2110). In the present example, electrode surface (2117) is flush with the ridges of teeth (2123), such that valleys of teeth (2123) are recessed relative to electrode surface (2117). In some alternative versions, the ridges of teeth (2123) are recessed relative to electrode surface (2117). In some other alternative versions, the ridges of teeth (2123) are proud relative to electrode surface (2117), such that electrode surface is recessed relative to the ridges of teeth (2123). Other suitable relationships will be apparent to those of ordinary skill in the art in view of the teachings herein.

End effector (2100) may capture a single layer of tissue or two or more layers of tissue may be captured in some examples. As similarly described above with respect to end effector (200), the compression forces on the tissue with end effector (2100) are focused in the region between upper contact surface (252) of blade (240) and clamp pad (2120). These compression forces are directed mainly along the same vertical plane along which clamp arm (2110) pivots toward blade (240). The tissue is also contacted by oblique surfaces (254) of blade (240). However, the compression provided by oblique surfaces (254) is lower than the compression provided by upper contact surface (252). Moreover, the compression forces imposed on the tissue by oblique surfaces (254) are directed obliquely outwardly, mainly toward electrode surface (2117). It should be understood that the above-described manner in which end effector (2100) engages tissue may provide ultrasonic severing of tissue in the region between upper contact surface (252) and clamp pad (2120), with combined ultrasonic sealing of tissue in the regions between oblique surfaces (254) and clamp pad (2120) and/or electrode surface (2117).

Additionally, with oppositely polarized first body (2111) and second body (2112) of clamp arm (2110), when end effector (2100) captures tissue in a closed configuration, a conductive pathway is created between the positive pole of e.g. first body (2111), laterally through the captured tissue, and the negative pole of e.g. second body (2112). Of course in other versions the polarity of first and second bodies (2111, 2112) may be switched such that the conductive pathway would be similar but flow from second body (2112), through the tissue, and to first body (2111). In the present example, RF electrosurgical sealing occurs along the conductive pathway described above, which includes RF electrosurgical sealing laterally through the compresses tissue along and across the cut line of the tissue. In this example, blade (240) may be neutral or blade (240) may be electrically conductive.

E. End Effector with Clamp Pad Flow Control

FIGS. 1-23 show other exemplary end effectors (2800, 2900) that may be readily incorporated into instrument (110) in place of end effector (140). End effectors (2800, 2900) include clamp pads and clamp arms. There may be concern that, as the clamp pad material wears, there will be need to be a path for the clamp pad material to flow. Thus, the clamp pads of the following examples include features that guide flow of the clamp pad material when degradation occurs so that this clamp pad flow will not interfere with the consistent gap desired between electrode poles of respective end effectors (2800, 2900). A consistent gap between electrode poles promotes consistent RF electrosurgical sealing.

Figure 21:
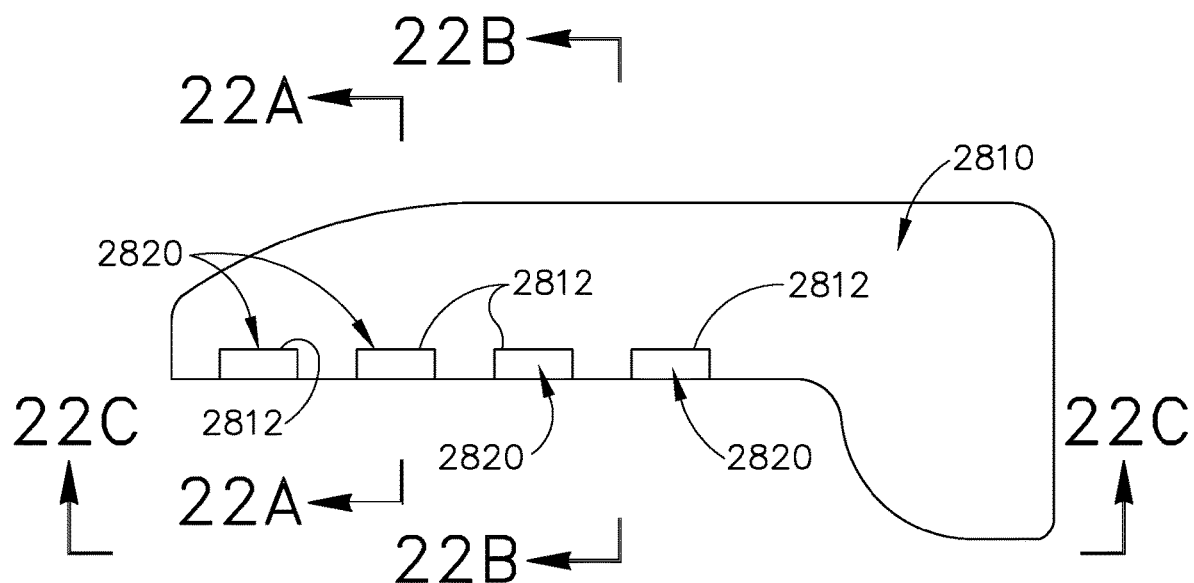
FIG. 21 depicts a side view of another exemplary end effector, shown without the blade, that may be incorporated into the instrument of FIG. 1.
Figures 22A, 22B:
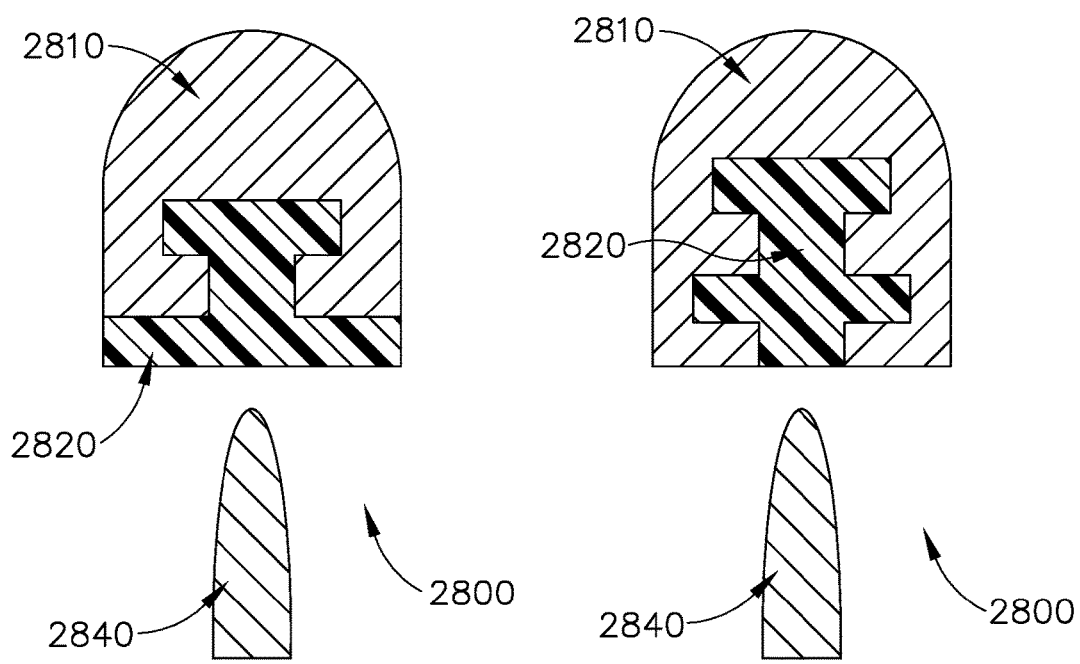
FIG. 22A depicts a cross-section view of the end effector of FIG. 21 taken along line 22A-22A of FIG. 21.
FIG. 22B depicts a cross-section view of the end effector of FIG. 21 taken along line 22B-22B of FIG. 21.
Figure 22C:
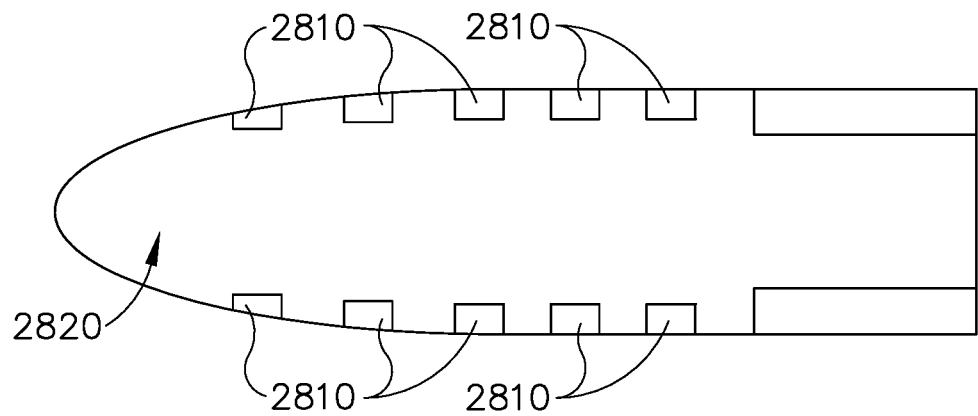
FIG. 22C depicts a bottom view of the end effector of FIG. 21 taken along line 22C-22C of FIG. 21.

Referring to FIGS. 21-22C, end effector (2800) comprises clamp arm (2810), clamp pad (2820), and blade (2840). In the present example, blade (2840) has serves as a negative pole and thereby serves as one of the electrodes for RF electrosurgical sealing. Furthermore, clamp arm (2810) serves as a positive pole and thereby serves as the other electrode for RF electrosurgical sealing. End effector (2800) is configured initially with a desired gap between the electrodes—in the present example, between blade (2840) and clamp arm (2810). Similarly to previously described end effector versions, end effector (2800) is operable to capture, ultrasonically sever, ultrasonically seal, and RF electrosurgical seal tissue that is compressed between blade (2840) and clamp pad (2820). These processes can create a heat build-up that can deform clamp pad (2820). This deformation can cause clamp pad (2820) to flow outwardly away from areas of compression with blade (2820). Deformed portions of clamp pad (2820), can move out laterally where there are not electrodes protruding downwardly from clamp arm (2810). This deformation, flow, and deposit of clamp pad material can alter the desired initial gap between the electrodes—in the present example, between blade (2840) and clamp arm (2810).

With end effector (2800), clamp arm (2810) comprises electrodes (2812) along its perimeter such that clamp arm (2810) has a castellated appearance as shown in FIG. 21. Clamp pad (2820) is formed within electrodes (2812) of clamp arm (2810) as seen by comparing the cross-section views of FIGS. 22A and 22B. With this configuration, when clamp pad (2820) degrades and begins to flow, the clamp pad material can flow outwardly between electrodes (2812) in clamp arm (2810) since clamp pad (2820) is not completely bound by clamp arm (2812). This outward flow of degraded clamp pad material prevents such degraded clamp material from depositing on tissue-contacting surfaces of clamp arm (2810), or other tissue contacting surfaces of clamp pad (2820). In this manner a constant gap is maintained between conductive blade (2840) and conductive clamp arm (2810) along those portions of clamp arm (2810) having a conductive pathway from clamp arm (2810), through captured tissue, and to blade (2840), as shown in FIG. 22B.

Figure 23:
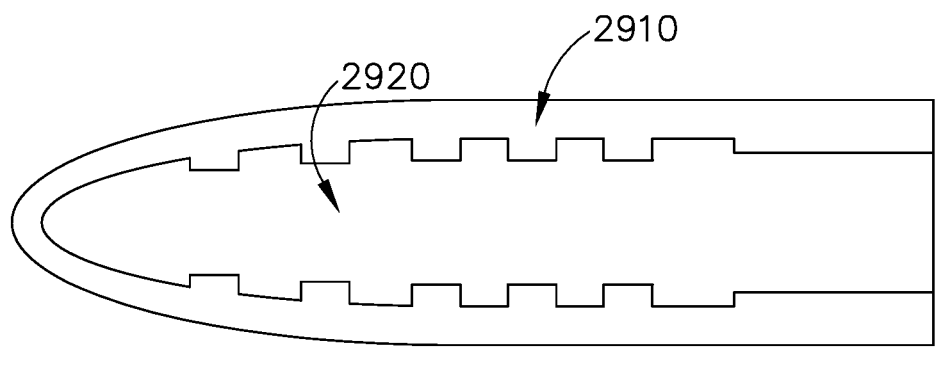
FIG. 23 depicts a bottom view of another exemplary end effector, shown without the blade, that may be incorporated into the instrument of FIG. 1.

FIG. 23 shows an alternate clamp arm (2900) having an electrode (2910) and clamp pad (2920) configured to provide pad material flow control similarly as described above. In this example, electrode (2910) is continuous around the perimeter of clamp arm (2900) and extends inwardly toward the center line along the length of clamp arm (2900). The body of clamp arm (2900) defines recesses or chambers into which the material of clamp pad (2920) may flow as clamp pad (2920) degrades. Such recesses or chambers may be located above electrodes (2910) (i.e., further into the page in the view of FIG. 23), such that as the material of clamp pad (2920) degrades and is pushed upwardly, the material will not flow out over clamp arm (2900) and thereby block electrode (2910) from maintaining electrical continuity with the tissue.

In view of the teachings herein, other ways to configure clamp arms and clamp pads to provide for flow control of degraded clamp pad material will be apparent to those of ordinary skill in the art.

F. End Effector with Conductive Pad and Clamp Arm

Figure 24:
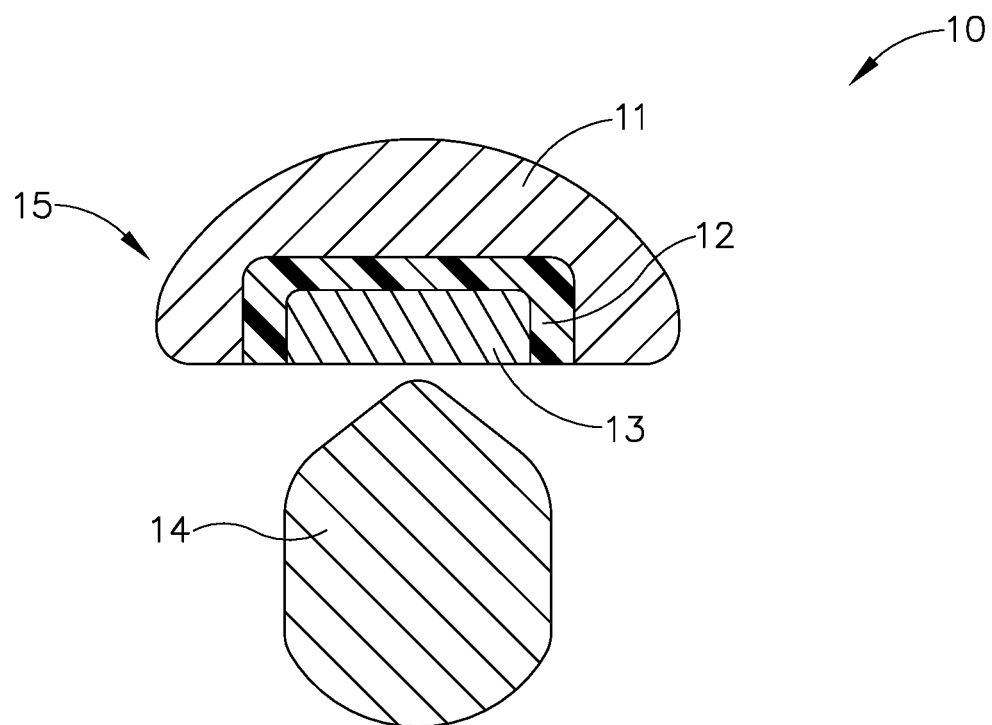
FIG. 24 depicts a cross-section view of another exemplary end effector that may be incorporated into the instrument of FIG. 1, with the end effector in a closed configuration.
Figure 25:
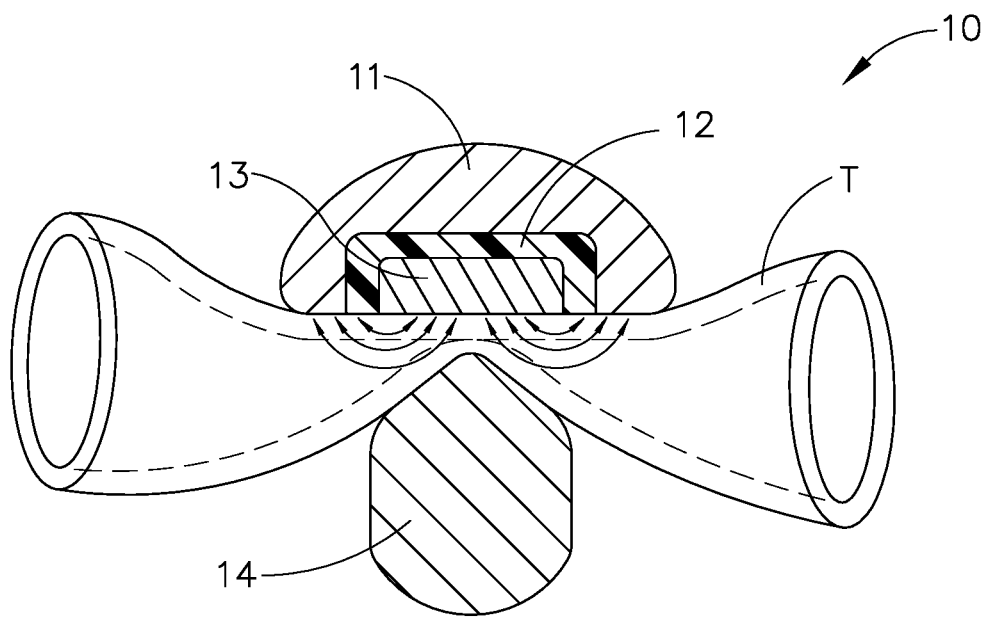
FIG. 25 depicts an end view of the end effector of FIG. 24, with the end effector compressing tissue between the clamp arm and the ultrasonic blade.

FIGS. 24-25 show another exemplary end effector (10) that may be readily incorporated into instrument (110) in place of end effector (140). End effector (10) is configured such that a single treatment region can be defined for both ultrasonic cutting and electrosurgical sealing. End effector (10) of this example comprises an ultrasonic blade (14) and a clamp arm assembly (15). Clamp arm assembly (15) comprises a clamp arm (11), an insulator (12), and a clamp pad (13). Clamp arm (11) connects with inner tube (204) via pin (205) and is operable to pivot toward and away from blade (14) in the manner described above. In this way, instrument (110) is operable to provide ultrasonic cutting when tissue is compressed between blade (14) and clamp arm assembly (15), and blade (14) is activated to oscillate ultrasonically as described further herein.

End effector (10) also provides electrosurgical sealing by delivering electrosurgical energy from one electrical pole to another. In the present example, clamp pad (13) comprises one of the electrical poles while clamp arm (11) comprises the other of the electrical poles. In this manner both clamp pad (13) and clamp arm (11) are conductive and thereby configured to apply electrical energy, with clamp pad (13) having an opposite polarity to that of clamp arm (11). In some versions of end effector (10), clamp pad (13) comprises a custom formulated pad having metallic alloy particles that are electrically activated. In some other versions, clamp pad (13) may be formulated with carbon particles, graphene, and/or other conductive fillers instead of or in addition to metallic alloy particles. Still in other versions, clamp pad (13) may comprises a positive temperature coefficient (PTC) material, which is both conductive and temperature reactive. In view of the teachings herein, other materials and ways to configure clamp pad (13) such that clamp pad (13) is electrically conductive will be apparent to those of ordinary skill in the art. Conductive clamp pad (13) connects with an electrical source, such as generator (116), via a cable or other electrical pathway to electrically activate clamp pad (13).

Clamp arm (11) is also formed of a conductive material as mentioned above. In the present example, clamp arm (11) is coated with an insulating material on its outer surface, which faces away from clamped tissue. The inner surface of clamp arm (11), which faces the clamped tissue, is not coated with an insulating material such that the clamped tissue is exposed to the electrically conductive surface of clamp arm (11) when end effector (10) is providing electrosurgical sealing. Conductive clamp arm (11) connects with an electrical source, such as generator (116), via a cable or other electrical pathway to provide electrical polarity to clamp arm (11). In the present example, clamp arm (11) is isolated from clamp pad (13) by way of insulator (12). This isolation using insulator (12) is configured so that any flow of electrical energy from clamp pad (13) to clamp arm (11), or vice versa, when clamping tissue, must be by the electrical energy flowing through the clamped tissue.

In the present example, blade (14) comprises a coating on at least a portion of blade (14) such that in the region for ultrasonic cutting and RF electrosurgical sealing blade (14) is electrically isolated from electrically activated clamp arm (11) and clamp pad (13). In some versions, the coating used on blade (14) may comprises parylene, xylan, or other suitable coatings that electrically isolate blade (14) from the RF circuit.

During cutting and sealing, clamp arm assembly (15) is actuated to the closed position such that tissue (T) is compressed between clamp arm assembly (15) and blade (14) as shown in FIG. 25. To provide ultrasonic cutting, vibrational energy is applied to blade (14), which oscillates ultrasonically to sever clamped tissue (T) at the region where tissue (T) is compressed between blade (14) and clamp pad (13). To provide RF electrosurgical sealing, with tissue (T) in the clamped and compressed state, RF electrosurgical energy is provided from an electrical source, such as generator (116). The electrical current travels from the positive pole though the tissue (T) and to the negative pole.

In the present example, clamp pad (13) comprises the positive pole and clamp arm (11) comprises the negative pole. However, in other versions these poles may be reversed. Cutting and sealing operations may be performed in any order or simultaneously. In some instances, only one of the treatment modalities (ultrasonic cutting being one modality and electrosurgical sealing being another) may be used with end effector (10). Where both cutting and sealing modalities are used for a portion of clamped tissue (T), as best understood from FIG. 25, electrosurgical sealing occurs along both sides of the cut line, such that both of the cut ends of the tissue (T) are sealed.

Figure 26:
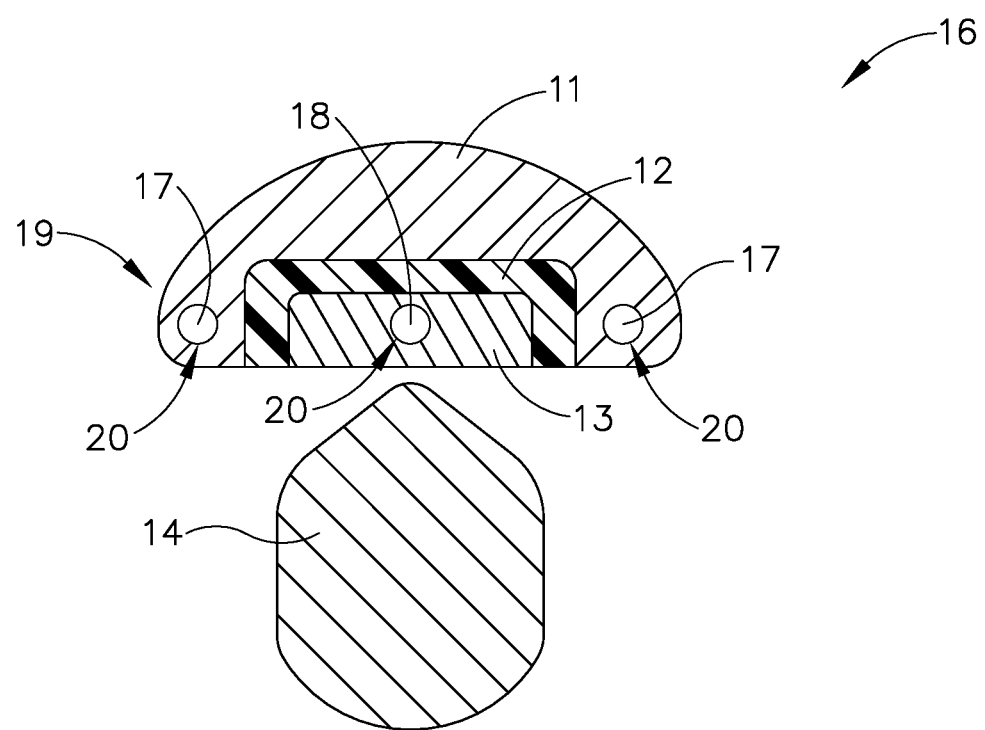
FIG. 26 depicts a cross-section view of another exemplary end effector that may be incorporated into the instrument of FIG. 1, with the end effector in a closed configuration.

FIG. 26 shows another exemplary end effector (16) that may be readily incorporated into instrument (110) in place of end effector (140). End effector (16) is similar to end effector (10) described above. End effector (16) comprises ultrasonic blade (14) and clamp arm assembly (19). With end effector (16), instead of electrically isolating blade (14) by coating blade (14), the electrical energy for clamp arm (11) and clamp pad (13) is provided by running insulated wires (17, 18) through the shaft assembly (130) of instrument (110) in channels (20) positioned within the respective clamp arm (11) and clamp pad (13). Wires (17) are positioned within clamp arm (11) in a manner where wires (17) are located on each side of the clamp arm (11) and spaced away from blade (14) such that there is a portion of clamp arm (11) between wires (17) and blade (14). Similarly, wire (18) is positioned within clamp pad (13) in a manner where wire (18) is spaced away from blade (14) such that there is a portion of clamp pad (13) between wire (18) and blade (14). In this manner, blade (14) is electrically isolated from the RF circuit and the electrosurgical energy is configured to flow through clamped tissue and wires (17, 18). Cutting and sealing operations with end effector (16) occur in the same fashion as explained above with respect to end effector (10).

G. End Effector with Dual Charged Clamp Pads

Figure 27:
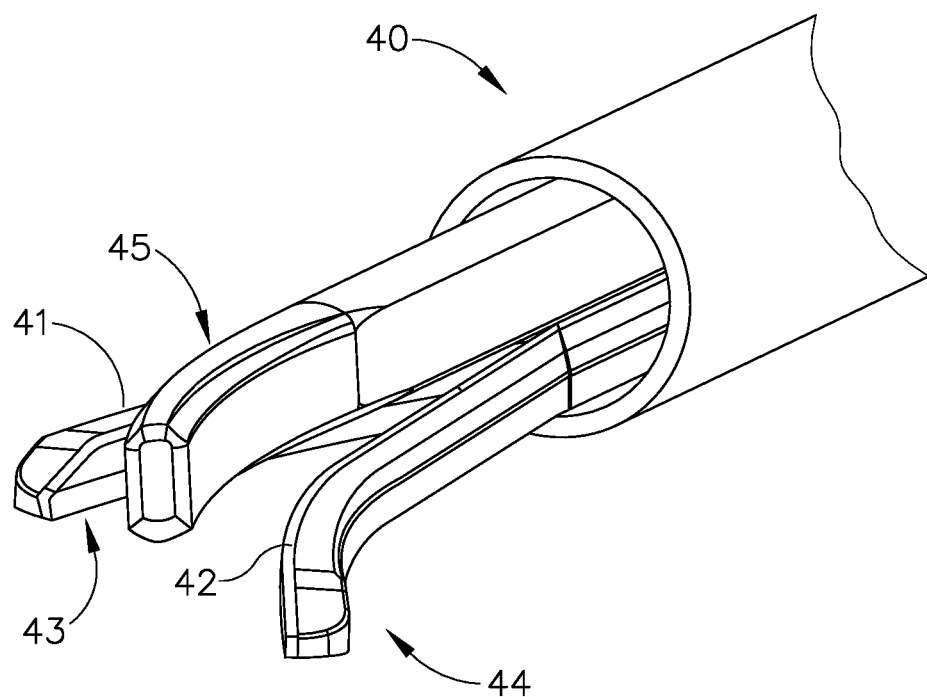
FIG. 27 depicts a perspective view of another exemplary end effector that may be incorporated into the instrument of FIG. 1.
Figure 28:
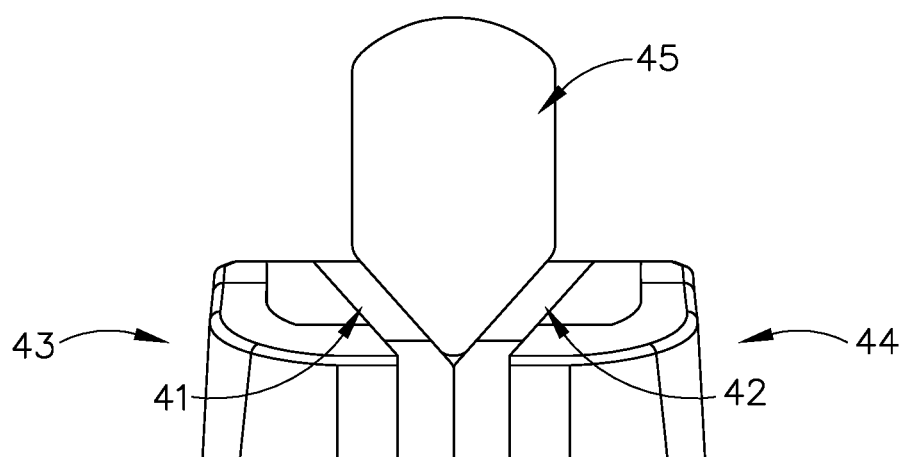
FIG. 28 depicts an end view of a portion of the end effector of FIG. 27.

FIGS. 27 and 28 show another exemplary end effector (40) that may be readily incorporated into instrument (110) in place of end effector (140). End effector (40) comprises a first clamp pad (41), and a second clamp pad (42). Clamp pad (41) is connectable with clamp arm (43), and clamp pad (42) is connectable with clamp arm (44). End effector (40) further comprises blade (45). Each respective clamp arm (43, 44) and attached clamp pad (41, 42) is configured to pivot relative to blade (45) between an open position and a closed position to selectively receive and clamp tissue in end effector (40). In the present example, this pivotal movement occurs in the same or substantially the same manner as the pivoting movement of clamp arm (210) described above. For example, each respective clamp arm (43, 44) is pivotably coupled with an outer tube (202) at one pivot point; and with inner tube (204) at another pivot point. Thus, relative longitudinal movement between tubes (202, 204) provides pivotal movement of clamp arms (43, 44).

In some versions, instrument (110) may be configured with additional tubes or adapters that connect with clamp arms (43, 44) to provide pivotal movement as described herein. Furthermore, clamp arms (43, 44) and their associated clamp pads (41, 42) are configured to move either independently or together. In view of the teachings herein, various ways to configure clamp arms (43, 44) with instrument (110) to provide this pivotal movement will be apparent to those of ordinary skill in the art. By way of example only, clamp arms (43, 44) may be configured and operable to move in accordance with at least some of the teachings of U.S. Pat. No. 9,237,900, entitled "Surgical Instrument with Split Jaw," issued Jan. 19, 2016, the disclosure of which is incorporated by reference herein.

Each clamp pad (41, 42) in the present example is configured with a different polarity so that an RF electrosurgical circuit or pathway is created from clamp pad (41), through captured tissue, to the clamp pad (43), and vice versa. For instance, clamp pad (41) may have a first polarity while clamp pad (42) may have a second polarity. As described above, the conductive nature of clamp pads (41, 42) may be achieved by combining conductive material(s) (46) with the clamp pad material when manufacturing clamp pads (41, 42). The conductive clamp pad (41, 42) are then connectable with an electrical source, such as generator (116), to provide the respective electrical polarity to clamp pads (41, 42). In view of the teachings herein, various ways for connecting conductive clamp pads (41, 42) with generator (116) or another electrical source will be apparent to those of ordinary skill in the art. Also, any of the methods and techniques described above for altering or modifying clamp pad design to shape the electrosurgical circuit or pathway may be used with clamp pads (41, 42) of end effector (40). In view of the teachings herein, such alterations or modification of clamp pads (41, 42) to shape the electrosurgical circuit and resultant sealing will be apparent to those of ordinary skill in the art. Furthermore, each clamp arm (43, 44) is electrically isolated from its respective clamp pad (41, 42) through various insulating materials as will be understood by those of ordinary skill in the art in view of the teachings herein.

In the example where clamp arms (43, 44) move independently relative to blade (45), either or both clamp arms (43, 44) can be moved to the closed position to compress tissue between the respective clamp pad (41, 42) and blade (45). Blade (45) can be activated to oscillate such that compressed tissue will be ultrasonically severed along the regions where tissue is compressed between clamp pads (41, 42) and blade (45). Because each clamp pad (41, 42) in the present example has a different polarity, to achieve RF electrosurgical sealing, both clamp pads (41, 42) are moved so that they contact the captured tissue. This is accomplished by moving each clamp arm (43, 44), containing clamp pads (41, 42) respectively, to the closed position. With both clamp arms (43, 44) closed, RF electrosurgical sealing can be provided via clamp pads (41, 42) either before, during, or after the ultrasonic cutting process.

H. End Effector with Outriggers with Selective Insulation

Figure 29:
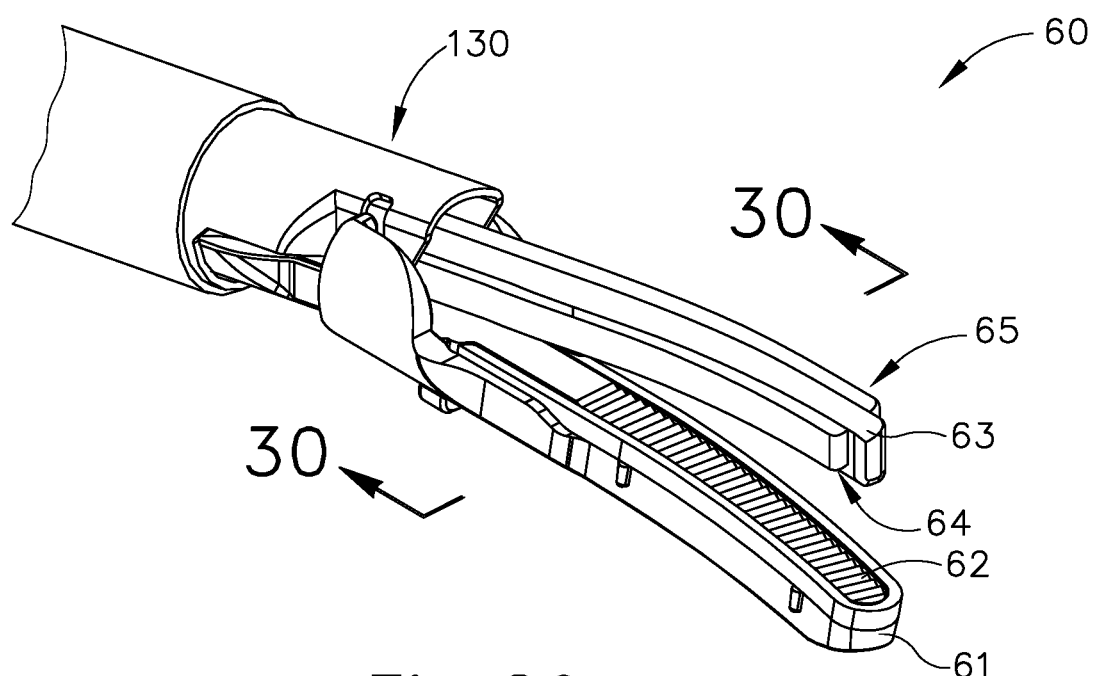
FIG. 29 depicts a perspective view of another exemplary end effector that may be incorporated into the instrument of FIG. 1.
Figure 30:
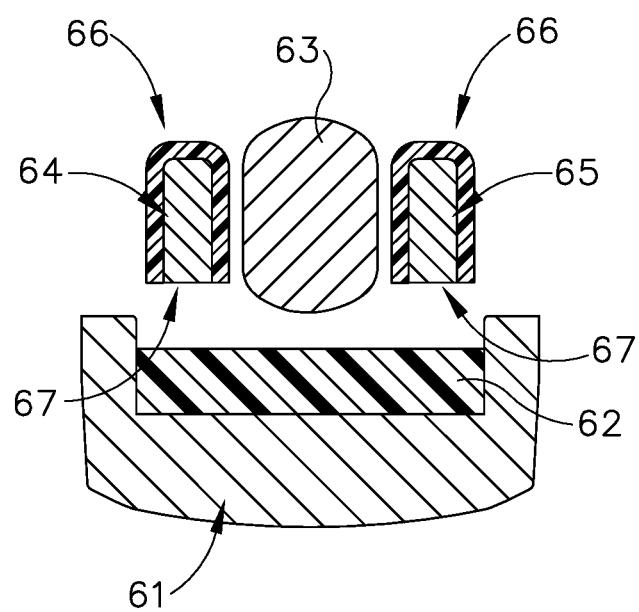
FIG. 30 depicts a cross-section view of the effector of FIG. 29, taken along line 30-30 of FIG. 29.

FIGS. 29 and 30 show another exemplary end effector (60) that may be readily incorporated into instrument (110) in place of end effector (140). End effector (60) comprises clamp arm (61), clamp pad (62), and blade (63), which are all nonconductive in the present example, Ultrasonic cutting with end effector (60) occurs in the manner described above, where tissue is compressed between blade (63) and clamp pad (62) with blade (63) being activated to oscillate ultrasonically to thereby sever clamped and compressed tissue.

To provide RF electrosurgical sealing in a way where blade (63) remains neutral or nonconductive, and may be coated with xylan or another suitable coating, end effector (60) further comprises a first and second outrigger (64, 65) that each extend from shaft assembly (130). In some other versions, first and second outriggers (64, 65) may extend from blade (63). In the present example, outriggers (64, 65) include a coating (66). Coating (66) is applied selectively to outriggers (64, 65). As shown in the illustrated version of FIG. 30, the selective coating (66) is applied around all sides of outriggers (64, 65) except for an exposed surface (67) of each outrigger (64, 65), which faces or is adjacent to clamp pad (62).

Coating (66) is configured such that coating (66) prevents blade (63) from contacting outriggers (64, 65) directly. Coating (66) also provides insulating properties so as to inhibit the transfer of electrical energy from outriggers (64, 65) to blade (63) or clamp arm (61) thereby causing a short circuit to the RF electrosurgical path as discussed below. In some versions coating (66) may comprise polytetrafluoroethylene, but other coating materials may be used as will be apparent to those of ordinary skill in the art in view of the teachings herein.

In the present example, each of outriggers (64, 65) are conductive. Furthermore, outriggers (64, 65) have opposite polarities. With this configuration, when tissue is clamped between clamp arm (61) and blade (63), a RF electrosurgical circuit or path is defined that extends from one of outriggers (64, 65) through the clamped tissue, to the other of outriggers (64, 65). As shown in the illustrated version, exposed surfaces (67) of outriggers (64, 65), which are closest to or facing clamp pad (62), are uncoated thereby allowing electrosurgical energy to flow through the tissue contacting outriggers (64, 65).

In some versions, selective coating (66) is applied such that the exposed surfaces (67) of outriggers (64, 65) are uncoated and thus exposed to clamp pad (62) and clamped tissue along the length of clamp pad (62). In some other versions, selective coating (66) may be applied to outriggers (64, 65) in a pattern so as to alter the pathway of the RF electrosurgical energy flow and thus the electrical field and the resultant sealing shape or pattern. By way of example only, and not limitation, several such features and techniques for altering or manipulating the pathway of the RF electrosurgical energy are described herein with respect to other end effector versions. In view of these teachings, such modifications to the pattern of selective coating (66) on outriggers (64, 65) to alter the RF electrosurgical pathways and the resulting sealing patterns will be apparent to those of ordinary skill in the art. For example, in some versions, instead of exposed surfaces (67) being uncoated along the length of clamp pad (62), selective coating (66) may be applied such that exposed surfaces (67) comprise alternating regions of coating and uncoated areas.

I. End Effector with Clamp Arm with Overmolded Electrodes

Figure 31:
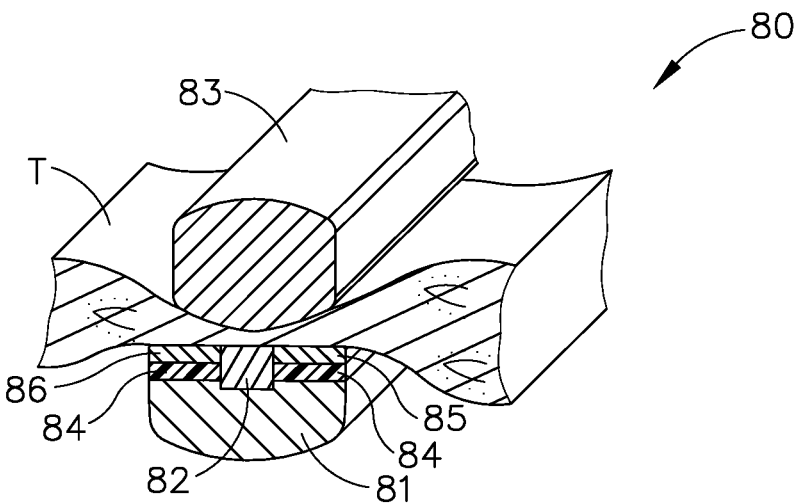
FIG. 31 depicts a cross-section view of another exemplary end effector that may be incorporated into the instrument of FIG. 1.

FIG. 31 shows another exemplary end effector (80) that may be readily incorporated into instrument (110) in place of end effector (140). End effector (80) comprises clamp arm (81), clamp pad (82), and blade (83). In the present example, blade (83) is nonconductive and may be coated with an insulating and/or nonstick material or coating. Clamp pad (82) is also nonconductive in the present example. With tissue (T) compressed between clamp pad (82) and blade (83) when end effector (80) is in a closed position, blade (83) may be activated and tissue (T) ultrasonically cut or severed.

In the present example, RF electrosurgical sealing features are incorporated into clamp arm (81). For instance, clamp arm (81) comprises an insulator (84) that extends along clamp arm (81) along each side of clamp pad (82). Insulator (84) is overmolded onto clamp arm (81), but may be connected with clamp arm (81) other ways that will be apparent to those of ordinary skill in the art in view of the teachings herein. First and second electrodes (85, 86) are each located on and along insulator (84) along each side of clamp pad (82). In this configuration, clamp arm (81) is electrically isolated from first and second electrodes (85, 86) by insulator (84). As will be discussed in greater detail below, each of first and second electrodes (85, 86) are conductive and first electrode (85) has an oppositely polarity from second electrode (86). With this configuration, an RF electrosurgical path is defined extending through tissue (T) between electrodes (85, 86).

Figure 32:
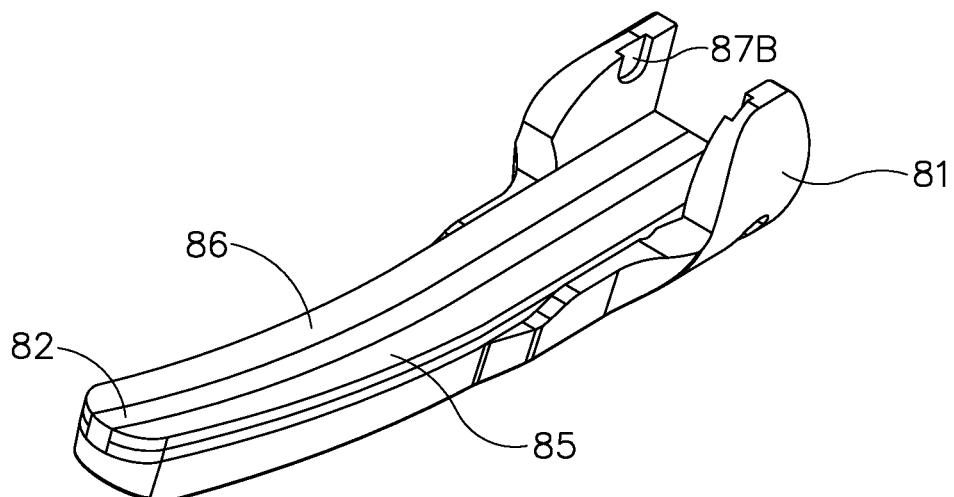
FIG. 32 depicts a perspective view of the clamp arm of the end effector of FIG. 31.
Figure 33:
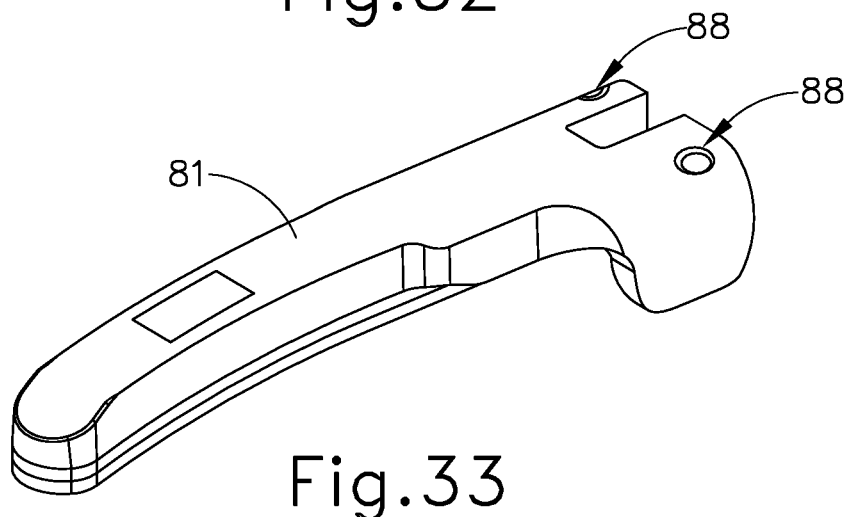
FIG. 33 depicts another perspective view of the clamp arm of the end effector of FIG. 31.
Figure 34:
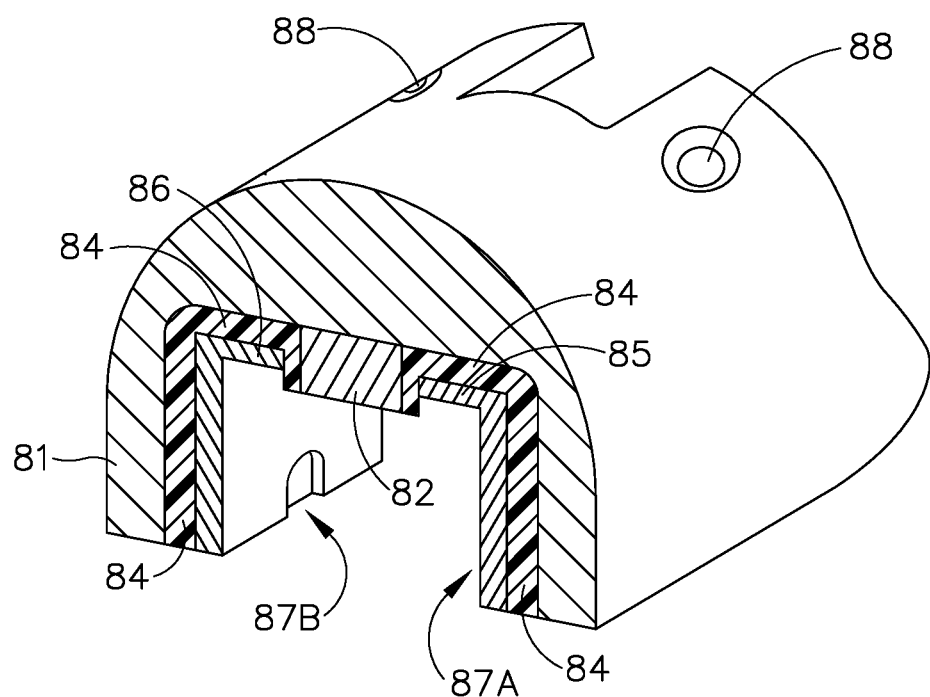
FIG. 34 depicts another cross-section view of the clamp arm of the end effector of FIG. 31.

FIGS. 32-34 show other views of clamp arm (81) and the RF electrosurgical sealing features incorporated therein. As seen in the illustrated version of FIGS. 92 and 94, in addition to clamp pad (82) and first and second electrodes (85, 86), clamp arm (81) includes pull slots (87A, 87B) on each side of clamp arm (81). Pull slots (87A, 87B) are configured to connect with a tube of shaft assembly (130) to provide pivoting movement of clamp arm (81) for opening and closing end effector (80) as described above. In the present example, pull slot (87A) is formed with and/or connects with first electrode (85). Similarly, pull slot (87B) is formed with and/or connects with second electrode (86). In exemplary versions where pull slots (87A, 87B) are formed with respective first and second electrodes (85, 86), each of first and second electrodes (85, 86) comprise a respective longitudinally extending portion and a respective transversely extending portion. In particular, the transversely extending portion comprises the pull slot (87A, 87B) and the longitudinally extending portion extends along the length of clamp arm (81) on top of insulator (84). It should further be understood, as shown in FIG. 34, that insulator (84) also extends transversely, in addition to extending longitudinally, such that clamp arm (81) is fully isolated from first and second electrodes (85, 86). With pull slots (87A, 87B) connecting with first and second electrodes (85, 86) respectively, and with pull slots (87A, 87B) connectable with a tube of shaft assembly (130), as will be described further below, one or more tubes of shaft assembly (130) can be configured to deliver the electrical energy to first and second electrodes (85, 86).

FIG. 33 shows another view of clamp arm (81), with clamp arm (81) comprising openings (88) at each side of a top side of clamp arm (81). Openings (88) are also visible in FIG. 34. Openings (88) are configured to connect with one or more tubes of shaft assembly (130). In the present example, openings (88) connect with corresponding pins or posts located on outer tube of shaft assembly (130). Pull slots (87A, 87B) connect with corresponding pins or posts located on inner tube of shaft assembly (130). In this manner, as described above, clamp arm (81) is pivotable to open and close by translating inner and outer tubes relative to one another. In the present example, openings (88) are isolated from first and second electrodes (85, 86). For example, openings (88) comprise an overmolded plastic insulating material in the present example. With this insulating material, outer tube connecting with openings (88) is also isolated from first and second electrodes (85, 86).

Figure 35:
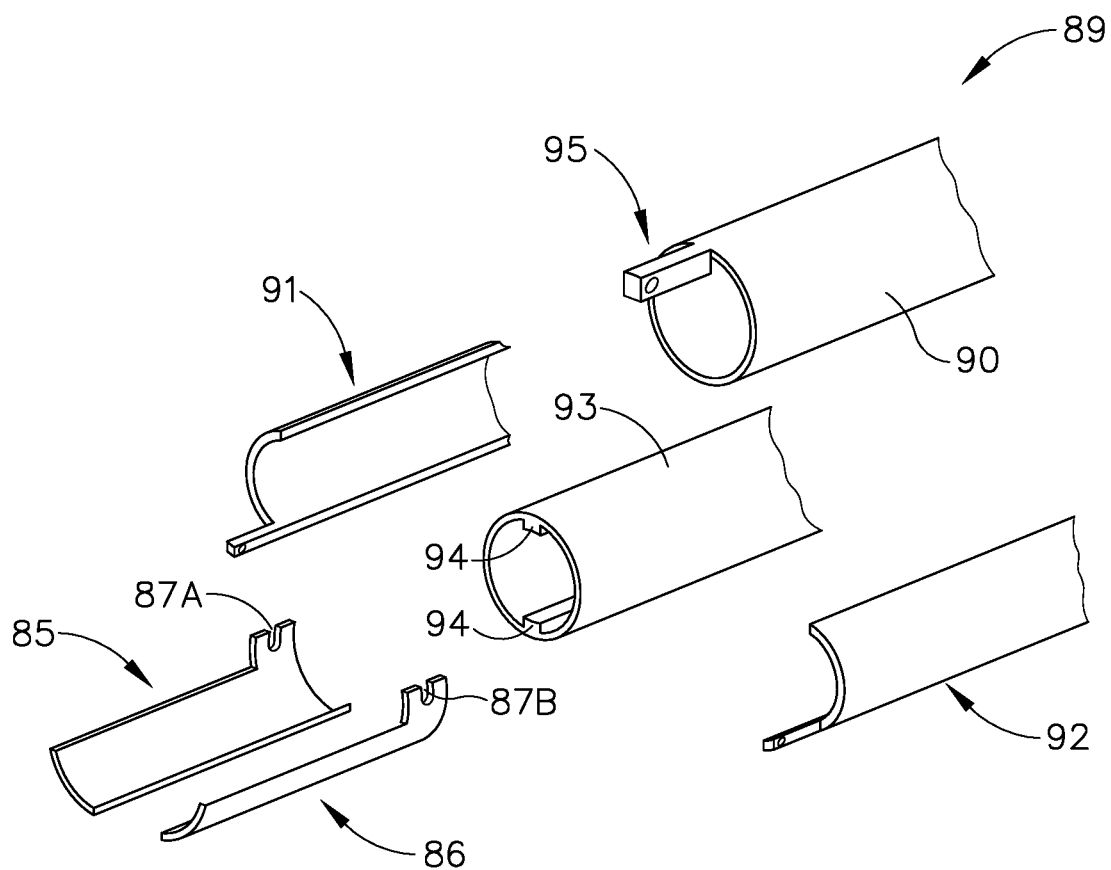
FIG. 35 depicts a partial exploded view of the end effector of FIG. 31, with a tube assembly that may be incorporated into the shaft assembly of FIG. 1 and used with the end effector of FIG. 31.
Figure 36:
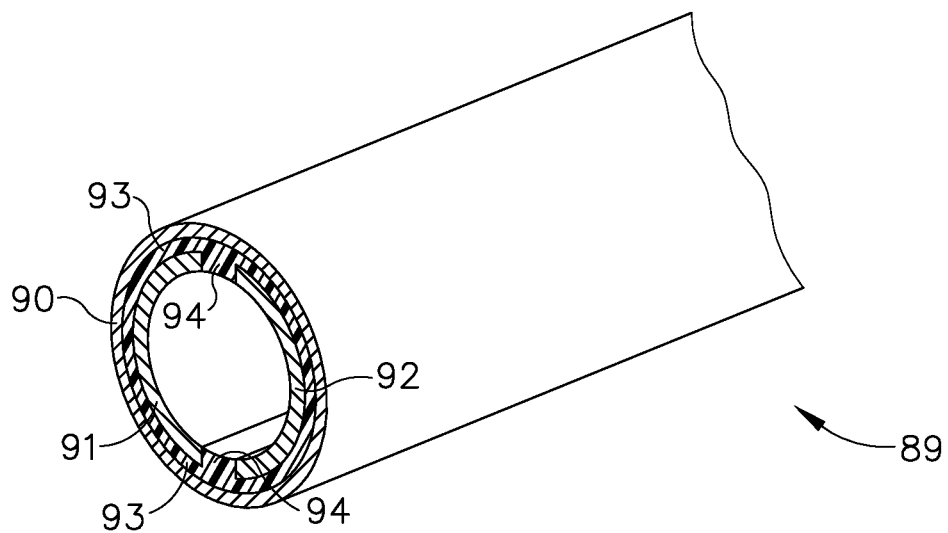
FIG. 36 depicts a cross-section view of the tube assembly of FIG. 35.

FIGS. 35-36 show a tube assembly (89) with first and second electrodes (85, 86), Tube assembly (89) comprises outer tube (90), first half inner tube (91), second half inner tube (92), and insulator tube (93). Tube assembly (89) may replace outer tube (202) and inner tube (204) described above, such that shaft assembly (130) is usable with end effector (80) as further described herein. In the assembled state for tube assembly (89), insulator tube (93) sits within outer tube (90). First half inner tube (91) and second half inner tube (92) each sit within insulator tube (93). Insulator tube (93) comprises dividers (94) that separate first and second half inner tubes (91, 92) such that first and second half inner tubes (91, 92) do not directly contact one another. Insulator tube (93) further separates outer tube (90) from first and second half inner tubes (91, 92) such that outer tube (90) does not directly contact first and/or second half inner tubes (91, 92).

In the present example, outer tube (90) is nonconductive while first and second half inner tubes (91, 92) are conductive. First and second half inner tubes (91, 92) respectively connect with pull slots (87A, 87B) of first and second electrodes (85, 86) as described above. First half inner tube (91) is configured to provide a first electrical polarity to first electrode (85) through its connection with pull slot (87A). Second half inner tube (92) is configured to provide a second electrical polarity to second electrode (86) through its connection with pull slot (87B).

As described above, insulator (84) electrically isolates clamp arm (81) from first and second electrodes (85, 86), Additionally, openings (88) are insulated as mentioned. Outer tube (90) includes elongated member (95) having pins or posts that connect with openings (88) in clamp arm (81). With this configuration, clamp arm (81) of end effector (80) connects with both outer tube (90) and with first and second half inner tubes (91, 92). First and second half inner tubes (91, 92) are configured to translate in unison. As described above, with translational movement of first and second half inner tubes (91, 92) relative to outer tube (90), clamp arm (81) opens and closes with a pivoting action. In other versions outer tube may translate relative to first and second half inner tubes (91, 92) to pivot clamp arm (81).

In the configuration described above, an RF electrosurgical path is defined as extending through tissue (T) between electrodes (85, 86). When tissue (T) is clamped between clamp arm (81) and blade (83), tissue (T) can be ultrasonically cut along the region between clamp pad (82) and blade (83). Furthermore, tissue (T) can be sealed along each side of the cut line where tissue (T) contacts first and second electrodes (85, 86).

Figure 37:
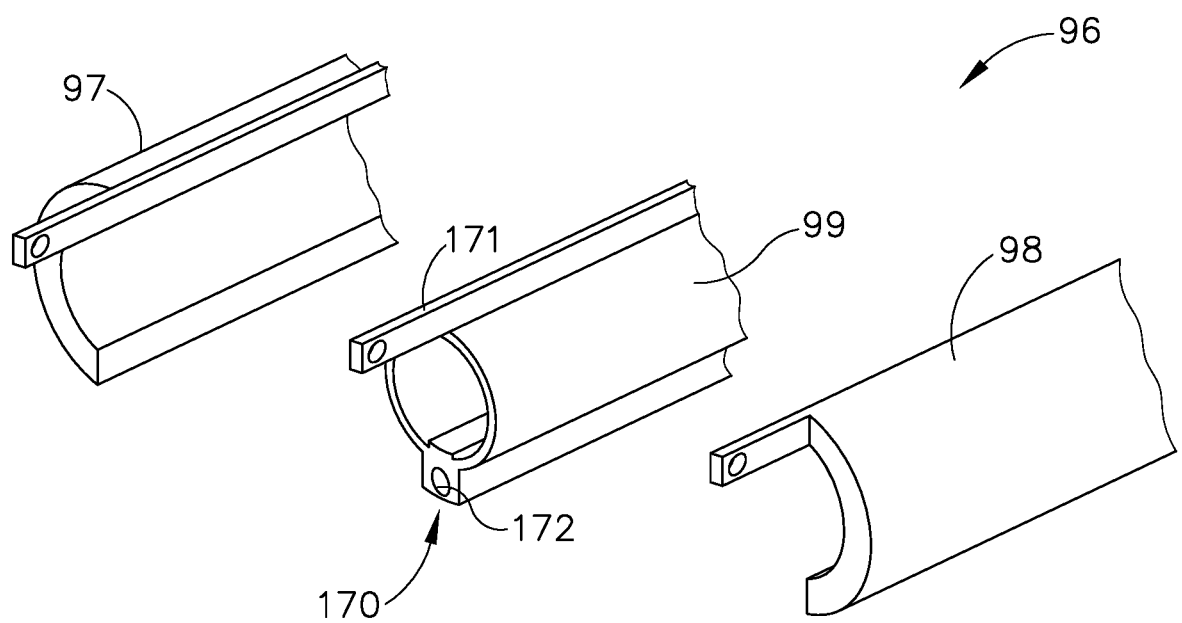
FIG. 37 depicts an exploded view of another exemplary tube assembly that may be incorporated into the shaft assembly of FIG. 1 and used with the end effector of FIG. 31.
Figure 38:
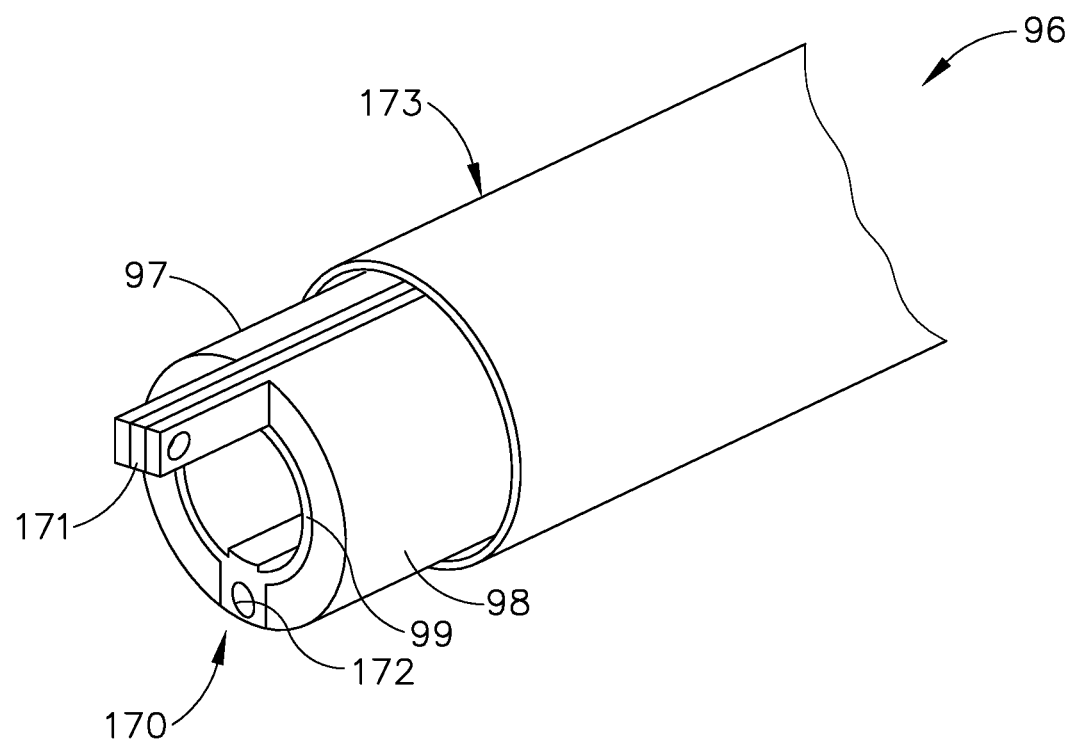
FIG. 38 depicts a perspective view of the tube assembly of FIG. 37.

FIGS. 37 and 38 show another tube assembly (96) that may be used with end effector (80) instead of tube assembly (89). Tube assembly (96) is similar to tube assembly (89). However, tube assembly (96) of this example is configured such that the outer tube provides the electrical energy to first and second electrodes (85, 86) instead of the inner tube as in tube assembly (89).

Tube assembly (96) comprises first half outer tube (97), second half outer tube (98), insulator tube (99), and inner tube (not shown). Tube assembly (96) may replace outer tube (202) and inner tube (204) described above, such that shaft assembly (130) is usable with end effector (80) as further described herein. In the assembled state for tube assembly (96), insulator tube (99) sits within first and second half outer tubes (97, 98). Inner tube (not shown) sits within insulator tube (99). Insulator tube (99) comprises dividers (170, 171) that separate first and second half outer tubes (97, 98) such that first and second half outer tubes (97, 98) do not directly contact one another. Insulator tube (99) further separates inner tube from first and second half outer tubes (97, 98) such that inner tube does not directly contact first and/or second half outer tubes (97, 98). Divider (170) of insulator tube (99) defines a bore (172) that is configured such that wires or cables can pass through bore (172) to extend through instrument (110). Such wires and/or cables can be used to provide electrical energy to first and second electrodes (85, 86) in some versions instead of providing electrical energy through inner or outer tube structures. It should also be understood that wires and/or cables can be used for electrical grounding.

In the present example, inner tube is nonconductive while first and second half outer tubes (97, 98) are conductive. First and second half outer tubes (97, 98) respectively connect with openings (88). In the present example using tube assembly (96), clamp arm (81) and first and second electrodes (85, 86) are modified such that electrical energy may be communicated through openings (88) to first and second electrodes (85, 86) instead of through pull slots (87A, 87B) as described above. In view of the teachings herein, such modifications to clamp arm (81) to transfer electrical energy to first and second electrodes (85, 86) by way of openings (88) instead of pull slots (87A, 87B) will be apparent to those of ordinary skill in the art. In this manner, first half outer tube (97) is configured to provide a first electrical polarity to first electrode (85) through its connection, and second half outer tube (98) is configured to provide a second electrical polarity to second electrode (86). As shown in FIG. 38, a heat shrink tube (173) can surround first and second half outer tubes (97, 98) to isolate other components of shaft assembly (130) and instrument (110) from conductive first and second outer tube halves (97, 98).

As described above, insulator (84) electrically isolates clamp arm (81) from first and second electrodes (85, 86), In the present example using tube assembly (96), insulator (84) and clamp arm (81) are also modified such that clamp arm (81) remains electrically isolated from first and second half outer tubes (97, 98). In view of the teachings herein, such modifications to insulator (84) and clamp arm (81) to maintain electrical isolation of clamp arm (81) will be apparent to those of ordinary skill in the art. Additionally, with tube assembly (96) pull slots (87A, 87B) are insulated such that inner tube remains electrically isolated from first and second electrodes (85, 86). With this configuration, clamp arm (81) of end effector (80) connects with both inner tube and with first and second half outer tubes (97, 98). First and second half outer tubes (97, 98) are configured to translate in unison. As described above, with translational movement of first and second half outer tubes (97, 98) relative to inner tube, clamp arm (81) opens and closes with a pivoting action. In some other versions, inner tube may translate relative to first and second half outer tubes (97, 98) to pivot clamp arm (81).

In the configuration described above with tube assembly (96), an RF electrosurgical path is defined as extending through tissue (T) between electrodes (85, 86). When tissue (T) is clamped between clamp arm (81) and blade (83), tissue (T) can be ultrasonically cut along the region between clamp pad (82) and blade (83). Furthermore, tissue (T) can be sealed along each side of the cut line where tissue (T) contacts first and second electrodes (85, 86).

Figure 39:
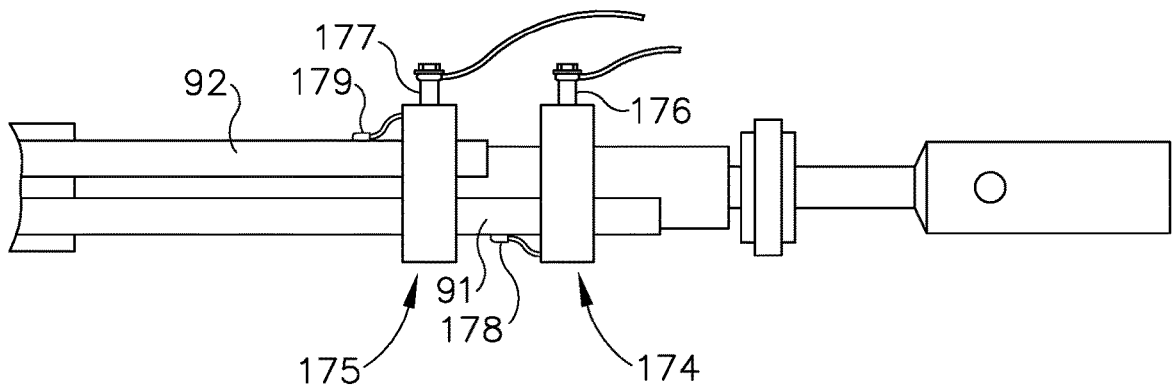
FIG. 39 depicts a side view of a proximal portion of the tube assembly of FIG. 35, showing electrical connections of the tube assembly with electrical components.
Figure 40:
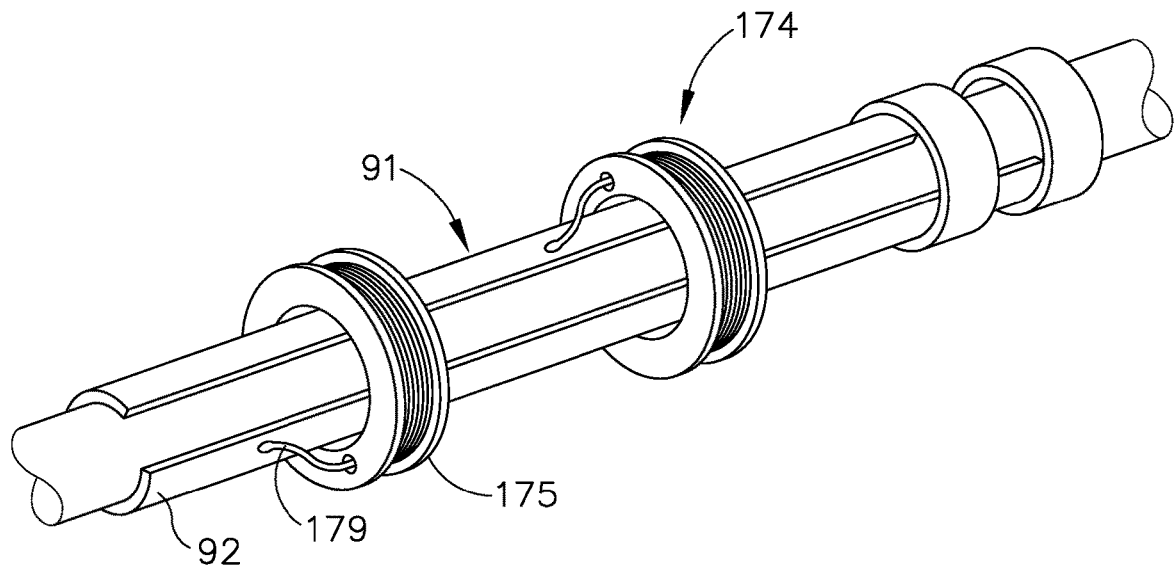
FIG. 40 depicts a perspective view of the proximal portion of the tube assembly of FIG. 39.

FIGS. 39 and 40 show further proximal portions of tube assembly (89), and in particular connections of first and second half inner tubes (91, 92) with first and second rings (174, 175) to provide RF electrical energy to first and second half inner tubes (91, 92), and ultimately to first and second electrodes (85, 86). In the present example, first half inner tube (91) connects with first ring (174), and second half inner tube (92) connects with second ring (175). Ring (174) further connects with ring contact (176), which connects with one of the cables that connects with generator (116) to provide the electrical energy. Ring (175) further connects with ring contact (177), which connects with the other of the cables that connects with generator (116) to provide the electrical energy. In one version, ring contacts (176, 177) comprise contact springs.

First ring (174) and second ring (175) comprise respective connection members (178, 179). Connection member (178) contacts first half inner tube (91) to provide electrical continuity with first half inner tube (91). Connection member (179) contact second half inner tube (92) to provide electrical continuity with second half inner tube (92). In the present example, first ring (174) and second ring (175) are welded or otherwise fixedly attached to respective first and second half inner tubes (91, 92). In this manner, shaft assembly (130) is rotatable 360 degrees and electrical contact is maintained between first and second rings (174, 175) and respective first and second half inner tubes (91, 92). In some versions, rings (174, 175) are rotatable relative to respective first and second ring contacts (176, 177), such that when shaft assembly rotates, rings (174, 175) rotate also based on their fixed connection with respective first and second half inner tubes (91, 92), This rotation of rings (174, 175) is relative to ring contacts (176, 177). However, ring contacts (176, 177) remain in electrical contact with respective rings (174, 175), thereby providing electrical continuity from respective cables to respective first and second half inner tubes (91, 92), and ultimately to respective first and second electrodes (85, 86). With rings (174, 175) rotatable relative to ring contacts (176, 177), cables within instrument (110) that connect with ring contacts (176, 177) can remain generally stationary when the shaft assembly is rotated.

Figure 41:
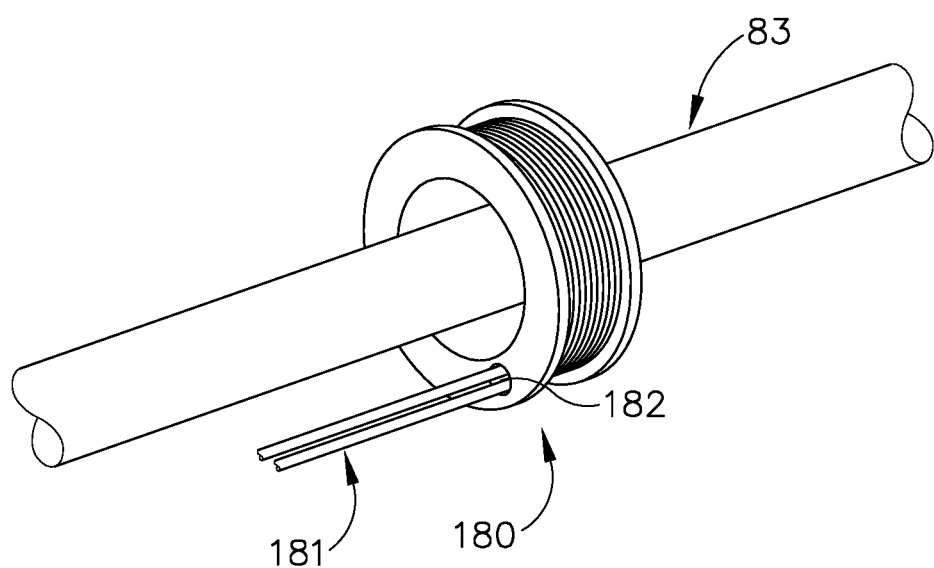
FIG. 41 depicts a perspective view of an exemplary actuation ring usable with the end effector of FIG. 31 to open and close the end effector.

FIG. 41 shows actuation ring (180) with blade (83) passing through actuation ring (180). In the present example, actuation ring (180) is configured to connect with first inner half tube (91) and second inner half tube (92) to translate inner half tubes (91, 92) relative to outer tube (90) so as to pivot clamp arm (81) to open and close clamp arm (81). Actuation ring (180) is connectable with trigger (128) such that clamp arm (81) is pivotable toward ultrasonic blade (83) in response to pivoting of trigger (128) toward pistol grip (124); and such that clamp arm (81) is pivotable away from ultrasonic blade (83) in response to pivoting of trigger (128) away from pistol grip (124). Various suitable ways in which actuation ring (180) may be coupled with inner half tubes (91, 92) and trigger (128) will be apparent to those of ordinary skill in the art in view of the teachings herein. In some versions, actuation ring (180) may be connectable with outer tube (90) instead of with inner half tubes (91, 92) to provide the translation necessary to pivot clamp arm (81) between open and closed positions. As shown in FIG. 41, actuation ring (180) may be configured with a bore (182) that allows wires (181) to pass through actuation ring (180) in some versions.

J. End Effector with Conductive Pad with Two Poles

FIG. 42 shows another exemplary end effector (150) that may be readily incorporated into instrument (110) in place of end effector (140). End effector (150) comprises clamp arm (151), clamp pad (152), and blade (153). Clamp pad (152) comprises first portion (154) and second portion (155). An insulator (156) separates first and second portions (154, 155). Insulator (156) also separates respective first and second portions (154, 155) of clamp (152) from clamp arm (151).

Clamp pad (152) is constructed from conductive material (157) such that first and second portion (154, 155) are each electrically conductive. Furthermore, each conductive first and second portions (154, 155) of clamp pad (152) connect either directly or indirectly with respective cables that lead to generator (116) or another source of RF electrosurgical power. First and second portions (154, 155) of clamp pad (152) are oppositely polarized. In some versions, conductive material (157) within clamp pad (152) comprises conductive fibers that are formed in clamp pad (152). These fibers may be oriented longitudinally along clamp pad (152) as shown in FIG. 43. Alternatively, these fibers may be oriented transversely along clamp pad (152) as shown in FIG. 44. Any other suitable fiber orientation may be used.

As yet another merely illustrative variation, conductive material (157) comprises metal that is impregnated within rubber during clamp pad (152) construction. This metal may also be oriented longitudinally, transversely, or otherwise along clamp pad (152), or in any other suitable pattern including a random orientation. Some exemplary metals that may be used with clamp pad (152) to impart conductivity to clamp pad (152) include, but are not limited to, silver, silver-plated aluminum, silver-plated copper, silver-plated glass, nickel-plated graphite, among others. Another exemplary conductive material (157) usable with clamp pad (152) includes black carbon. In view of the teachings herein, other materials that may be used with clamp pad (152) to make clamp pad (152) conductive, as well as techniques for incorporating such materials with clamp pad (152), will be apparent to those of ordinary skill in the art.

With the orientation of insulator (156) as described above, end effector (150) first and second portions (154, 155) of conductive pad (152) provide oppositely polarized electrodes of an RF electrosurgical pathway or circuit. Furthermore, the electrically conductive portions of clamp pad (152) are isolated from one another and from clamp arm (151). With this configuration, a single treatment region is defined between clamp pad (152) and blade (153), and both ultrasonic cutting and RF electrosurgical sealing of tissue sealing can be provided within the single treatment region.

In some versions, clamp pad (152) is configured as a disposable clamp pad (152) that wears away gradually as heat is generated by blade (153). With this configuration, conductive material (157) within clamp pad (152) may be configured to wear away such that RF electrosurgical sealing becomes less effective and thereby serves to indicate the time is right to replace clamp pad (152).

When end effector (150) is used with instrument (110) to cut and seal tissue (T), as mentioned above a single treatment region is defined by tissue (T) compressed between blade (153) and clamp pad (152). With tissue (T) compressed and blade (153) activated, ultrasonic cutting of tissue (T) occurs along this compressed region of tissue (T). Additionally, or separately, RF electrosurgical sealing occurs in this single treatment region. More specifically, with tissue (T) clamped between blade (153) and pad (152), an RF electrosurgical pathway or circuit is defined as extending through tissue between first portion (154) of clamp pad (152) and second portion (155) of clamp pad (152), In this exemplary RF electrosurgical circuit, first portion (154) is provided at a first electrical polarity while second portion (155) is provided at a second electrical polarity. When using end effector (150) for ultrasonic cutting and RF electrosurgical sealing, these modalities may be used in any order, or at the same time. Furthermore, just one of these modalities may be used in some applications, such that it is not necessary in all circumstances to use both modalities with end effector (150).

K. End Effector with Dual Lengthwise Sections

Figure 45:
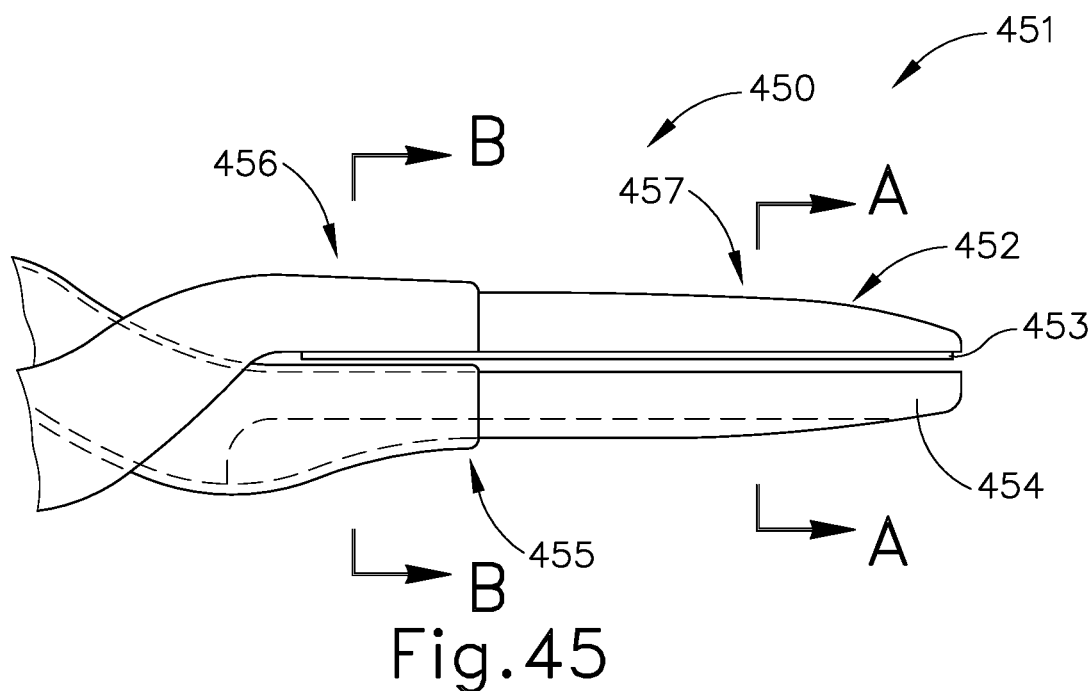
FIG. 45 depicts a side view of another exemplary end effector, shown in a shear device.

FIG. 45 shows another exemplary end effector (450) configured for use with a shears device (451). While the present example illustrates shears device (451), in view of the teachings herein, the features and techniques pertaining to the ultrasonic cutting and RF electrosurgical sealing are also applicable to instrument (110) and one or more of the end effectors described herein that are readily usable with instrument (110).

In certain procedure, e.g. solid organ procedures, it may be desirable to crush tissues to divide the parenchymous tissues without disturbing the vessels and ducts lying within. By way of example only, this may occur in procedures where a portion of a patient's liver is removed. After crushing the parenchyma, the exposed vessels and ducts can then be sealed and cut. In some instances, larger jaw or clamp arm devices are used with such procedures. Some such larger jaw or clamp arm devices may include shears like shears (451) shown in FIG. 45. It should therefore be understood that the same shears (451) may be used to crush the parenchyma, sever the exposed vessels and ducts, and seal the severed vessels and ducts. In view of the teachings herein, other devices usable in such procedures as described here will be apparent to those of ordinary skill in the art. Such other devices include, but are not limited to, instrument (110) and end effectors readily usable with instrument (110), including end effectors incorporating modifications based on the teachings described and shown here with respect to end effector (450).

Referring to FIGS. 45-49, end effector (450) comprises clamp arm (452), clamp pad (453), blade (454), and blade cover (455). End effector (450) further comprises two sections that extend lengthwise along clamp arm (452). The two lengthwise sections comprise a proximal section (456) and a distal section (457). In the present example, proximal section (456) is configured for clamping tissue without or with minimal energy-based cutting. Instead of being configured for energy-based cutting, proximal section (456) is configured to provide mechanical crushing of tissue as described above; and/or to deliver bipolar electrosurgical energy to seal tissue. Distal section (457) is configured for cutting tissue by delivering ultrasonic and/or bipolar electrosurgical energy, where the tissue is cut by way of ultrasonic energy. While the energy-based cutting section is distal section (457) in the present example, in some other versions, the functions of the proximal and distal sections (456, 457) may be reversed such that the energy-based cutting occurs at proximal section (456), while the bipolar coagulation and sealing occurs at the distal section (457).

In the present example, proximal section (456) for sealing and coagulation includes opposing clamping electrode surfaces that deliver bipolar electrosurgical energy to clamped tissue. For instance, the clamp arm side comprises a first electrode (458) and blade side comprises a second electrode (459). In some versions, first electrode (458) is configured with clamp arm (452) such that clamp arm (452) provides a first polarity in the bipolar RF electrosurgical circuit. In some other versions, first electrode (458) is configured with clamp pad (453) such that clamp pad (453) provides a first polarity in the bipolar RF electrosurgical circuit. In still other versions, first electrode (458) comprises a conductive plate connectable with clamp arm (452) and/or clamp pad (453), where the conductive plate is configured to provide a first polarity in the bipolar RF electrosurgical circuit. In view of the teachings herein, other various ways to provide first electrode (458) on clamp arm side of end effector (450) will be apparent to those of ordinary skill in the art.

In some versions, second electrode (459) is configured with blade (454) such that blade (454) provides a second polarity of the bipolar RF electrosurgical circuit. In some other versions, second electrode (459) is configured with blade cover (455) such that blade cover (455) provides the second polarity of the bipolar RF electrosurgical circuit. In still other versions, second electrode (459) comprises a conductive plate connectable with blade (454) or blade cover (455), where the conductive plate provides the second polarity of the bipolar RF electrosurgical circuit. In examples where second electrode (459) is formed by blade (454), second electrode (459) can be ultrasonically active even though present in proximal section (456). In examples where second electrode (459) is formed by separate components not part of blade (454), second electrode (459) is not ultrasonically active. Furthermore, even where second electrode (459) is formed as part of blade (454) and thus is ultrasonically active, the displacement of blade (454) in proximal section (456) is about 70% less than the displacement that occurs at the distal tip of blade (454). In view of the teachings herein, other various ways to provide second electrode (459) on blade side of end effector (450) will be apparent to those of ordinary skill in the art.

In the present example, distal section (457) for ultrasonic cutting includes clamp pad (453) and blade (454) such that tissue can be clamped between and severed by ultrasonic cutting when blade (454) is activated to oscillate ultrasonically. Distal section (457) can optionally include opposing clamping electrode surfaces that deliver bipolar energy to clamped tissue so that sealing and coagulation can be provided in distal section (457) also. For instance, in an example that includes RF electrosurgical sealing in distal section (457), the clamp arm side comprises a third electrode (460) and blade side comprises a fourth electrode (461). In some versions, third electrode (460) is configured with clamp arm (452) such that clamp arm (452) provides a first polarity of the bipolar RF electrosurgical circuit. In some other versions, third electrode (460) is configured with clamp pad (453) such that clamp pad (453) provides the first polarity of the bipolar RF electrosurgical circuit. In still other versions, third electrode (460) comprises a conductive plate connectable with clamp arm (452) and/or clamp pad (453), where the conductive plate provides the first polarity of the bipolar RF electrosurgical circuit. In some versions, first electrode (458) and third electrode (460) may be the same structure that spans both proximal and distal sections (456, 457) of end effector (450). In view of the teachings herein, other various ways to provide third electrode (460) on clamp arm side of end effector (450) will be apparent to those of ordinary skill in the art.

In some versions, fourth electrode (461) is configured with blade (454) such that blade (454) provides the second polarity of the bipolar RF electrosurgical circuit. In some other versions, fourth electrode (461) is configured with blade cover (455) such that blade cover (455) provides the second polarity of the bipolar RF electrosurgical circuit. In still other versions, fourth electrode (461) comprises a conductive plate connectable with blade (454) or blade cover (455), where the conductive plate provides the second polarity of the bipolar RF electrosurgical circuit. In some versions, second electrode (459) and fourth electrode (461) may be the same structure that spans both proximal and distal sections (456, 457) of end effector (450). In view of the teachings herein, other various ways to provide fourth electrode (461) on blade side of end effector (450) will be apparent to those of ordinary skill in the art.

Figure 46:
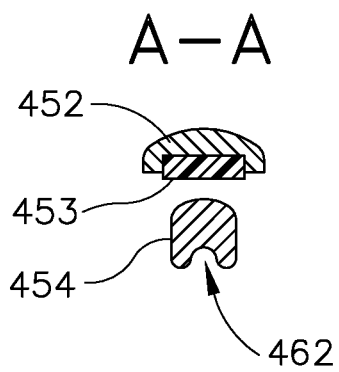
FIG. 46 depicts a cross-section view of the end effector of FIG. 45 taken along the distal section at line A-A of FIG. 45.
Figure 47:
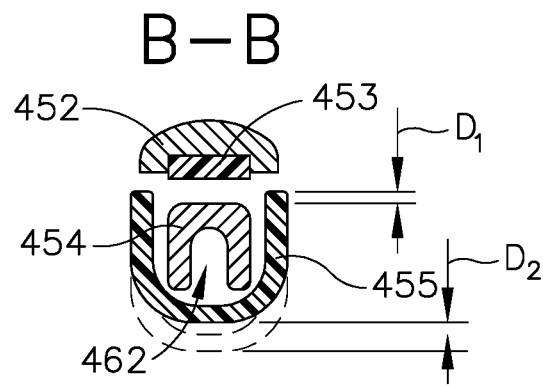
FIG. 47 depicts a cross-section view of the end effector of FIG. 45 taken along the proximal section at line B-B of FIG. 45.

FIGS. 46 and 47 show exemplary cross-sections of a version of end effector (450) where clamp arm (452) provides the first polarity of the bipolar RF electrosurgical circuit. In distal section (457) shown in FIG. 46, tissue can be clamped between clamp pad (453) and blade (454). Blade (454) oscillates ultrasonically to sever the tissue. Furthermore, in the present example blade (454) provides the second polarity of the bipolar RF electrosurgical circuit. Thus, in addition to ultrasonic cutting occurring in distal section (457), RF electrosurgical sealing and coagulation can occur based on the RF electrosurgical pathway extending through tissue between clamp arm (452) and blade (454).

In the illustrated example in FIGS. 46 and 47, blade (454) comprises a groove (462) that extends along its underside. Groove (462) aides in minimizing the thermal capacitance of blade (454) and/or matching the blade's (454) thermal capacitance with that of clamp arm (452). In the present example, groove (462) extends along blade (454) through both distal and proximal sections (457, 456). As seen by comparing blade (454) profile in proximal section (456) versus distal section (457), groove (462) is more pronounced in proximal section (456) where RF electrosurgical sealing occurs.

In proximal section (456) shown in FIG. 47, end effector (450) further includes blade cover (455) that extends along the sides and underside of blade (454). Blade cover (455) is constructed of a nonconductive material in the present example, such as a polymer or ceramic; or coated, dipped, or overmolded stainless steel. As illustrated, the top surfaces of blade cover (455) are raised or elevated relative to the top of blade (454) such that clamp arm (452) engages blade cover (455) when end effector (450) is closed. In the present example the distance that blade cover (455) is raised or elevated relative to blade (454) is represented by D1. Blade cover (455) is also configured such that when clamp arm (452) engages blade cover (455), blade cover (455) deflects. The deflection distance in the present example is represented by D2. The deflection distance is configured to be less than the elevated distance D1 so that blade cover (455) will prevent electrically energized clamp arm (452) from contacting electrically energized blade (454) and thereby short circuiting the desired RF electrosurgical pathway.

Figure 48:
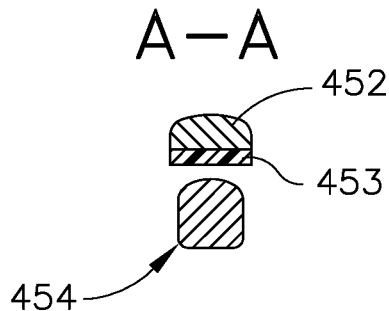
FIG. 48 depicts a cross-section view of another version of the end effector of FIG. 45 taken along the distal section at line A-A of FIG. 45.
Figure 49:
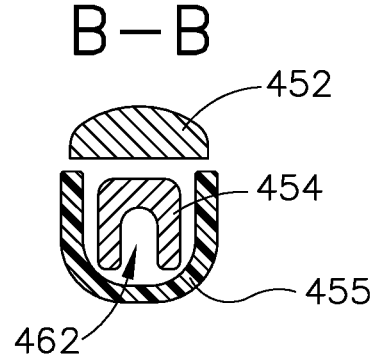
FIG. 49 depicts a cross-section view of the end effector of FIG. 48 taken aloe proximal section at line B-B of FIG. 45.

FIGS. 48-49 show other exemplary cross-sections of a version of end effector (450). With this example, distal section (457) is configured for ultrasonic cutting without RF electrosurgical sealing or coagulation. Furthermore, blade (454) lacks groove (462) along distal section (457). Proximal section (456) in this example is similar to that described with respect to FIG. 47. However, clamp pad (453) is omitted along proximal section (456). Again, blade cover (455) extends above the top of blade (454) to prevent contact between clamp arm (452) and blade (454) when end effector (450) is closed.

Figure 50:
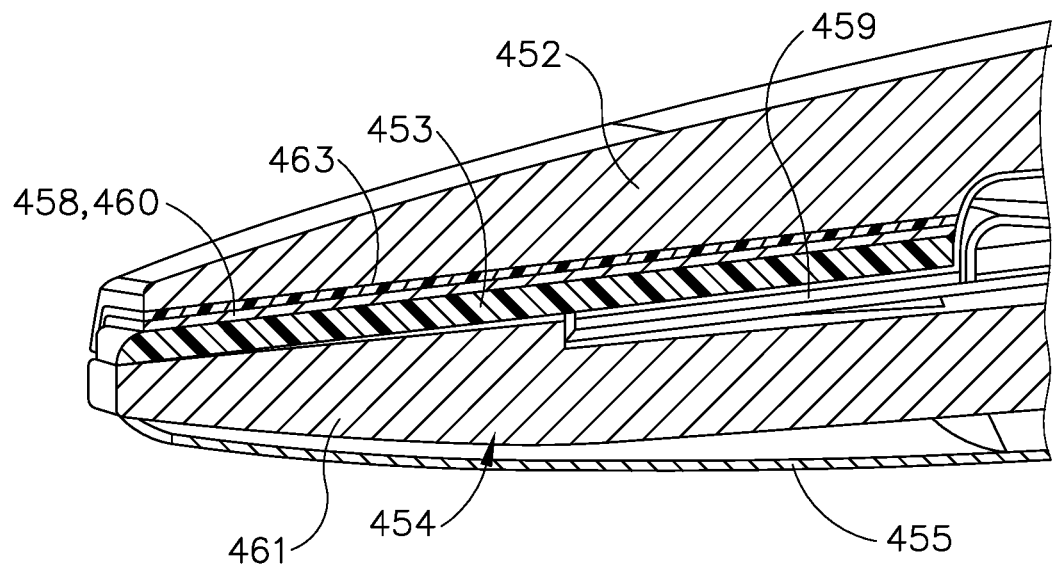
FIG. 50 depicts a perspective view in side cross-section of another version of the end effector of FIG. 45.
Figure 51:
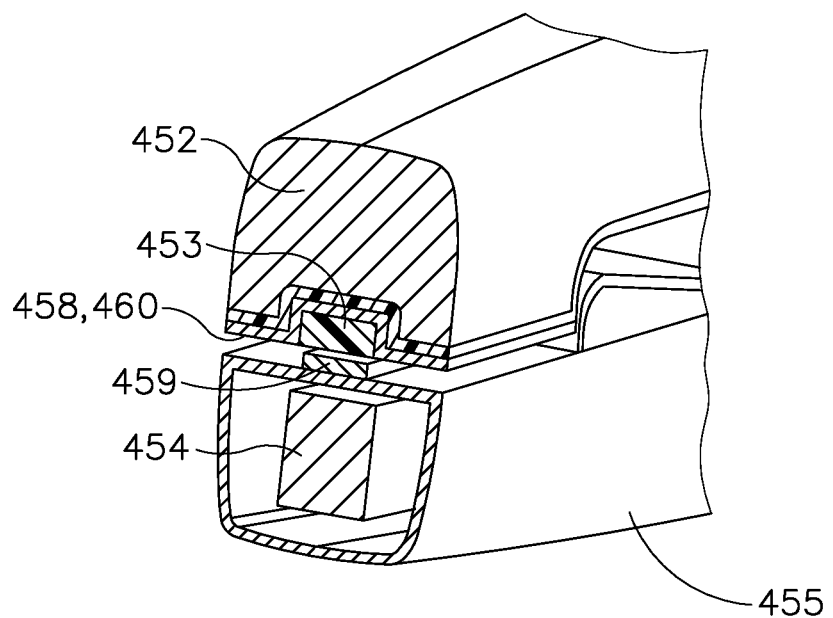
FIG. 51 depicts a perspective view in end cross-section of the end effector of FIG. 50.

FIGS. 50 and 51 show exemplary views of a version of end effector (450) where the poles of the RF electrosurgical circuit are provided by two conductive plates. FIG. 50 shows distal section (457) defining one lengthwise section of the clamping area, and in particular the region where ultrasonic cutting occurs. In the present example, third electrode (460) sits atop of clamp pad (453). A molded top holder (463) is positioned above first electrode (458) and electrically isolates clamp arm (452) from first electrode (458). On the blade side in distal section (457), a top surface of blade (454) is exposed and accessible for contacting clamp pad (453) when end effector (450) is closed. As discussed above, this configuration provides for ultrasonic cutting of clamped tissue. At distal section (457), blade cover (455) extends along the bottom and sides of blade (454), but does not cover the top surface of blade (454).

Referring to FIG. 51, in proximal section (456) blade cover (455) surrounds blade (454) on all sides. Second electrode (459) is positioned on top of blade cover (455) and beneath clamp pad (453). Furthermore, first electrode (458) extends above and along the sides of second electrode (459). With this configuration, clamp pad (453) in proximal section (456) prevents first electrode (458) and second electrode (459) from directly contacting each other when end effector (450) is in a closed position and thus preventing a short circuit. As described above, when tissue is clamped within proximal section (456), RF electrosurgical sealing and coagulation can be delivered through RF electrosurgical energy flowing through the tissue between electrodes (458, 459).

With the configuration of end effector (450) described in the above examples, a larger jaw or clamp can be used while minimizing the power needed for ultrasonic cutting since cutting is limited to only a portion of the entire length of the jaw or clamp. This also reduces the amount of heat generation associated with larger jaw or clamp devices. Furthermore, because of the reduced power need, smaller and/or lightweight transducers can be used.

L. End Effector with Dual Charged Clamp Arms

Figure 52:
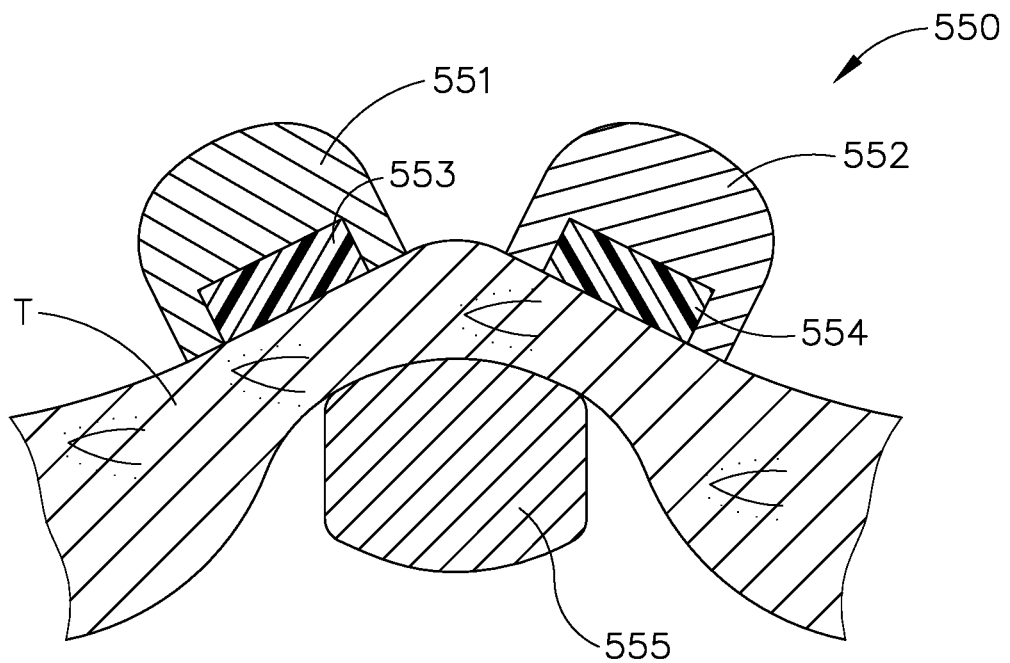
FIG. 52 depicts a cross-section view of another exemplary end effector that may be incorporated into the instrument of FIG. 1.

FIG. 52 shows another exemplary end effector (550) that may be readily incorporated into instrument (110) in place of end effector (140). End effector (550) comprises a first clamp arm (551), and a second clamp arm (552). Clamp arm (551) is connectable with clamp pad (553), and clamp arm (552) is connectable with clamp pad (554). End effector (550) further comprises blade (555). Each respective clamp arm (551, 552) and attached clamp pad (553, 554) is configured to pivot relative to blade (555) between an open position and a closed position to selectively receive and clamp tissue (T) in end effector (550).

In the present example, the pivotal movement of clamp arms (551, 552) occurs in the same or substantially the same manner as the pivoting movement of clamp arm (210) described above. For example, each respective clamp arm (551, 552) is pivotably coupled with an outer tube (202) at one pivot point; and with inner tube (204) at another pivot point. Thus, relative longitudinal movement between tubes (202, 204) provides pivotal movement of clamp arms (551, 552). In some versions, instrument (110) may be configured with additional tubes or adapters that connect with clamp arms (551, 552) to provide pivotal movement as described herein. Furthermore, clamp arms (551, 552) and their associated clamp pads (553, 554) are configured to move either independently or together. In view of the teachings herein, various ways to configure clamp arms (551, 552) with instrument (110) to provide this pivotal movement will be apparent to those of ordinary skill in the art.

Each clamp arm (551, 552) in the present example is provided with a different polarity so that an RF electrosurgical circuit or pathway is created through tissue captured between from clamp arms (551, 552). For instance, clamp arm (551) may have a first electrical polarity while clamp arm (552) may have a second electrical polarity. As described above, the conductive nature of clamp arms (551, 552) may be achieved by combining conductive material(s) (46) with clamp arms (551, 552). The conductive clamp arms (551, 552) are then connectable with an electrical source, such as generator (116), to deliver the electrical energy to clamp arms (551, 552). In view of the teachings herein, various ways for connecting conductive clamp arms (551, 552) with generator (116) or another electrical source will be apparent to those of ordinary skill in the art. Also, any of the methods and techniques described above for altering or modifying clamp arm design to shape the electrosurgical circuit or pathway may be used with clamp arms (551, 552) of end effector (550). In view of the teachings herein, such alterations or modification of clamp arms (551, 552) to shape the electrosurgical circuit and resultant sealing will be apparent to those of ordinary skill in the art. Furthermore, each clamp pad (553, 554) is electrically isolated from its respective clamp arm (551, 552) through various insulating materials as will be understood by those of ordinary skill in the art in view of the teachings herein.

In the example where clamp arms (551, 552) move independently relative to blade (555), either or both clamp arms (551, 552) can be moved to the closed position to compress tissue between the respective clamp pad (553, 554) and blade (555). Blade (555) can be activated to oscillate such that compressed tissue will be ultrasonically severed along the regions where tissue is compressed between clamp pads (553, 554) and blade (555). Because each clamp arm (551, 552) in the present example has a different polarity, to achieve RF electrosurgical sealing, both clamp arms (551, 552) are moved to the closed position so that they contact the captured tissue. With both clamp arms (551, 552) closed, RF electrosurgical sealing can be provided either before, during, or after the ultrasonic cutting process.

Figure 53:
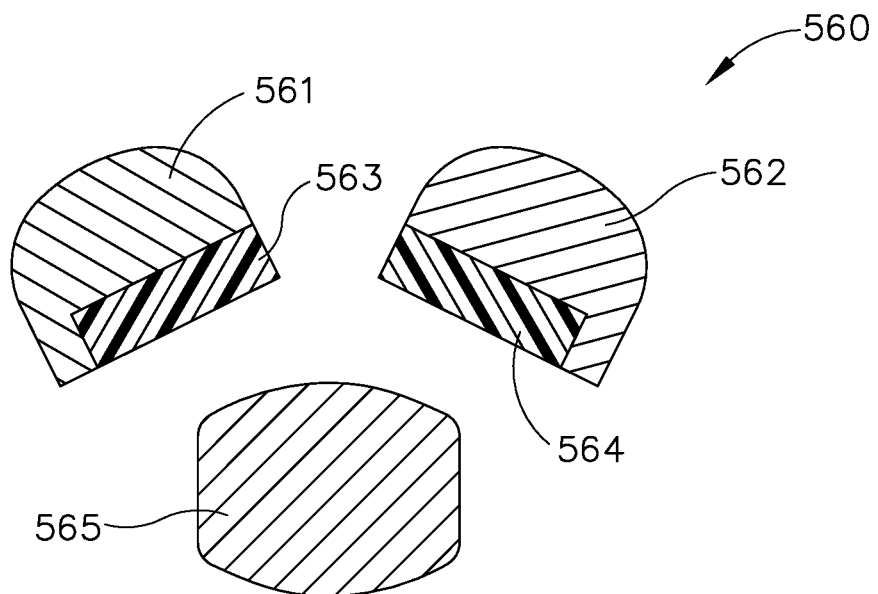
FIG. 53 depicts a cross-section view of another exemplary end effector that may be incorporated into the instrument of FIG. 1.

FIG. 53 shows another exemplary end effector (560) that may be readily incorporated into instrument (110) in place of end effector (140). End effector (560) comprises a first clamp arm (561), a second clamp arm (562), a first clamp pad (563), a second clamp pad (564), and a blade (565). End effector (560) operates the same or similar to end effector (550), and thus the discussion above regarding end effector (550) should be understood to apply also to end effector (560). A difference between end effector (560) and end effector (550) pertains to clamp pads (563, 564). With end effector (560), clamp pads (563, 564) each extend inwardly toward a centerline longitudinal axis of blade (565). In this configuration, clamp arms (561, 562) contact clamped tissue at each outer portion of clamp arms (561, 562). Accordingly, the RF electrosurgical pathway from one clamp arm (561) to the other clamp arm (562) extends only from the outer surface of one clamp arm (561) to the outer surface of the other clamp arm (562). Comparing back to end effector (550), clamp arms (551, 552) are each in contact with clamped tissue on both sides of clamp arms (551, 552). Therefore, with end effector (550) there are four RF electrosurgical pathways from one clamp arm (551) through clamped tissue (T), and to the other clamp arm (552).

Figure 54:
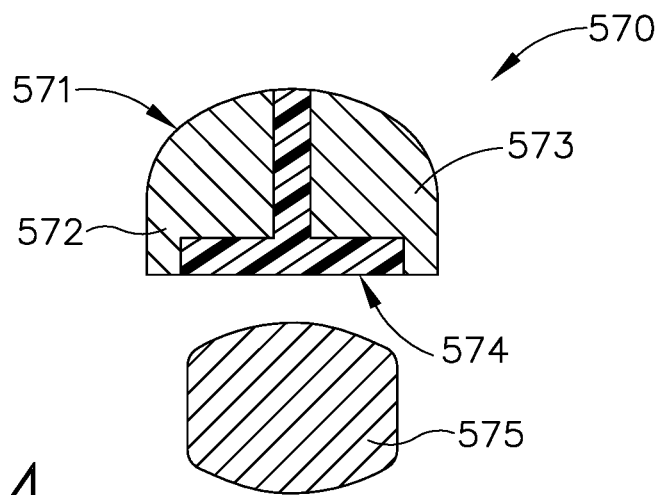
FIG. 54 depicts a cross-section view of another exemplary end effector that may be incorporated into the instrument of FIG. 1.

FIG. 54 shows another exemplary end effector (570) that may be readily incorporated into instrument (110) in place of end effector (140). End effector (570) comprises split clamp arm (571) having a first portion (572) and a second portion (573) that are each oppositely polarized and isolated from one another by pad (574). End effector (570) further comprises nonconductive blade (575). With the split clamp arm configuration, ultrasonic cutting occurs in the same manner as described above with other single clamp arm end effectors. RF electrosurgical sealing occurs similarly to such sealing described above with respect to end effector (560) shown in FIG. 53, there being a single RF electrosurgical pathway from first portion (572) to second portion (573).

Figure 55:
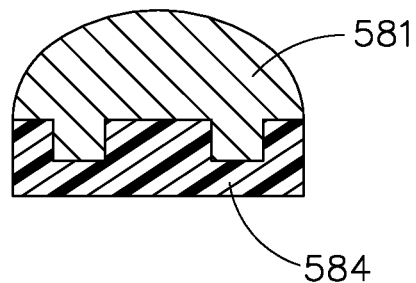
FIG. 55 depicts a cross-section view of an exemplary alternative clamp pad to clamp arm arrangement that may be incorporated into the instrument of FIG. 1.
Figure 56:
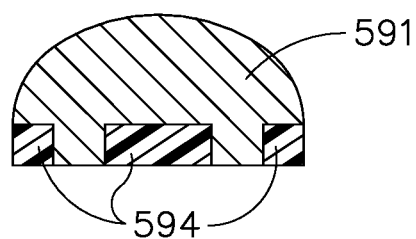
FIG. 56 depicts a cross-section view of another exemplary alternative clamp pad to clamp arm arrangement that may be incorporated into the instrument of FIG. 1.
Figure 57:
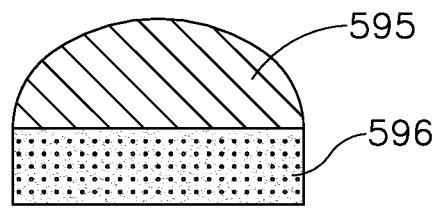
FIG. 57 depicts a cross-section view of another exemplary alternative clamp pad to clamp arm arrangement that may be incorporated into the instrument of FIG. 1.

FIGS. 55-57 show additional clamp pad (584, 594, 596) to clamp arm (581, 591, 595) configurations. For example, FIGS. 55 and 56 show configurations where clamp arms (581, 591) each include two extending portions that may be used to define RF electrosurgical pathways for sealing. FIG. 57 shows a clamp arm (595) attached with a clamp pad (596) where clamp pad (596) comprises multiple capillaries that can be filled with conductive gel to provide RF electrosurgical energy. In view of the teachings herein, other modifications to clamp arm and clamp pad to achieve a desired RF electrosurgical pathway arrangement will be apparent to those of ordinary skill in the art.

III. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a body; (b) a shaft assembly extending distally from the body, wherein the shaft assembly comprises an acoustic waveguide, wherein the acoustic waveguide is configured to communicate ultrasonic vibrations; and (c) an end effector, wherein the end effector comprises: (i) an ultrasonic blade in acoustic communication with the acoustic waveguide, and (ii) a clamp arm assembly, wherein the clamp arm assembly is pivotable toward and away from the ultrasonic blade, wherein the clamp arm assembly comprises: (A) a first electrode, and (B) a second electrode, wherein the first and second electrodes are operable to cooperate to apply bipolar RF energy to tissue.

Example 2

The apparatus of Example 1, wherein the clamp arm assembly defines a length, wherein the first and second electrodes extend longitudinally along the length of the clamp arm assembly.

Example 3

The apparatus of any one or more of Examples 1 through 2, wherein the first electrode is laterally offset from the second electrode.

Example 4

The apparatus of any one or more of Examples 1 through 3, wherein the clamp arm assembly further comprises: (A) a clamp arm body, and (B) a clamp pad, wherein the clamp pad is operable to compress tissue against the ultrasonic blade.

Example 5

The apparatus of Example 4, wherein the first and second electrodes are interposed between the clamp pad and the clamp arm body.

Example 6

The apparatus of Example 5, wherein the clamp pad defines a plurality of openings associated with the first and second electrodes, wherein the openings are configured to provide tissue access to the first and second electrodes through the clamp pad.

Example 7

The apparatus of Example 4, wherein the first electrode defines a first half of the clamp arm body, wherein the second electrode defines a second half of the clamp arm body, wherein the clamp pad is laterally interposed between the first and second electrodes, wherein the clamp pad includes an electrically insulative material.

Example 8

The apparatus of Example 4, wherein the clamp arm body defines the first electrode, wherein the clamp pad defines the second electrode, wherein the clamp arm assembly further comprises an electrical insulator interposed between the clamp arm body and the clamp pad.

Example 9

The apparatus of any one or more of Examples 4 through 8, wherein the clamp arm body defines a plurality of lateral notches, wherein the lateral notches are configured to receive an outward flow of material forming the clamp pad.

Example 10

The apparatus of Example 4, wherein the first electrode comprises a first wire extending along at least a portion of a length of the clamp pad, wherein the second electrode comprises a second wire extending along at least a portion of a length of the clamp pad, wherein portions of the first and second wires are exposed relative to the clamp pad to enable contact with tissue being compressed against the ultrasonic blade by the clamp pad.

Example 11

The apparatus of Example 10, wherein at least a portion of the first wire and at least a portion of the second wire are fully contained within the clamp pad.

Example 12

The apparatus of any one or more of Examples 1 through 4, wherein the first electrode comprises a longitudinally extending body portion and a plurality of laterally extending portions, wherein the laterally extending portions of the first electrode are longitudinally spaced apart from each other, wherein the second electrode comprises a longitudinally extending body portion and a plurality of laterally extending portions, wherein the laterally extending portions of the second electrode are longitudinally spaced apart from each other.

Example 13

The apparatus of Example 12, wherein the laterally extending portions of the first electrode are interdigitated with the laterally extending portions of the second electrode.

Example 14

The apparatus of Example 1, wherein the clamp arm assembly further comprises: (A) a first arm, wherein the first arm provides the first electrode, wherein the first arm is pivotable toward and away from the ultrasonic blade along a first path, and (B) a second arm, wherein the second arm provides the second electrode, wherein the second arm is pivotable toward and away from the ultrasonic blade along a second path.

Example 15

The apparatus of Example 14, wherein the first and second arms are pivotable independently relative to each other.

Example 16

An apparatus comprising: (a) a body; (b) a shaft assembly extending distally from the body, wherein the shaft assembly comprises an acoustic waveguide, wherein the acoustic waveguide is configured to communicate ultrasonic vibrations; and (c) an end effector, wherein the end effector comprises: (i) an ultrasonic blade in acoustic communication with the acoustic waveguide, and (ii) a clamp arm assembly, wherein the clamp arm assembly is pivotable toward and away from the ultrasonic blade, wherein the clamp arm assembly comprises: (A) a conductive body, wherein the conductive body is operable to apply RF energy to tissue, wherein the conductive body defines a plurality of recesses, and (B) a clamp pad supported by the conductive body, wherein the clamp pad is operable to compress tissue against the ultrasonic blade, wherein the recesses are configured to receive a flow of material forming the clamp pad.

Example 17

The apparatus of Example 16, wherein the recesses comprise a plurality of laterally presented notches formed in the conductive body.

Example 18

An apparatus comprising: (a) a body; (b) a shaft assembly extending distally from the body, wherein the shaft assembly comprises an acoustic waveguide, wherein the acoustic waveguide is configured to communicate ultrasonic vibrations; and (c) an end effector, wherein the end effector comprises: (i) an ultrasonic blade in acoustic communication with the acoustic waveguide, (ii) a clamp arm assembly, wherein the clamp arm assembly is pivotable toward the ultrasonic blade to thereby compress tissue against the ultrasonic blade, (iii) a first conductive arm, wherein the first conductive arm is spaced apart from the ultrasonic blade and from the clamp arm assembly, and (iv) a second conductive arm, wherein the second conductive arm is spaced apart from the ultrasonic blade and from the clamp arm assembly, wherein the first and second conductive arms are operable to apply RF energy to tissue.

Example 19

The apparatus of Example 18, wherein the first and second conductive arms are positioned laterally from the ultrasonic blade at opposite lateral sides of the ultrasonic blade, wherein the first and second conductive arms are parallel with the ultrasonic blade.

Example 20

The apparatus of any one or more of Examples 18 through 19, wherein the first and second conductive arms each comprise a non-conductive coating, wherein the non-conductive coatings provide exposed portions of the first and second conductive arms facing the clamp arm assembly.

IV. MISCELLANEOUS

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An apparatus, comprising:
  (a) a shaft assembly comprising an acoustic waveguide, wherein the acoustic waveguide is configured to communicate ultrasonic vibrations; and
  (b) an end effector, wherein the end effector comprises:
    (i) an ultrasonic blade in acoustic communication with the acoustic waveguide, and
    (ii) a clamp arm assembly longitudinally and distally projecting relative to the shaft assembly, wherein the clamp arm assembly is pivotable toward and away from the ultrasonic blade, wherein the clamp arm assembly comprises:
      (A) a first electrode,
      (B) a second electrode, wherein at least two of the first electrode, the second electrode, or the ultrasonic blade are configured to cooperate to apply bipolar RF energy to tissue, and
      (C) a clamp pad defining a centerline longitudinally extending therealong, wherein the clamp pad includes a contact surface configured to contact and compress tissue against the ultrasonic blade, wherein the clamp pad includes a plurality of openings positioned along the centerline and configured to provide discontinuous tissue access, wherein the plurality of openings includes first and second openings, wherein a portion of each of the first and second electrodes is recessed within the first and second openings in a direction away from the contact surface to expose select portion of the first and second electrodes through each of the first and second openings.

2. The apparatus of claim 1, wherein the plurality of openings are uniformly spaced along the centerline.

3. The apparatus of claim 1, wherein the plurality of openings are laterally centered about the centerline.

4. The apparatus of claim 1, wherein the first opening is an oval shaped opening.

5. The apparatus of claim 1, wherein each of the plurality of openings extends laterally across the centerline such that the clamp pad is not a continuous pad material along the centerline.

6. The apparatus of claim 1, further comprising a clamp arm body, wherein the first electrode includes a first body portion and a first terminal, wherein the first terminal transversely extends from the first body portion toward the clamp arm body, wherein the second electrode includes a second body portion and a second terminal.

7. The apparatus of claim 6, wherein the first body portion includes a first exposed surface extending through the openings, wherein the first exposed surface faces toward the ultrasonic blade and is configured to engage the tissue, wherein the second body portion includes a second exposed surface extending through the openings, wherein the second exposed surface faces toward the ultrasonic blade and is configured to engage the tissue.

8. The apparatus of claim 6, further comprising a clamp arm body that includes an outer surface facing away from the ultrasonic blade and defines a first opening transversely extending through the outer surface, wherein the first opening of the clamp arm body receives a first portion of the clamp pad such that the first portion of the clamp pad is exposed through the first opening of the clamp arm body.

9. The apparatus of claim 8, wherein the first terminal transversely extends from the first body portion transversely beyond the outer surface of the clamp arm body, wherein the second terminal transversely extends from the second body portion transversely beyond the outer surface of the clamp arm body.

10. The apparatus of claim 6, wherein the clamp arm body defines a first opening that receives a first portion of the clamp pad, wherein the first terminal transversely extends through the first portion of the clamp pad and the first opening of the clamp arm body such that the first terminal is laterally interposed between the clamp pad and the clamp arm body.

11. The apparatus of claim 1, wherein the first and second electrodes have a first polarity, wherein the ultrasonic blade has a second polarity that is opposite to the first polarity, wherein the bipolar RF energy is configured to be applied to provide conductive pathways through the tissue between the first electrode and the ultrasonic blade and between the second electrode and the ultrasonic blade.

12. The apparatus of claim 1, wherein the first electrode has a first polarity, wherein the second electrode has a second polarity that is opposite to the first polarity, wherein the ultrasonic blade has a neutral polarity that is different from the first and second polarities, wherein the bipolar RF energy is configured to be applied to provide conductive pathways through the tissue between the first and second electrodes disposed within the first opening.

13. The apparatus of claim 1, wherein the clamp arm assembly is pivotable toward and away from the ultrasonic blade between open and closed configurations, wherein the first electrode is spaced a fixed distance from the second electrode in each of the open and closed configurations.

14. The apparatus of claim 13, wherein the contact surface of the clamp pad is configured to contact and compress tissue against the ultrasonic blade in response to the clamp arm assembly including the clamp pad, the first electrode, and the second electrode pivoting toward the ultrasonic blade toward the closed configuration.

15. The apparatus of claim 13, wherein the contact surface of the clamp pad is configured to contact and compress tissue against the ultrasonic blade in response to the at least the clamp pad, the first electrode, and the second electrode pivoting toward the ultrasonic blade from the open configuration to the closed configuration.

16. A method of treating a tissue with a surgical instrument, wherein the surgical instrument includes (a) a shaft assembly comprising an acoustic waveguide, wherein the acoustic waveguide is configured to communicate ultrasonic vibrations; and (b) an end effector, wherein the end effector comprises: (i) an ultrasonic blade in acoustic communication with the acoustic waveguide, and (ii) a clamp arm assembly longitudinally and distally projecting relative to the shaft assembly, wherein the clamp arm assembly is pivotable toward and away from the ultrasonic blade, wherein the clamp arm assembly comprises: (A) a first electrode, (B) a second electrode, wherein at least two of the first electrode, the second electrode, or the ultrasonic blade are configured to cooperate to apply bipolar RF energy to tissue, and (C) a clamp pad defining a centerline longitudinally extending therealong, wherein the clamp pad includes a contact surface configured to contact and compress tissue against the ultrasonic blade, wherein the clamp pad includes a plurality of openings positioned along the centerline and configured to provide discontinuous tissue access, wherein the plurality of openings includes first and second openings, the method comprising:

(a) applying bipolar RF energy using at least two of the first and second electrodes or the ultrasonic blade, wherein the first and second electrodes are each recessed within the first and second openings in a direction away from the contact surface exposing select portions of each of the first and second electrodes thereby sealing a plurality of discrete locations of the tissue in a discontinuous manner.

17. The method of claim 16, wherein the ultrasonic blade is configured to align with a centerline of the clamp pad that extends between the first and second electrodes, wherein the plurality of openings extend across the centerline, wherein the method further comprises gripping the tissue intermittently or in a discontinuous manner because the openings interrupt the centerline.

18. The method of claim 16, further comprising compressing the tissue to at least partially fill the first or second openings so that the tissue is contacting the first and second electrodes in first and second discrete locations of the plurality of discrete locations.

19. The method of claim 16, wherein the clamp pad defines a length, wherein the first and second electrodes extend along a majority of the length of the clamp pad.

20. An apparatus, comprising:
(a) a shaft assembly comprising an acoustic waveguide, wherein the acoustic waveguide is configured to communicate ultrasonic vibrations; and
(b) an end effector, wherein the end effector comprises:
(i) an ultrasonic blade in acoustic communication with the acoustic waveguide, and
(ii) a clamp arm assembly longitudinally and distally projecting relative to the shaft assembly, wherein the clamp arm assembly is pivotable toward and away from the ultrasonic blade, wherein the clamp arm assembly comprises:
(A) a first electrode, (B) a second electrode, wherein at least two of the first electrode, the second electrode, or the ultrasonic blade are configured to cooperate to apply bipolar RF energy to tissue, and (C) a clamp pad defining a centerline longitudinally extending therealong, wherein the clamp pad includes a contact surface configured to contact and compress tissue against the ultrasonic blade, wherein the clamp pad includes a plurality of openings positioned along the centerline and configured to provide discontinuous tissue access, wherein the plurality of openings includes first and second openings, wherein a portion of each of the first and second electrodes is recessed within the first and second openings in a direction away from the contact surface, wherein the clamp pad defines a length, wherein the first and second electrodes extend along a majority of the length of the clamp pad, wherein the first and second openings expose select portions of each of the first and second electrodes.

* * * * *